United States Patent
Dave et al.

(10) Patent No.: US 12,076,440 B2
(45) Date of Patent: Sep. 3, 2024

(54) POWDER BLEND PROCESSABILITY IMPROVEMENTS THROUGH MINIMAL AMOUNTS OF SYNERGISTICALLY SELECTED SURFACE COATING AGENTS

(71) Applicant: New Jersey Institute of Technology, Newark, NJ (US)

(72) Inventors: Rajesh N. Dave, Princeton, NJ (US); Sangah Kim, Newark, NJ (US); Zhixing Lin, Newark, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 0 days.

(21) Appl. No.: 18/221,143

(22) Filed: Jul. 12, 2023

(65) Prior Publication Data

US 2024/0024241 A1     Jan. 25, 2024

Related U.S. Application Data

(60) Provisional application No. 63/388,422, filed on Jul. 12, 2022.

(51) Int. Cl.
| | |
|---|---|
| *A61K 9/14* | (2006.01) |
| *A61K 9/16* | (2006.01) |
| *A61K 31/192* | (2006.01) |
| *A61K 45/06* | (2006.01) |
| *B82Y 5/00* | (2011.01) |
| *B82Y 30/00* | (2011.01) |

(52) U.S. Cl.
CPC ............ *A61K 9/143* (2013.01); *A61K 9/1682* (2013.01); *A61K 31/192* (2013.01); *A61K 45/06* (2013.01); *B82Y 5/00* (2013.01); *B82Y 30/00* (2013.01)

(58) Field of Classification Search
CPC .... A61K 9/143; A61K 9/1682; A61K 31/192; A61K 45/06; B82Y 5/00; B82Y 30/00
See application file for complete search history.

(56) References Cited

PUBLICATIONS

Huang et al. (European Journal of Pharmaceutical Sciences 2017; 104:344-355) (Year: 2017).*

(Continued)

*Primary Examiner* — Ernst V Arnold
(74) *Attorney, Agent, or Firm* — Lerner David LLP

(57) ABSTRACT

High (greater than 30%) and/or low (less than 10%) loaded multiple API powdered/nanoparticle were tabulated with increased flowability and physical properties. Properties include blend flowability and uniformity, bulk packing density, compactability, tensile strength, and dissolution. Blending is done through solventless dry mechanical coating of at least one minority API component defined as the API component with the least weight per volume surface coated with nano-sized powders in lesser amounts by wt % of the blend, and preferably less than 10% dry coated of the minority API. An excipient may be dry coated in the lesser amount wherein the excipient is a minority component. Both minority excipient and minority API may be dry coated. Using dry coating instead of dry granulation and/or wet granulation techniques in producing tablets saves manufacturing steps, costs, and produces higher quality tablets with surprisingly higher properties than expected for low flowability solid powdered ingredients.

25 Claims, 44 Drawing Sheets

Bulk density (BD) and Unconfined Yield Strength (UYS) of the API before and after dry coating indicating significant positive impact for all cases of dry coating. Illustrative lines are for better visualization of the BD and UYS trends

(56) References Cited

PUBLICATIONS

Dupont Avicel®PH102 ([online] retrieved on Oct. 7, 2023 from: file:///C:/Users/earnold/Documents/e-Red%20Folder/18221143/avicelPH102%20bulk%20density.pdf; 2 pages). (Year: 2023).*
Zhou et al. (Powder Technology 2013;249:290-296) (Year: 2013).*
Mullarney et al. (Pharmaceutical Technology 2011;35(10): 5 pages). (Year: 2011).*
Chen, L. et al., "Fine grade engineered microcrystalline cellulose excipients for direct compaction: Assessing suitability of different dry coating processes," European Journal of Pharmaceutical Sciences, Jun. 3, 2020, vol. 151 (2020), pp. 105408 (1-10), Elsevier.
Chen, L. et al., "Surface engineered excipients: I. improved functional properties of fine grade microcrystalline cellulose," International Journal of Pharmaceutics, Nov. 28, 2017, vol. 536 (2018), pp. 127-137, Elsevier.
Chen, L. et al., "Surface engineered excipients: III. Facilitating direct compaction tableting of binary blends containing fine cohesive poorly-compactable APIs," International Journal of Pharmaceutics, Dec. 29, 2018, vol. 557 (2019), pp. 354-365, Elsevier.
Han, X. et al., "Passivation of High-Surface-Energy Sites of Milled Ibuprofen Crystals via Dry Coating for Reduced Cohesion and Improved Flowability," Journal of Pharmaceutical Sciences, vol. 102, No. 7, May 8, 2013, pp. 2282-2296.
Huang, Z. et al., "Flow and bulk density enhancements of pharmaceutical powders using a conical screen mill: A continuous dry coating device," Chemical Engineering Science, Jun. 2, 2014, vol. 125 (2015), pp. 209-224, Elsevier.
Huang, Z. et al., "Improved blend and tablet properties of fine pharmaceutical powders via dry particle coating,"International Journal of Pharmaceutics, Dec. 2, 2014, vol. 478 (2015), pp. 447-455, Elsevier.
Huang, Z. et al., "Improving blend content uniformity via dry particle coating of micronized drug powders," European Journal of Pharmaceutical Sciences, Apr. 20, 2017, vol. 104 (2017), pp. 344-355, Elsevier.
Jallo, L.J. et al. "Improvement of flow and bulk density of pharmaceutical powders using surface modification," International Journal of Pharmaceutics, Dec. 17, 2011, vol. 423 (2012), pp. 213-225, Elsevier.
Jallo, L.J. et al. "Prediction of Inter-particle Adhesion Force from Surface Energy and Surface Roughness," Journal of Adhesion Science and Technology, Apr. 2, 2012, vol. 25 (2011), pp. 367-384.
Kim, S. et al., "Impact of altered hydrophobicity and reduced agglomeration on dissolution of micronized poorly water-soluble drug powders after dry coating," International Journal of Pharmaceutics, Jul. 10, 2021, vol. 606 (2021), pp. 120853 (1-16), Elsevier.
Kunnath, K. et al., "Improved properties of fine active pharmaceutical ingredient powder blends and tablets at high drug loading via dry particle coating," International Journal of Pharmaceutics, Apr. 3, 2018, vol. 543 (2018), pp. 288-299, Elsevier.
Mullarney, M.P. et al., "Applying dry powder coatings to pharmaceutical powders using a comil for improving powder flow and bulk density," Powder Technology, Jun. 16, 2011, vol. 212 (2011), pp. 397-402, Elsevier.

* cited by examiner

Figure 1. SEM images of milled ibuprofen before and after dry coating: (a) uncoated; (b) fixed wt% R972P coated; (c) fixed wt% A200 coated; (d) fixed %SAC R972P coated; (e) fixed %SAC A200 coated

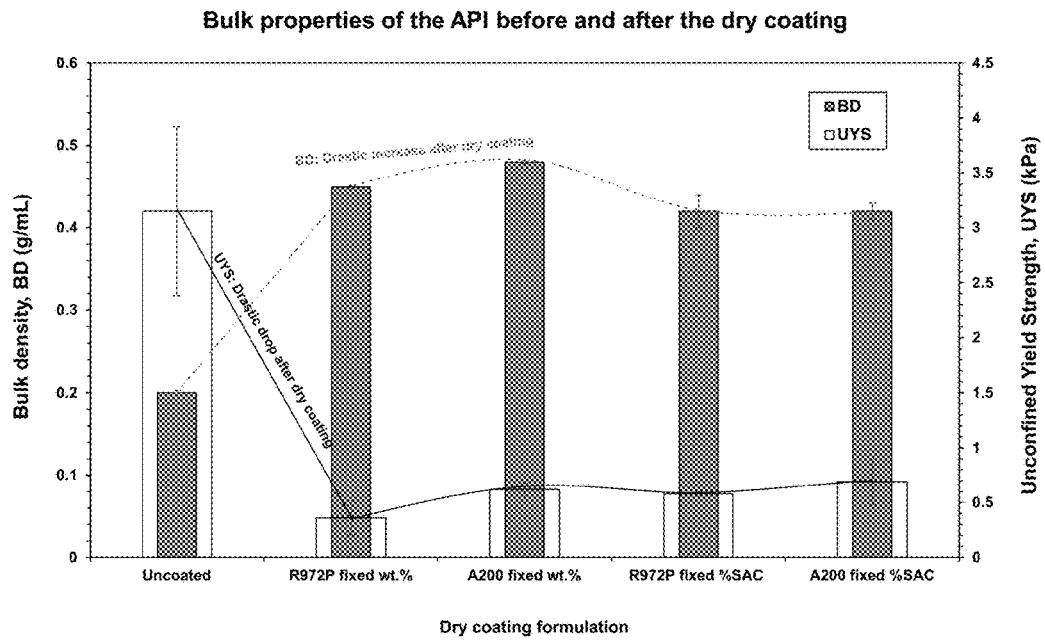

Figure 2. Bulk density (BD) and Unconfined Yield Strength (UYS) of the API before and after dry coating indicating significant positive impact for all cases of dry coating. Illustrative lines are for better visualization of the BD and UYS trends

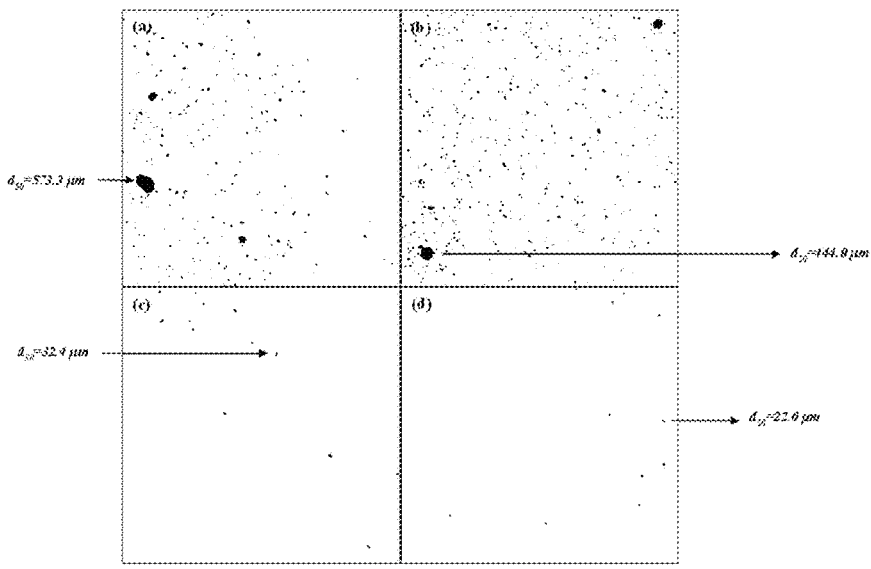

Figure 3A-3D. Typical images of uncoated and dry coated Ibu obtained via Gradis/QicPic, demonstrating significant reduction in agglomerate sizes after dry coating: (a) uncoated Ibu10; (b) another image of uncoated Ibu10; (c) A200 fixed wt % dry coated Ibu10; (d) R972P fixed wt % dry coated Ibu10

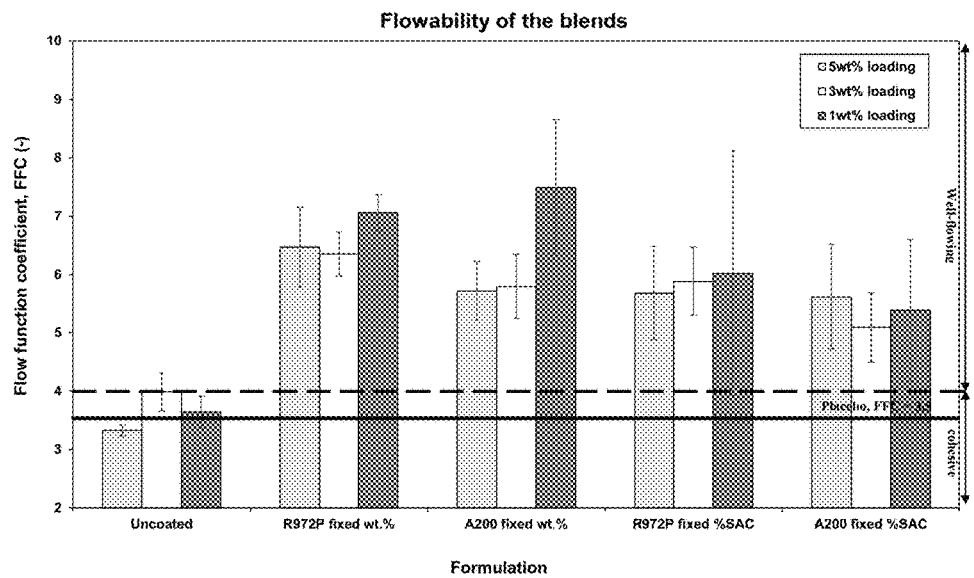
Figure 4. Flowability of all blends with and without API dry coating. Note the solid horizontal line for the FFC of placebo blend and dashed line to mark two flow regimes, cohesive and well-flowing
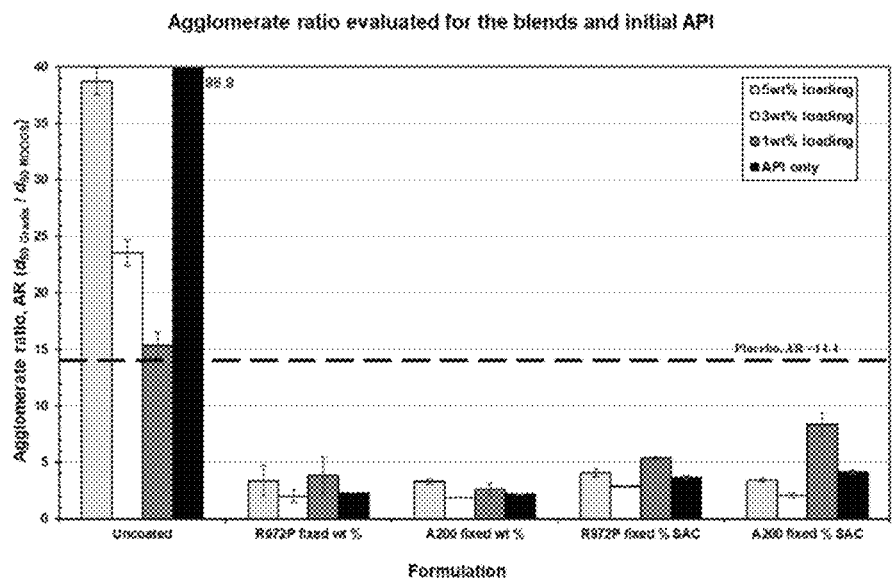
Figure 5. Agglomerate ratio of the API and all the blends with and without dry coating. Note the dotted horizontal line for the AR of placebo blend

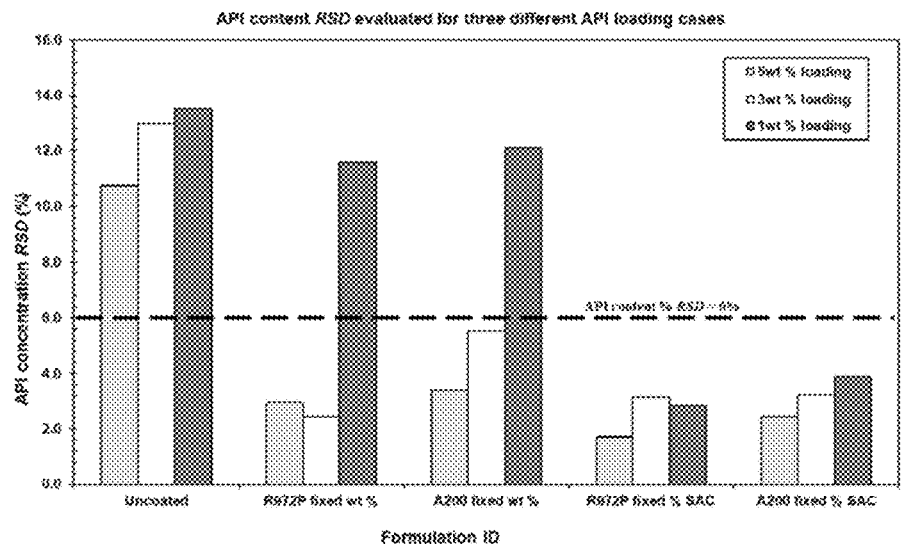
Figure 6. Blend uniformity for three different API loadings before and after dry coating. The dashed line represents target %RSD to discern uniformity of blends
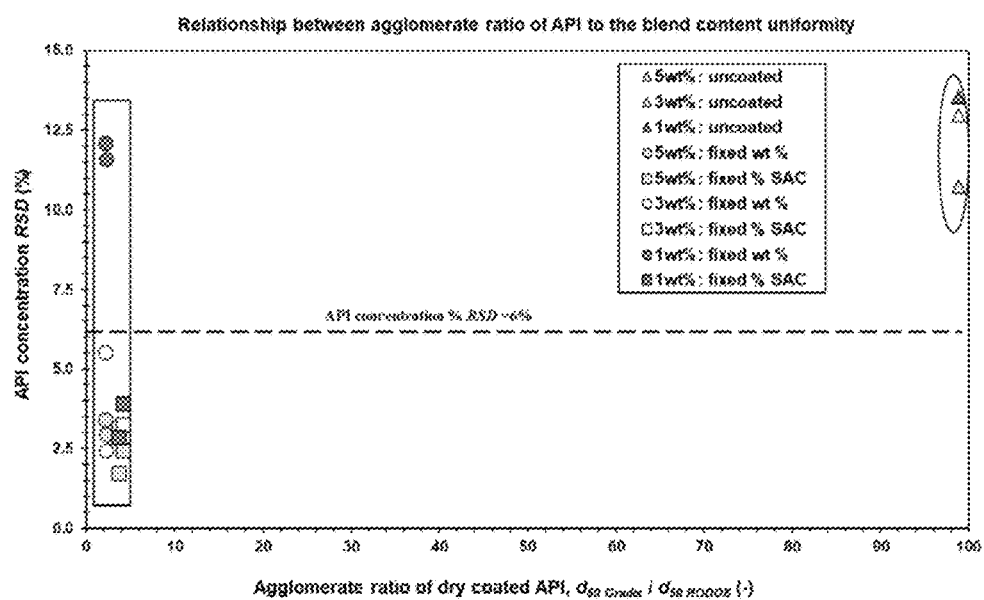
Figure 7. The blend uniformity plotted as a function of the API agglomerate size ratio

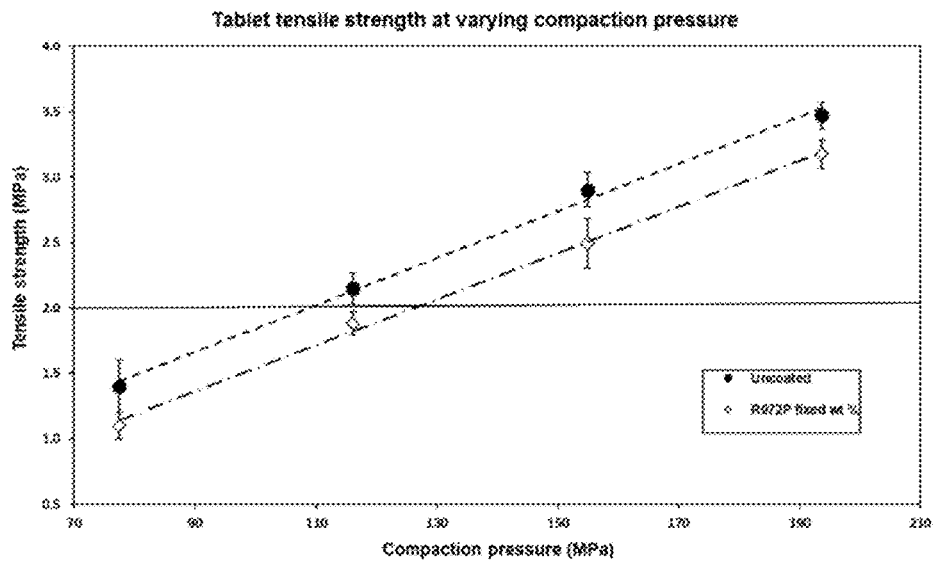

Figure 8. Tablet tensile strength of the 3 wt % API loading blends with and without fixed wt % R972P coating at four different compaction forces

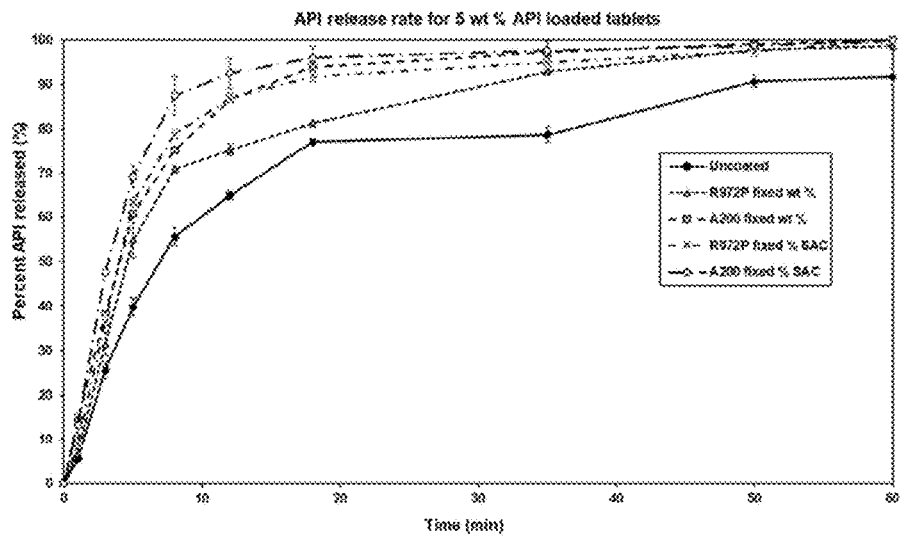

Fig 9A.

Figures 9A-9C. API release rate from 400mg tablets (outer diameter 12.76 +/- 0.02mm; thickness 2.61 +/- 0.03mm; compressed at 77MPa) using USP II method for all three API loaded tablets with and without API dry coating: Fig. 9(a) 5 wt% loading; Fig. 9(b) 3 wt% loading; Fig. 9(c) 1 wt% loading.

Agglomerate ratio, AR of low API loaded coarse and weakly cohesive blends at different mixing times: for (a) 5 wt % API loaded coarse and weakly cohesive blends and (b) 1 wt % API loaded coarse and weakly cohesive blends.

Flowability, Flow Function Coefficient (FFC) of low API loaded coarse and weakly cohesive blends at different mixing times: for (a) 5 wt % API loaded coarse and weakly cohesive blends and (b) 1 wt % API loaded coarse and weakly cohesive blends Uniformity of the blends with either uncoated or dry coated API at different mixing times for: (a) 5 wt % coarse and weakly cohesive multi-component blends and (b) 1 wt% coarse and weakly cohesive multi-component blends.

Drug release profile for 5 wt % loaded 400 mg tablets in pH 7.2 phosphate buffer in USP II apparatus at 37.8 ± 0.3°C: (a) coarse blend tablets mixing time of 10min; (b) coarse blend tablets mixing time of 60min Agglomerate ratio of fine and cohesive blends at different mixing times and dry coating formulations for: (a) 5 wt % API loading and (b) 1 wt% API loading blends.

Figures 15A-15B. Flowability, Flow Function Coefficient (FFC) of low API loaded fine and cohesive blends at different mixing times: for Figure 15A 5 wt % API loaded fine and cohesive blends and Figure 15B 1 wt % API loaded fine and cohesive blends.

Uniformity of the blends with either uncoated or dry coated API at different mixing times for: (a) 5 wt % fine and cohesive multi-component blends and (b) 1 wt% fine and cohesive multi-component blends Drug release profile for 5 wt % loaded 400 mg tablets in pH 7.2 phosphate buffer in USP II apparatus at 37.8 ± 0.3°C: (a) fine blend tablets mixing time of 5 min; (b) fine blend tablets mixing time of 60 min SEM images of disintegrants before and after dry coating for Figure 18(a) uncoated Kollidon CLF; Figure 18 (b) 1 wt% A200 coated Kollidon CLF; Figure 18 (c) uncoated HPC SSL-SFP; Figure 18 (d) 1wt% A200 coated HPC SSL-SFP; Figure 18 (e) uncoated HPC SSL; Figure 18 (f) 1wt% A200 coated HPC SSL SEM images of: (a) uncoated Kollindon CL-F; (b) 1 wt%A200 coated Kollindon CL-F; (c) uncoated HPC SSL-SFP; (d) 1 wt%A200 coated HPC SSL-SFP A plot of FFC for blends in Example 14.

A plot of bulk density for blends in Example 14.

A plot of tensile strength for blends in Example 15.

SEM images of: (a) uncoated Avicel® 105; (b) 1 wt%A200 coated Avicel® 105.

A plot of FFC for blends in Example 16.

A plot of bulk density for blends in Example 16.

A plot of tensile strength for blends in Example 16.

Mean particle size and true particle density values of excipients and milled Ibuprofen

| Component | Mean particle size at 1.0 bar dispersion (μm) | Particle density (g/mL) |
|---|---|---|
| Avicel 105 | 18.9 ± 0.1 | 1.43 ± 0.01 |
| Pharmatose 450 | 19.5 ± 1.7 | 1.48 ± 0.01 |
| Kollidon-CL | 38.0 ± 0.1 | 1.12 ± 0.01 |
| MgSt | 7.7 ± 0.2 | 1.01 ± 0.01 |
| Milled ibuprofen (Ibu) | 14.0 ± 0.2 | 1.14 ± 0.01 |

Figure 27.

Details of the multi-component blend formulations

| API wt% | | 5wt% loading | | | | | 3wt% loading | | | | | 1wt% loading | | | | |
|---|---|---|---|---|---|---|---|---|---|---|---|---|---|---|---|---|
| | Placebo | Uncoated | Fixed wt % dry coating (either minimized or maximized surface wettability) | | Fixed% SAC (50% SAC) dry coating | | Uncoated | Fixed wt % dry coating (either minimized or maximized surface wettability) | | Fixed% SAC (50% SAC) dry coating | | Uncoated | Fixed wt % dry coating (either minimized or maximized surface wettability) | | Fixed% SAC (50% SAC) dry coating | |
| Components | | | R972P | A200 | R972P | A200 | | R972P | A200 | R972P | A200 | | R972P | A200 | R972P | A200 |
| API | 0 | 5 | 5 | 5 | 5 | 5 | 3 | 3 | 3 | 3 | 3 | 1 | 1 | 1 | 1 | 1 |
| R972P | 0 | 0 | 0.116 | 0 | 0.058 | 0 | 0 | 0.069 | 0 | 0.035 | 0 | 0 | 0.023 | 0 | 0.012 | 0 |
| A200 | 0 | 0 | 0 | 0.116 | 0 | 0.033 | 0 | 0 | 0.069 | 0 | 0.020 | 0 | 0 | 0.023 | 0 | 0.007 |
| Avicel 105 | 47 | 44.5 | 44.4 | 44.4 | 44.5 | 44.5 | 45.5 | 45.5 | 45.5 | 45.5 | 45.5 | 46.5 | 46.5 | 46.5 | 46.5 | 46.5 |
| Pharmatose 450 | 47 | 44.5 | 44.4 | 44.4 | 44.5 | 44.5 | 45.5 | 45.5 | 45.5 | 45.5 | 45.5 | 46.5 | 46.5 | 46.5 | 46.5 | 46.5 |
| Kollidon-CL | 5 | 5 | 5 | 5 | 5 | 5 | 5 | 5.0 | 5.0 | 5 | 5 | 5 | 5 | 5 | 5 | 5 |
| MgSt | 1 | 1 | 1 | 1 | 1 | 1 | 1 | 1 | 1 | 1 | 1 | 1 | 1 | 1 | 1 | 1 |
| Total wt.% | 100 | 100 | 100 | 100 | 100 | 100 | 100 | 100 | 100 | 100 | 100 | 100 | 100 | 100 | 100 | 100 |

Figure 28.

The Characteristic particle size distributions for the uncoated and dry coated Ibu using both the compressed air (Rodos) and gravity driven (Gradis) methods

| Dispersion methods | Compressed Air (1.0bar): Rodos | | | Gravity driven: Gradis | | | |
|---|---|---|---|---|---|---|---|
| Sample Description (API only) | $d_{10}$ (μm) | $d_{50}$ (μm) | $d_{90}$ (μm) | $d_{10}$ (μm) | $d_{50}$ (μm) | $d_{90}$ (μm) | $d_{99}$ (μm) |
| Uncoated | 4.2 ± 0.1 | 14.0 ± 0.2 | 35.4 ± 0.4 | 56.6 ± 9.9 | 1380 ± 550 | 2492 ± 558 | 2738 ± 517 |
| R972P fixed wt % | 4.5 ± 0.0 | 12.4 ± 0.0 | 26.8 ± 0.2 | 16.1 ± 0.2 | 28.6 ± 0.2 | 46.0 ± 0.7 | 138 ± 63 |
| A200 fixed wt % | 4.9 ± 0.0 | 13.7 ± 0.1 | 30.3 ± 0.4 | 17.2 ± 0.2 | 29.8 ± 0.2 | 50.9 ± 0.6 | 350 ± 495 |
| R972P fixed% SAC | 4.4 ± 0.0 | 14.1 ± 0.0 | 33.4 ± 0.1 | 25.9 ± 0.6 | 51.8 ± 6.0 | 382 ± 124 | 482 ± 109 |
| A200 fixed% SAC | 4.4 ± 0.0 | 14.5 ± 0.2 | 35.0 ± 0.6 | 27.2 ± 0.6 | 59.9 ± 5.9 | 570 ± 48 | 676 ± 198 |

Figure 29.

The characteristic particle size distributions measured via Gradis/QicPic and Rodos/Helos for the placebo and three different drug loaded blends with and without silica dry coating

| | 5% loading | | | 3% loading | | | 1% loading | | |
|---|---|---|---|---|---|---|---|---|---|
| Gradis/QicPic (Agglomerated size) | $d_{10}$ | $d_{50}$ | $d_{90}$ | $d_{10}$ | $d_{50}$ | $d_{90}$ | $d_{10}$ | $d_{50}$ | $d_{90}$ |
| Placebo | 37.0 ± 11.7 | 276 ± 322 | 1234 ± 707 | 37.02 ± 11.7 | 276 ± 322 | 1234 ± 707 | 37.0 ± 11.7 | 276 ± 322 | 1237 ± 707 |
| Uncoated | 72.8 ± 68.6 | 707 ± 913 | 1683 ± 780 | 18.1 ± 0.8 | 439 ± 205 | 1106 ± 601 | 26.3 ± 6.1 | 294 ± 484 | 892 ± 714 |
| R972P fixed wt % coated | 24.0 ± 2.6 | 62.1 ± 16.9 | 303 ± 158 | 18.1 ± 0.4 | 37.6 ± 1.6 | 469 ± 761 | 22.2 ± 3.3 | 73.0 ± 39.0 | 853 ± 771 |
| A200 fixed wt % coated | 24.0 ± 3.5 | 60.4 ± 22.4 | 229 ± 131 | 17.5 ± 0.2 | 35.7 ± 0.6 | 72.7 ± 19.5 | 20.6 ± 0.8 | 50.1 ± 7.6 | 412 ± 413 |
| R972P fixed % SAC coated | 26.4 ± 0.9 | 75.4 ± 10.1 | 1019 ± 708 | 20.2 ± 1.4 | 53.5 ± 11.7 | 982 ± 766 | 22.3 ± 3.1 | 103 ± 108 | 624 ± 765 |
| A200 fixed % SAC coated | 24.6 ± 10.0 | 63.3 ± 28.1 | 494 ± 364 | 18.3 ± 0.2 | 39.1 ± 1.0 | 123.5 ± 27.8 | 23.5 ± 4.0 | 16 ± 216 | 758 ± 841 |
| Rodos/Helos 1.0bar (Primary size) | $d_{10}$ | $d_{50}$ | $d_{90}$ | $d_{10}$ | $d_{50}$ | $d_{90}$ | $d_{10}$ | $d_{50}$ | $d_{90}$ |
| Placebo | 4.3 ± 0.1 | 19.1 ± 0.1 | 47.5 ± 0.2 | 4.3 ± 0.1 | 19.1 ± 0.1 | 47.5 ± 0.2 | 4.3 ± 0.1 | 19.1 ± 0.1 | 47.5 ± 0.2 |
| Uncoated | 3.4 ± 0.1 | 18.3 ± 0.1 | 47.1 ± 0.1 | 3.4 ± 0.0 | 18.6 ± 0.0 | 46.9 ± 0.0 | 3.8 ± 0.1 | 19.1 ± 0.1 | 46.7 ± 0.2 |
| R972P fixed wt % coated | 3.5 ± 0.0 | 18.4 ± 0.0 | 47.0 ± 0.0 | 3.5 ± 0.1 | 18.6 ± 0.0 | 46.4 ± 0.1 | 3.8 ± 0.0 | 19.1 ± 0.0 | 46.4 ± 0.1 |
| A200 fixed wt % coated | 3.6 ± 0.1 | 18.3 ± 0.1 | 47.0 ± 0.2 | 3.4 ± 0.0 | 18.6 ± 0.1 | 46.6 ± 0.0 | 3.9 ± 0.0 | 19.2 ± 0.0 | 46.5 ± 0.2 |
| R972P fixed % SAC coated | 3.6 ± 0.1 | 18.4 ± 0.1 | 47.1 ± 0.0 | 3.5 ± 0.1 | 18.8 ± 0.1 | 47.1 ± 0.1 | 3.9 ± 0.0 | 19.3 ± 0.0 | 46.3 ± 0.3 |
| A200 fixed % SAC coated | 3.6 ± 0.1 | 18.4 ± 0.1 | 47.2 ± 0.1 | 3.5 ± 0.0 | 18.8 ± 0.0 | 47.0 ± 0.1 | 3.9 ± 0.0 | 19.2 ± 0.1 | 46.4 ± 0.2 |

Figure 30.

The bulk properties of the API (milled Ibu) before and after the dry coating

| Sample Description (API only) | Bulk density (g/mL) | Cohesion (kPa) | Unconfined Yield strength, UYS (kPa) | Flow function coefficient, FFC (-) | Flow behavior [7] |
|---|---|---|---|---|---|
| Uncoated Ibu10 | 0.24 ± 0.003 | 0.99 ± 0.30 | 3.15 ± 0.77 | 1.90 ± 0.45 | Very cohesive, not flowing |
| R972P fixed wt % coated | 0.48 ± 0.002 | 0.11 ± 0.05 | 0.36 ± 0.16 | 26.04 ± 14.73 | Free Flowing |
| A200 fixed wt % coated | 0.45 ± 0.002 | 0.18 ± 0.02 | 0.62 ± 0.06 | 9.21 ± 1.52 | Well flowing |
| R972P fixed % SAC coated | 0.42 ± 0.01 | 0.14 ± 0.01 | 0.58 ± 0.02 | 10.20 ± 0.61 | Free Flowing |
| A200 fixed % SAC coated | 0.42 ± 0.02 | 0.19 ± 0.05 | 0.69 ± 0.21 | 7.66 ± 1.92 | Well flowing |

Figure 31.

Properties of components

| Component | Mean particle size at 1.0 bar dispersion (μm) | Particle density (g/mL) |
|---|---|---|
| Ibu10 (API) | 14.0 ± 0.2 | 1.14± 0.01 |
| Avicel PH102 | 112.74 ± 0.1 | 1.60 ± 0.004 |
| Pharmatose DCL11 | 116.07 ± 0.1 | 1.60± 0.004 |
| Kollidon-CL | 38.0 ± 0.1 | 1.12 ± 0.01 |
| MgSt | 7.7 ± 0.2 | 1.01 ± 0.01 |
| R972P (hydrophobic nano fumed silica) | 0.018 | 2200 |
| A200 (hydrophilic nano fumed silica) | 0.012 | 2650 |

Figure 32.

Coating formulation

| Case | Coating materials | weight % | API | Weight % |
|---|---|---|---|---|
| Fixed SAC % | R972P | 1.16 | Ibu10 | 98.84 |
| | A200 | 0.65 | | 99.35 |
| Fixed wt % | R972P | 2.31 | | 97.69 |
| | A200 | 2.31 | | 97.69 |

Figure 33.

Details of the blend formulations

| | | | 5 wt % loading | | | | | 1 wt % loading | | |
|---|---|---|---|---|---|---|---|---|---|---|
| | | | | Fixed wt % dry coating | | Fixed SAC (50% SAC) dry coating | | | Fixed wt % dry coating | | Fixed SAC (50% SAC) dry coating |
| | | Placebo | Uncoated | R972P | A200 | R972P | A200 | Uncoated | R972P | A200 | R972P |
| Coarse blends | API | 0 | 5 | 5 | 5 | 5 | 5 | 1 | 1 | 1 | 1 |
| | R972P | 0 | 0 | 0.116 | 0.000 | 0.058 | 0.000 | 0 | 0.000 | 0.000 | 0.012 |
| | A200 | 0 | 0 | 0.000 | 0.116 | 0.000 | 0.033 | 0 | 0.023 | 0.023 | 0.000 |
| | Avicel PH102 | 47 | 44.5 | 44.4 | 44.4 | 44.5 | 44.5 | 46.5 | 46.5 | 46.5 | 46.5 |
| | Pharmatose DCL11 | 47 | 44.5 | 44.4 | 44.4 | 44.5 | 44.5 | 46.5 | 46.5 | 46.5 | 46.5 |
| | Kollidon-CL | 5 | 5 | 5 | 5 | 5 | 5 | 5 | 5 | 5 | 5 |
| | MgSt | 1 | 1 | 1 | 1 | 1 | 1 | 1 | 1 | 1 | 1 |
| | Total wt% | 100 | 100 | 100 | 100 | 100 | 100 | 100 | 100 | 100 | 100 |

Figure 34.

Particle size distribution of the drug (Ibu10) particles after milling before and after the dry coating

| Dispersion methods | Compressed Air (1.0bar): Rodos | | | Gravity driven: Gradis | | |
|---|---|---|---|---|---|---|
| Sample Description (API only) | $d_{10}$ (μm) | $d_{50}$ (μm) | $d_{90}$ (μm) | $d_{10}$ (μm) | $d_{50}$ (μm) | $d_{90}$ (μm) |
| Uncoated Ibu10 | 4.2 ± 0.1 | 14.0 ± 0.2 | 35.4 ± 0.4 | 56.6 ± 9.9 | 1379 ± 550 | 2492 ± 558 |
| R972P fixed wt.% | 4.5 ± 0.0 | 12.4 ± 0.0 | 26.8 ± 0.2 | 16.2 ± 0.2 | 28.6 ± 0.2 | 46.0 ± 0.7 |
| A200 fixed wt.% | 4.9 ± 0.0 | 13.7 ± 0.1 | 30.3 ± 0.4 | 17.2 ± 0.2 | 29.8 ± 0.2 | 50.8 ± 0.6 |
| R972P fixed %SAC | 4.4 ± 0.0 | 14.1 ± 0.0 | 33.4 ± 0.1 | 25.9 ± 0.6 | 51.8 ± 6.0 | 382.0 ± 138.4 |
| A200 fixed %SAC | 4.4 ± 0.0 | 14.5 ± 0.2 | 35.0 ± 0.6 | 27.2 ± 0.6 | 59.9 ± 5.9 | 570.4 ± 47.8 |

Figure 35.

Selective cases of characteristic particle size distribution for 5 wt % loaded coarse and weakly cohesive blends at different mixing times

| Time (min) | Formulation | Coarse and weakly cohesive blends: 5 wt% loading ||||||
| | | Agglomerate PSD, Gradis ||| Primary PDS, Rodos (1.0bar) |||
| | | $d_{10}$ | $d_{50}$ | $d_{90}$ | $d_{10}$ | $d_{50}$ | $d_{90}$ |
|---|---|---|---|---|---|---|---|
| 5 | uncoated | 48.9± 1.4 | 132.3± 3.3 | 245.0± 7.8 | 14.2± 1.5 | 96.2± 1.1 | 215.6± 2.7 |
| | R972P fixed wt% | 45.5± 1.9 | 137.5± 6.7 | 265.8± 12.1 | 15.2± 0.8 | 95.8± 0.2 | 214.3± 3.3 |
| | A200 fixed wt% | 48.9± 3.6 | 142.7± 5.2 | 254.9± 10.4 | 15.2± 0.9 | 96.3± 0.5 | 214.3± 3.3 |
| | R972P fixed SAC% | 52.5± 0.4 | 144.1± 0.9 | 260.1± 9.3 | 15.2± 0.8 | 95.8± 0.4 | 211.0± 5.4 |
| | A200 fixed SAC% | 50.8± 2.3 | 140.8± 6.4 | 252.9± 10.3 | 15.2± 0.7 | 96.2± 0.5 | 213.2± 3.4 |
| 15 | uncoated | 47.6± 1.9 | 127.6± 2.9 | 242.3± 12.1 | 12.5± 0.8 | 85.7± 2.2 | 145.6± 0.4 |
| | R972P fixed wt% | 41.4± 0.5 | 124.7± 2.0 | 252.6± 11.8 | 12.7± 0.3 | 84.0± 0.5 | 145.1± 0.2 |
| | A200 fixed wt% | 44.0± 1.0 | 121.4± 2.7 | 249.5± 7.4 | 11.9± 0.1 | 81.2± 0.3 | 144.4± 0.1 |
| | R972P fixed SAC% | 25.4± 1.2 | 121.8± 1.1 | 249.9± 29.4 | 2.8± 0.1 | 88.0± 0.3 | 147.6± 0.0 |
| | A200 fixed SAC% | 35.4± 2.1 | 119.6± 3.6 | 237.2± 6.4 | 13.2± 0.6 | 86.2± 2.0 | 145.6± 0.6 |
| 30 | uncoated | 49.7± 1.7 | 122.7± 5.3 | 240.1± 9.3 | 12.8± 1.2 | 90.6± 0.8 | 146.8± 0.1 |
| | R972P fixed wt% | 35.6± 0.5 | 108.9± 1.2 | 223.0± 2.9 | 10.8± 0.5 | 87.9± 0.5 | 146.1± 0.2 |
| | A200 fixed wt% | 35.8± 0.8 | 106.9± 2.3 | 225.8± 10.9 | 12.1± 0.3 | 83.7± 0.5 | 145.2± 0.1 |
| | R972P fixed SAC% | 35.1± 1.3 | 107.9± 1.7 | 222.5± 4.8 | 12.2± 0.7 | 84.7± 0.9 | 145.3± 0.2 |
| | A200 fixed SAC% | 33.9± 0.3 | 105.8± 1.6 | 218.1± 3.7 | 11.9± 0.7 | 83.9± 2.8 | 145.2± 0.9 |
| 60 | uncoated | 53.2± 2.0 | 140.1± 10.6 | 754.5± 849 | 12.8± 1.2 | 90.6± 0.8 | 146.8± 0.1 |
| | R972P fixed wt% | 35.8± 1.1 | 113.1± 3.8 | 228.9± 4.1 | 10.8± 0.5 | 87.9± 0.5 | 146.1± 0.2 |
| | A200 fixed wt% | 36.1± 1.2 | 117.8± 3.9 | 235.6± 5.2 | 12.1± 0.3 | 83.7± 0.5 | 145.2± 0.1 |
| | R972P fixed SAC% | 36.1± 0.5 | 112.7± 3.3 | 228.2± 5.4 | 12.2± 0.7 | 85.0± 0.9 | 145.3± 0.2 |
| | A200 fixed SAC% | 37.3± 0.2 | 117.6± 1.1 | 233.4± 0.7 | 11.9± 0.7 | 83.9± 2.8 | 145.2± 0.9 |

Figure 36.

Selective cases of characteristic particle size distribution for 1 wt % loaded coarse and weakly cohesive blends at different mixing times Coarse and weakly cohesive blends: 1 wt% loading

| Time (min) | Formulation | Agglomerate PSD, Gradis | | | Span $\left(\frac{d_{90} - d_{10}}{d_{50}}\right)_{Gradis}$ | Primary PDS, Rodos (1.0bar) | | |
|---|---|---|---|---|---|---|---|---|
| | | $d_{10}$ | $d_{50}$ | $d_{90}$ | | $d_{10}$ | $d_{50}$ | $d_{90}$ |
| 5 | Uncoated | 53.5±1.2 | 131.3±3.8 | 263.2±23.4 | 1.6 | 24.4±0.6 | 108.0±0.5 | 226.3±3.7 |
| | R972P fixed %SAC | 52.6±1.3 | 131.4±4.0 | 265.6±26.2 | 1.6 | 29.5±1.0 | 112.8±2.7 | 220.6±7.5 |
| | A200 fixed wt % | 57.4±1.3 | 144.9±3.6 | 299.6±18.2 | 1.7 | 28.4±1.6 | 110.2±0.6 | 224.5±1.8 |
| 10 | Uncoated | 50.4±1.7 | 126.0±2.0 | 245.7±2.6 | 1.6 | 26.0±2.4 | 108.0±0.7 | 222.8±0.8 |
| | R972P fixed %SAC | 49.4±1.3 | 128.7±2.1 | 251.9±10.5 | 1.6 | 24.0±0.7 | 106.8±3.6 | 220.8±13.5 |
| | A200 fixed wt % | 54.0±11.6 | 126.0±6.3 | 236.5±23.7 | 1.4 | 24.6±0.3 | 108.9±0.9 | 231.3±4.9 |
| 15 | Uncoated | 51.0±7.5 | 140.6±16.3 | 772.0±891 | 1.8 | 23.7±0.7 | 108.5±1.2 | 227.6±3.3 |
| | R972P fixed %SAC | 50.7±0.7 | 129.6±2.6 | 259.7±20.4 | 1.6 | 23.7±0.7 | 107.6±0.4 | 227.1±3.4 |
| | A200 fixed wt % | 51.3±1.0 | 130.0±2.8 | 248.8±6.0 | 1.5 | 24.3±0.2 | 107.8±1.8 | 226.2±5.9 |
| 30 | Uncoated | 59.2±6.4 | 153.4±36.8 | 717.3±1016 | 4.3 | 27.7±0.3 | 107.5±0.8 | 220.0±3.3 |
| | R972P fixed %SAC | 55.3±2.4 | 139.2±7.1 | 274.2±31.7 | 1.6 | 29.2±0.8 | 110.4±1.4 | 224.2±4.9 |
| | A200 fixed wt % | 53.7±3.0 | 135.1±7.3 | 259.3±15.7 | 1.5 | 29.5±0.9 | 110.5±1.3 | 223.9±4.2 |
| 60 | Uncoated | 47.3±3.0 | 127.3±4.4 | 250.3±13.7 | 1.6 | 25.6±0.4 | 105.9±0.2 | 216.5±1.7 |
| | R972P fixed %SAC | 53.0±3.2 | 139.1±10.0 | 262.4±21.2 | 1.5 | 27.8±1.1 | 105.8±4.6 | 212.5±8.7 |
| | A200 fixed wt % | 53.3±4.2 | 140.1±8.5 | 265.9±17.2 | 1.5 | 26.7±0.7 | 105.8±2.4 | 214.5±3.7 |

Figure 37.

Bulk properties of the coarse and weakly cohesive blends of 5w% loading at different mixing times and dry coating formulations

| API loading | 5wt % | | | |
|---|---|---|---|---|
| Formulation | Mixing Time (min) | Bulk density (kg/m³) | Bulk cohesion (kPa) | FFC |
| uncoated | 5 | 0.42±0.01 | 0.19±0.01 | 7.3±0.3 |
| R972P fixed wt% | | 0.48±0.01 | 0.10±0.05 | 15.7±5.0 |
| A200 fixed wt% | | 0.42±0.01 | 0.31±0.06 | 4.9±0.8 |
| R972P fixed SAC% | | 0.47±0.01 | 0.08±0.05 | 23.2±0.4 |
| A200 fixed SAC% | | 0.46±0.02 | 0.25±0.04 | 5.8±0.1 |
| uncoated | 15 | 0.41±0.00 | 0.20±0.01 | 6.9±0.2 |
| R972P fixed wt% | | 0.48±0.00 | 0.08±0.03 | 19.7±2.4 |
| A200 fixed wt% | | 0.48±0.00 | 0.09±0.03 | 16.9±5.8 |
| R972P fixed SAC% | | 0.42±0.01 | 0.25±0.09 | 6.3±1.1 |
| A200 fixed SAC% | | 0.45±0.01 | 0.13±0.01 | 11.5±3.1 |
| uncoated | 30 | 0.44±0.01 | 0.61±0.04 | 2.2±0.2 |
| R972P fixed wt% | | 0.50±0.01 | 0.10±0.01 | 15.9±2.1 |
| A200 fixed wt% | | 0.49±0.00 | 0.21±0.01 | 7.8±1.4 |
| R972P fixed SAC% | | 0.48±0.00 | 0.17±0.04 | 9.2±0.1 |
| A200 fixed SAC% | | 0.47±0.00 | 0.19±0.01 | 8.0±0.2 |
| uncoated | 60 | 0.42±0.00 | 0.37±0.05 | 3.2±0.3 |
| R972P fixed wt% | | 0.50±0.00 | 0.08±0.07 | 24.3±7.6 |
| A200 fixed wt% | | 0.46±0.00 | 0.37±0.02 | 12.9±4.0 |
| R972P fixed SAC% | | 0.49±0.01 | 0.11±0.06 | 15.1±4.6 |
| A200 fixed SAC% | | 0.47±0.00 | 0.06±0.01 | 24.9±0.2 |

Figure 38.

Bulk properties of the coarse and weakly cohesive 1 wt% API loaded at different mixing times and dry coating formulations

| API loading | | 1 wt% | | |
|---|---|---|---|---|
| Formulation | Mixing time (min) | Bulk density (g/mL) | Bulk cohesion (kPa) | FFC |
| uncoated | 5 | 0.45±0.00 | 0.12±0.03 | 12.4±2.8 |
| R972P fixed % SAC | | 0.47±0.00 | 0.12±0.02 | 12.6±1.9 |
| A200 fixed wt % | | 0.45±0.01 | 0.10±0.04 | 15.5±4.0 |
| uncoated | 10 | 0.46±0.00 | 0.08±0.01 | 18.8±1.7 |
| R972P fixed % SAC | | 0.47±0.02 | 0.04±0.01 | 30.6±4.6 |
| A200 fixed wt % | | 0.46±0.00 | 0.11±0.00 | 13.2±0.4 |
| uncoated | 15 | 0.45±0.00 | 0.14±0.05 | 11.5±3.5 |
| R972P fixed % SAC | | 0.46±0.01 | 0.05±0.01 | 27.7±7.1 |
| A200 fixed wt % | | 0.45±0.00 | 0.08±0.02 | 18.1±3.4 |
| uncoated | 30 | 0.45±0.00 | 0.12±0.03 | 13.0±2.3 |
| R972P fixed % SAC | | 0.48±0.01 | 0.10±0.05 | 18.7±7.0 |
| A200 fixed wt % | | 0.47±0.02 | 0.07±0.02 | 21.1±5.6 |
| uncoated | 60 | 0.46±0.00 | 0.14±0.02 | 10.9±1.7 |
| R972P fixed % SAC | | 0.46±0.00 | 0.07±0.01 | 20.0±1.5 |
| A200 fixed wt % | | 0.47±0.00 | 0.09±0.02 | 16.1±4.2 |

Figure 39.

Details of blend formulations

| Fine blends | Placebo | 5 wt % loading ||||| 1 wt % loading |||
|---|---|---|---|---|---|---|---|---|---|
| | | Uncoated | Fixed wt % dry coating || Fixed SAC (50% SAC) dry coating || Uncoated | Fixed wt % dry coating | Fixed SAC (50% SAC) dry coating |
| | | | R972P | A200 | R972P | A200 | | A200 | R972P |
| API | 0 | 5 | 5 | 5 | 5 | 5 | 1 | 1 | 1 |
| R972P | 0 | 0 | 0.116 | 0.000 | 0.058 | 0.000 | 0 | 0.000 | 0.012 |
| A200 | 0 | 0 | 0.000 | 0.116 | 0.000 | 0.033 | 0 | 0.023 | 0.000 |
| Avicel PH105 | 47 | 44.5 | 44.4 | 44.4 | 44.5 | 44.5 | 46.5 | 46.5 | 46.5 |
| Pharmatose 450 | 47 | 44.5 | 44.4 | 44.4 | 44.5 | 44.5 | 46.5 | 46.5 | 46.5 |
| Kollidon-CL | 5 | 5 | 5 | 5 | 5 | 5 | 5 | 5 | 5 |
| MgSt | 1 | 1 | 1 | 1 | 1 | 1 | 1 | 1 | 1 |
| Total wt% | 100 | 100 | 100 | 100 | 100 | 100 | 100 | 100 | 100 |

Figure 40.

Selective cases of characteristic particle size distribution for 5 wt % loaded fine and cohesive blends at different mixing times

| Time (min) | Formulation | Fine and cohesive blends: 5 wt% loading ||||| |||
| | | Agglomerate PSD, Gradis ||| Span $\left(\frac{d_{90}-d_{10}}{d_{50}}\right)_{Gradis}$ | Primary PDS, Rodos (1.0bar) |||
| | | $d_{10}$ | $d_{50}$ | $d_{90}$ | | $d_{10}$ | $d_{50}$ | $d_{90}$ |
|---|---|---|---|---|---|---|---|---|
| 5 | uncoated | 24.0 ± 0.9 | 301.3 ± 111 | 1237 ± 543 | 4.0 | 3.3 ± 0.1 | 18.5 ± 0.1 | 46.7 ± 0.3 |
| | R972P fixed wt% | 22.7 ± 0.4 | 43.2 ± 1.9 | 90.3 ± 7.9 | 1.6 | 2.9 ± 0.3 | 18.7 ± 0.4 | 47.3 ± 0.2 |
| | A200 fixed wt% | 24.3 ± 1.3 | 47.5 ± 3.7 | 100.8 ± 3.3 | 1.6 | 3.6 ± 0.5 | 18.6 ± 0.1 | 47.6 ± 0.8 |
| | R972P fixed SAC% | 23.4 ± 0.8 | 45.6 ± 1.7 | 94.0 ± 11.1 | 1.6 | 3.3 ± 0.0 | 18.7 ± 0.0 | 47.5 ± 0.1 |
| | A200 fixed SAC% | 23.9 ± 0.8 | 48.4 ± 1.3 | 96.6 ± 8.0 | 1.5 | 3.1 ± 0.1 | 18.4 ± 0.2 | 47.1 ± 0.1 |
| 15 | uncoated | 24.1 ± 1.5 | 254.2 ± 185 | 808 ± 415 | 3.1 | 3.0 ± 0.0 | 19.0 ± 0.1 | 56.1 ± 0.2 |
| | R972P fixed wt% | 24.0 ± 2.7 | 48.7 ± 4.7 | 114.0 ± 13.1 | 1.8 | 3.3 ± 0.1 | 18.9 ± 0.2 | 49.4 ± 3.0 |
| | A200 fixed wt% | 21.6 ± 1.3 | 45.0 ± 4.0 | 110.1 ± 20.3 | 2.0 | 3.4 ± 0.0 | 19.1 ± 0.3 | 51.8 ± 3.3 |
| | R972P fixed SAC% | 23.2 ± 1.0 | 47.9 ± 3.1 | 126.5 ± 30.1 | 2.2 | 3.3 ± 0.1 | 19.0 ± 0.1 | 54.4 ± 0.3 |
| | A200 fixed SAC% | 22.6 ± 0.6 | 47.6 ± 2.1 | 103.8 ± 10.0 | 1.7 | 3.2 ± 0.1 | 18.8 ± 0.1 | 54.5 ± 0.7 |
| 30 | uncoated | 72.8 ± 68.6 | 706.9 ± 913 | 1683 ± 781 | 2.3 | 3.4 ± 0.1 | 18.3 ± 0.1 | 47.1 ± 0.1 |
| | R972P fixed wt% | 24.0 ± 2.6 | 62.1 ± 16.9 | 303.0 ± 158 | 4.5 | 3.5 ± 0.0 | 18.4 ± 0.0 | 47.0 ± 0.0 |
| | A200 fixed wt% | 24.0 ± 3.5 | 60.4 ± 22.4 | 228.7 ± 131 | 3.4 | 3.6 ± 0.1 | 18.3 ± 0.1 | 46.9 ± 0.2 |
| | R972P fixed SAC% | 26.4 ± 0.9 | 75.4 ± 10.1 | 1019 ± 708 | 13.2 | 3.6 ± 0.1 | 18.4 ± 0.1 | 47.1 ± 0.0 |
| | A200 fixed SAC% | 24.6 ± 10.0 | 63.3 ± 28.1 | 493.7 ± 364 | 7.4 | 3.6 ± 0.1 | 18.4 ± 0.1 | 47.2 ± 0.0 |
| 60 | uncoated | 33.0 ± 1.3 | 104.0 ± 4.4 | 1194 ± 903 | 11.2 | 3.5 ± 0.1 | 19.1 ± 0.1 | 54.2 ± 0.5 |
| | R972P fixed wt% | 24.1 ± 1.3 | 52.4 ± 5.4 | 113.7 ± 18.9 | 1.7 | 3.1 ± 0.0 | 18.8 ± 0.0 | 54.2 ± 0.2 |
| | A200 fixed wt% | 25.0 ± 0.9 | 62.4 ± 7.9 | 730 ± 845 | 11.3 | 3.2 ± 0.0 | 18.5 ± 0.2 | 49.6 ± 3.2 |
| | R972P fixed SAC% | 26.2 ± 0.4 | 67.8 ± 9.5 | 320.0 ± 167 | 4.3 | 3.3 ± 0.0 | 19.1 ± 0.3 | 51.8 ± 2.9 |
| | A200 fixed SAC% | 32.9 ± 1.5 | 98.4 ± 8.3 | 412.0 ± 53.0 | 3.9 | 3.4 ± 0.0 | 19.1 ± 0.3 | 51.4 ± 3.3 |

Figure 41.

Selective cases of characteristic particle size distribution for 1 wt % loaded fine and cohesive blends at different mixing times

| Time (min) | Formulation | Agglomerate PSD, Gradis | | | | Primary PDS, Rodos (1.0bar) | | |
|---|---|---|---|---|---|---|---|---|
| | | $d_{10}$ | $d_{50}$ | $d_{90}$ | Span $\left(\frac{d_{90}-d_{10}}{d_{50}}\right)_{Gradis}$ | $d_{10}$ | $d_{50}$ | $d_{90}$ |
| 5 | Uncoated | 41.7±2.6 | 734±128 | 1351±507 | 1.8 | 3.3±0.0 | 19.5±0.0 | 55.1±0.5 |
| | R972P fixed %SAC | 29.9±5.0 | 218±75 | 730±68 | 3.2 | 3.7±0.0 | 19.3±0.3 | 50.4±3.4 |
| | A200 fixed wt % | 24.0±2.6 | 196.1±53.7 | 914±208 | 4.5 | 3.9±0.0 | 19.9±0.0 | 55.1±0.2 |
| 10 | Uncoated | 40.8±12.9 | 896.2±444 | 1291±556 | 1.4 | 3.9±0.0 | 19.7±0.0 | 55.6±0.4 |
| | R972P fixed %SAC | 32.3±7.0 | 255.6±110 | 652±84 | 2.4 | 4.0±0.0 | 19.7±0.3 | 52.6±3.2 |
| | A200 fixed wt % | 32.7±6.8 | 377.6±168 | 994±117 | 2.5 | 3.9±0.0 | 19.6±0.3 | 52.5±3.1 |
| 15 | Uncoated | 48.4±7.8 | 952.6±343 | 1377±389 | 1.4 | 3.7±0.0 | 19.7±0.0 | 54.7±0.3 |
| | R972P fixed %SAC | 30.1±5.1 | 97.0±36.3 | 370.1±49.6 | 3.5 | 4.0±0.0 | 20.8±0.0 | 64.0±0.9 |
| | A200 fixed wt % | 30.8±5.3 | 111.5±52.1 | 429±73.0 | 3.6 | 3.3±0.0 | 18.9±0.0 | 47.8±0.1 |
| 30 | Uncoated | 26.3±6.1 | 293.7±484 | 1180±788 | 3.9 | 3.7±0.1 | 19.1±0.1 | 46.7±0.2 |
| | R972P fixed %SAC | 22.3±3.1 | 51.5±10.8 | 312.0±383 | 5.6 | 3.9±0.0 | 19.3±0.0 | 46.3±0.3 |
| | A200 fixed wt % | 20.6±0.8 | 50.1±7.6 | 411.8±413 | 7.8 | 3.9±0.0 | 19.2±0.0 | 46.5±0.2 |
| 60 | Uncoated | 28.6±9.7 | 536.7±382 | 951.0±682 | 1.7 | 3.6±0.0 | 19.5±0.0 | 53.0±0.3 |
| | R972P fixed %SAC | 29.6±9.0 | 96.7±47.7 | 307.7±65.3 | 2.9 | 3.9±0.0 | 19.7±0.0 | 53.3±0.2 |
| | A200 fixed wt % | 23.0±8.8 | 111.7±120.2 | 275.6±89.9 | 2.3 | 3.8±0.0 | 19.4±0.1 | 50.5±0.7 |

Figure 42.

Bulk properties of the fine and cohesive 5 wt% API loaded at different mixing times and dry coating formulations

| Formulation | Time (min) | Bulk density (kg/m³) | Fine and cohesive blends: 5 wt% loading | |
|---|---|---|---|---|
| | | | Bulk cohesion (kPa) | FFC |
| uncoated | 5 | 0.43± 0.00 | 0.50± 0.03 | 3.08± 0.09 |
| R972P fixed wt% | | 0.46± 0.01 | 0.38± 0.09 | 4.11± 1.19 |
| A200 fixed wt% | | 0.42± 0.01 | 0.41± 0.01 | 3.67± 0.73 |
| R972P fixed SAC% | | 0.44± 0.01 | 0.39± 0.12 | 4.01± 0.12 |
| A200 fixed SAC% | | 0.42± 0.01 | 0.42± 0.03 | 3.56± 0.07 |
| uncoated | 15 | 0.42± 0.00 | 0.44± 0.02 | 3.38± 0.15 |
| R972P fixed wt% | | 0.45± 0.01 | 0.33± 0.00 | 4.53± 0.26 |
| A200 fixed wt% | | 0.44± 0.00 | 0.47± 0.05 | 3.34± 0.04 |
| R972P fixed SAC% | | 0.46± 0.00 | 0.35± 0.02 | 4.15± 0.23 |
| A200 fixed SAC% | | 0.43± 0.00 | 0.35± 0.02 | 4.16± 0.33 |
| uncoated | 30 | 0.45± 0.01 | 0.63± 0.02 | 2.13± 0.15 |
| R972P fixed wt% | | 0.50± 0.01 | 0.29± 0.06 | 5.54± 1.09 |
| A200 fixed wt% | | 0.49± 0.00 | 0.24± 0.04 | 6.66± 1.51 |
| R972P fixed SAC% | | 0.42± 0.01 | 0.29± 0.07 | 5.19± 1.03 |
| A200 fixed SAC% | | 0.47± 0.00 | 0.30± 0.07 | 5.29± 0.85 |
| uncoated | 60 | 0.42± 0.01 | 0.45± 0.05 | 3.41± 0.22 |
| R972P fixed wt% | | 0.46± 0.00 | 0.31± 0.02 | 4.64± 0.10 |
| A200 fixed wt% | | 0.45± 0.01 | 0.28± 0.03 | 5.52± 0.29 |
| R972P fixed SAC% | | 0.46± 0.01 | 0.31± 0.00 | 4.62± 0.56 |
| A200 fixed SAC% | | 0.43± 0.00 | 0.41± 0.07 | 3.77± 0.68 |

Figure 43.

Bulk properties of the fine and cohesive 1 wt% API loaded at different mixing times and dry coating formulations

| Formulation | Time (min) | Fine and cohesive blends: 1 wt% loading | | |
|---|---|---|---|---|
| | | Bulk density (g/mL) | Bulk cohesion (kPa) | FFC |
| uncoated | 5 | 0.42± 0.00 | 0.46± 0.06 | 3.46± 0.37 |
| R972P fixed % SAC | | 0.41± 0.00 | 0.34± 0.05 | 4.60± 0.61 |
| A200 fixed wt % | | 0.41± 0.01 | 0.25± 0.07 | 6.45± 2.75 |
| uncoated | 10 | 0.39± 0.01 | 0.45± 0.04 | 3.41± 0.25 |
| R972P fixed % SAC | | 0.42± 0.00 | 0.35± 0.03 | 4.25± 0.30 |
| A200 fixed wt % | | 0.40± 0.01 | 0.23± 0.06 | 6.81± 2.60 |
| uncoated | 15 | 0.39± 0.00 | 0.43± 0.02 | 3.56± 0.11 |
| R972P fixed % SAC | | 0.39± 0.01 | 0.31± 0.06 | 4.84± 0.89 |
| A200 fixed wt % | | 0.41± 0.00 | 0.27± 0.03 | 5.63± 0.61 |
| uncoated | 30 | 0.44± 0.00 | 0.43± 0.01 | 3.73± 0.10 |
| R972P fixed % SAC | | 0.40± 0.01 | 0.22± 0.08 | 7.15± 1.80 |
| A200 fixed wt % | | 0.44± 0.00 | 0.18± 0.04 | 7.94± 1.34 |
| uncoated | 60 | 0.42± 0.00 | 0.39± 0.05 | 4.06± 0.39 |
| R972P fixed % SAC | | 0.42± 0.00 | 0.25± 0.09 | 6.32± 1.60 |
| A200 fixed wt % | | 0.41± 0.00 | 0.21± 0.07 | 8.38± 4.38 |

Figure 44.

Blend formulation details

| | Uncoated (%) | R972P 50% SAC (Dry coated) (%) |
|---|---|---|
| API (Ibu10) | 30.00 | 30.00 |
| Coating Material (R972P) | 0.00 | 0.37 |
| Avicel 105 | 32.00 | 32.08 |
| Lactose 450 | 32.00 | 32.08 |
| Crospovidone | 5.00 | 4.56 |
| MgSt | 1.00 | 0.91 |
| Total wt. % | 100 | 100 |

Figure 45.

The bulk density, cohesion and FFC of uncoated and dry coated blends (30% API loading) mixed for varying number of rotations. Placebo blend is included as a comparison (number of rotations, 750)

| API state | TIME | Number of rotations (Revolution) | Bulk density (g/mL) | Cohesion (kPa) | FFC |
|---|---|---|---|---|---|
| Uncoated | 4min 2sec | 125 | 0.45 ± 0.11 | 0.52 ± 0.02 | 3.24 ± 0.07 |
| | 8min 4sec | 250 | 0.37 ± 0.00 | 0.43 ± 0.02 | 3.54 ± 0.10 |
| | 12min 6sec | 375 | 0.38 ± 0.01 | 0.37 ± 0.02 | 4.10 ± 0.18 |
| | 16min 8sec | 500 | 0.34 ± 0.00 | 0.48 ± 0.01 | 3.60 ± 0.13 |
| | 24min 17sec | 750 | 0.39 ± 0.01 | 0.40 ± 0.02 | 3.87 ± 0.15 |
| | 32min 16sec | 1000 | 0.38 ± 0.00 | 0.41 ± 0.04 | 3.90 ± 0.25 |
| | 40min 19sec | 1250 | 0.38 ± 0.00 | 0.42 ± 0.06 | 3.92 ± 0.34 |
| | 48min 23sec | 1500 | 0.39 ± 0.00 | 0.43 ± 0.07 | 3.78 ± 0.44 |
| R972P 50% SAC coated | 4min 2sec | 125 | 0.44 ± 0.00 | 0.31 ± 0.02 | 4.69 ± 0.31 |
| | 8min 4sec | 250 | 0.44 ± 0.00 | 0.31 ± 0.06 | 5.45 ± 1.00 |
| | 12min 6sec | 375 | 0.45 ± 0.00 | 0.31 ± 0.09 | *(shaded)* |
| | 16min 8sec | 500 | 0.45 ± 0.00 | 0.21 ± 0.02 | *(shaded)* |
| | 24min 17sec | 750 | 0.46 ± 0.00 | 0.24 ± 0.02 | *(shaded)* |
| | 32min 16sec | 1000 | 0.47 ± 0.00 | 0.17 ± 0.02 | 8.57 ± 0.78 |
| | 40min 19sec | 1250 | 0.47 ± 0.01 | 0.19 ± 0.04 | 8.10 ± 1.52 |
| | 48min 23sec | 1500 | 0.46 ± 0.01 | 0.15 ± 0.02 | 9.83 ± 1.07 |
| Placebo | 24 min 17sec | 750 | 0.41 ± 0.00 | 0.43 ± 0.04 | 3.50 ± 0.22 |

*Potentially passable for the DC requirement*
*Passable for the DC requirement*

Figure 46.

Formulation of example 14.1 to example 14.8.

TABLE 21

| Example | Notation | Description | API | API (wt %) | Excipient I Host | Excipient I Guest (1 wt%) | Excipient I (wt %) | Excipient II | Excipient II (wt %) | Excipient III | Excipient III (wt %) |
|---|---|---|---|---|---|---|---|---|---|---|---|
| Ex 14.1 | CLF | Only uncoated Kollindon CL-F is included as excipient | Ibuprofen 50 | 95 | - | - | - | - | - | Kollidon CL-F | 5 |
| Ex 14.2 | CLF.A | Only dry coated Kollindon CL-F is included as excipient | Ibuprofen 50 | 95 | Kollidon CL-F | A200 | 5 | - | - | - | - |
| Ex 14.3 | LFP | Only uncoated HPC L-FP is included as excipient | Ibuprofen 50 | 95 | - | - | - | HPC L-FP | 5 | - | - |
| Ex 14.4 | LFP.A | Only dry coated HPC L-FP is included as excipient | Ibuprofen 50 | 95 | HPC L-FP | A200 | 5 | - | - | - | - |
| Ex 14.5 | LFP+CLF | Uncoated Kollindon CL-F and uncoated HPC L-FP are included as excipient | Ibuprofen 50 | 90 | - | - | - | HPC L-FP | 5 | Kollidon CL-F | 5 |
| Ex 14.6 | LFP.A+CLF | Uncoated Kollindon CL-F and dry coated HPC L-FP are included as excipient | Ibuprofen 50 | 90 | HPC L-FP | A200 | 5 | - | - | Kollidon CL-F | 5 |
| Ex 14.7 | SFP+CLF | Uncoated Kollindon CL-F and uncoated HPC SSL-SFP are included as excipient | Ibuprofen 50 | 90 | - | - | - | HPC SSL-SFP | 5 | Kollidon CL-F | 5 |
| Ex 14.8 | SPF.A+CLF | Uncoated Kollindon CL-F and dry coated HPC SSL-SFP are included as excipient | Ibuprofen 50 | 90 | HPC SSL-SFP | A200 | 5 | - | - | Kollidon CL-F | 5 |

Figure 47.

Formulation of example 16.1 and 16.2

| Example | Notation Description | API | API (wt %) | Excipient I Host (1 wt%) | Excipient I (wt %) | Excipient II | Excipient II | Excipient III | Excipient III (wt %) |
|---|---|---|---|---|---|---|---|---|---|
| Ex 16.1 | Av105+1%A200 Dry coated Avicel® 105 is included | Ibuprofen 70 | 60 | Avicel® 105 Guest A200 | 35 | Avicel® 105 | 5 | - | - |
| Ex 16.2 | Prosolv 50 included | Ibuprofen 70 | 60 | - | - | Avicel® 105 | 35 | Prosolv® 50 | 5 |
| Ex 16.3 | Av105 1%A200 Dry coated Avicel® 105 is included | Ibuprofen 70 | 60 | - | - | Avicel® 105 | 39.95 | A200 | 0.05 |

Figure 48.

The bulk density, cohesion and FFC of placebo blend and uncoated and dry coated blends at three different API loadings along with one case where silica was added instead of coated onto API

| API loading: | | 5% | | |
|---|---|---|---|---|
| API state | | Conditioned Bulk density (g/mL) | Cohesion (kPa) | Flow function coefficient, FFC (-) |
| | Uncoated | 0.43 ± 0.00 | 0.45 ± 0.04 | 3.30 ± 0.09 |
| | R972P fixed wt % coated (Minimized surface wettability) | 0.43 ± 0.01 | 0.21 ± 0.09 | 6.50 ± 0.69 |
| | A200 fixed wt % coated (Maximized surface wettability) | 0.43 ± 0.00 | 0.26 ± 0.03 | 5.70 ± 0.51 |
| | R972P fixed % SAC coated | 0.42 ± 0.00 | 0.26 ± 0.04 | 5.70 ± 0.80 |
| | A200 fixed % SAC coated | 0.43 ± 0.00 | 0.28 ± 0.13 | 5.70 ± 0.90 |
| Placebo, no API included | | 0.41 ± 0.00 | 0.43 ± 0.04 | 3.50 ± 0.22 |
| Blend of uncoated API at 5 wt % with added 0.116 wt % R972P silica (Fixed wt % case) | | 0.41 ± 0.01 | 0.37 ± 0.02 | 4.22 ± 0.18 |

\*\* *Grey shaded columns are the match columns for the comparison.*

Figure 49.

The bulk density, cohesion and FFC of uncoated and dry coated blends (30% API loading) mixed for varying number of rotations. Placebo blend is included as a comparison (number of rotations, 750)

| API state | TIME | Number of rotations (Revolution) | Bulk density (g/mL) | Cohesion (kPa) | FFC |
|---|---|---|---|---|---|
| Uncoated | 4min 2sec | 125 | 0.45 ± 0.11 | 0.52 ± 0.02 | 3.24 ± 0.07 |
| | 8min 4sec | 250 | 0.37 ± 0.00 | 0.43 ± 0.02 | 3.54 ± 0.10 |
| | 12min 6sec | 375 | 0.38 ± 0.01 | 0.37 ± 0.02 | 4.10 ± 0.18 |
| | 16min 8sec | 500 | 0.34 ± 0.00 | 0.48 ± 0.01 | 3.60 ± 0.13 |
| | 24min 17sec | 750 | 0.39 ± 0.01 | 0.40 ± 0.02 | 3.87 ± 0.15 |
| | 32min 16sec | 1000 | 0.38 ± 0.00 | 0.41 ± 0.04 | 3.90 ± 0.25 |
| | 40min 19sec | 1250 | 0.38 ± 0.00 | 0.42 ± 0.06 | 3.92 ± 0.34 |
| | 48min 23sec | 1500 | 0.39 ± 0.00 | 0.43 ± 0.07 | 3.78 ± 0.44 |
| R972P 50% SAC coated | 4min 2sec | 125 | 0.44 ± 0.00 | 0.31 ± 0.02 | 4.69 ± 0.31 |
| | 8min 4sec | 250 | 0.44 ± 0.00 | 0.31 ± 0.06 | 5.45 ± 1.00 |
| | 12min 6sec | 375 | 0.45 ± 0.00 | 0.31 ± 0.09 | |
| | 16min 8sec | 500 | 0.45 ± 0.00 | 0.21 ± 0.02 | |
| | 24min 17sec | 750 | 0.46 ± 0.00 | 0.24 ± 0.02 | |
| | 32min 16sec | 1000 | 0.47 ± 0.00 | 0.17 ± 0.02 | 8.57 ± 0.78 |
| | 40min 19sec | 1250 | 0.47 ± 0.01 | 0.19 ± 0.04 | 8.10 ± 1.52 |
| | 48min 23sec | 1500 | 0.46 ± 0.01 | 0.15 ± 0.02 | 9.83 ± 1.07 |
| Placebo | 24 min 17sec | 750 | 0.41 ± 0.00 | 0.43 ± 0.04 | 3.50 ± 0.22 |
| Physical mix (Identical composition as the R972P 50% SAC coated blend) | 4min 2sec | 125 | 0.43 ± 0.00 | 0.27 ± 0.02 | 5.48 ± 0.33 |
| | 16min 8sec | 500 | 0.42 ± 0.00 | 0.35 ± 0.02 | 4.45 ± 0.13 |
| | 24min 17sec | 750 | 0.47 ± 0.00 | 0.25 ± 0.02 | 5.96 ± 0.38 |
| | 48min 23sec | 1500 | 0.43 ± 0.01 | 0.24 ± 0.02 | 6.39 ± 0.59 |

*Potentially passable for the DC requirement*
*Passable for the DC requirement*

Figure 50.

POWDER BLEND PROCESSABILITY IMPROVEMENTS THROUGH MINIMAL AMOUNTS OF SYNERGISTICALLY SELECTED SURFACE COATING AGENTS

CROSS-REFERENCE TO RELATED APPLICATIONS

The present application claims the benefit of the filing date of U.S. Provisional Application No. 63/388,422 filed Jul. 12, 2022, the disclosure of which is hereby incorporated herein by reference.

GOVERNMENT STATEMENT

This invention was made with government support under contract grant number IIP-1919037, titled "PFI-RP: Commercializing innovations in design and manufacturing of fine pharmaceutical powders for cheaper and better medicines," and awarded by the National Science Foundation (NSF). The government has certain rights in the invention.

FIELD OF THE DISCLOSURE

The present disclosure relates to dry surface coated fine powder ingredients, and more particularly to active pharmaceutical ingredients (API), used in multi-component blends wherein a low amount of any one ingredient is dry coated, for example equal to or less than 5% wt, and methods of making the same for flow enhancement. The present disclosure also relates to any coated component of blends, including API and/or excipients, and more particularly to dry surface coating of binary or multi-component blends having low coated component loading of less than 10% wt, and methods of making the same.

BACKGROUND

Drug products such as compressed tablets, filled capsules or sachets, require blends, which include drug and excipients, which have desired quality attributes, such as adequate flowability, bulk density, and drug content uniformity, to name a few. Amongst those, flowability is a critical factor that is an indicator of successful manufacturing and product quality of tablets (Sun C C. Setting the bar for powder flow properties in successful high speed tableting. Powder Technology. 2010; 201(1):106-108), capsules (Tan, S. and J. Newton, Powder flowability as an indication of capsule filling performance. International Journal of Pharmaceutics, 1990. 61(1-2): p. 145-155), and powder filled sachet (Pitt K. Formulation and processing for powder sachets. In: Tovey G D, editor. Specialized pharmaceutical formulation: Royal Society of Chemistry; 2022. p. 338).

As micronized, finer sized, e.g., 30 μm and lower, drug powders are increasingly being used for assorted reasons including improved drug dissolution, achieving desired blend properties gets more challenging. Even the use of well flowing or specialized excipients, e.g., silicified MCC has been found to be insufficient in imparting such desired qualities (L. Chen, S. Fan, Z. He, X. Ding, K. T. Kunnath, K. Zheng, R. N. Davé, Surface engineered excipients: III. Facilitating direct compaction tableting of binary blends containing fine cohesive poorly compactable APIs, International Journal of Pharmaceutics, 557, pp. 354-365, 2019). Besides, the use of well-flowing excipients, which tend to be coarser in size along with finer drug powders is likely to promote downstream segregation of APIs and excipients.

There are several approaches to improving flowability and bulk density of such blends such as dry granulation and wet granulation to name a few. Such technologies have proved to be successful only for specific drugs and drug loadings of an active pharmaceutical ingredient (API). In addition there are many disadvantages to using the current techniques of dry and wet granulation including but not limited to additional equipment required and added manufacturing expense due to the additional steps in these processes.

Granulation, the process of particle enlargement by agglomeration technique, is one of the most significant unit operations in the production of pharmaceutical dosage forms, mostly tablets and capsules. Granulation process transforms fine powders into free-flowing, dust-free granules that are easy to compress. Nevertheless, granulation poses numerous challenges due to high quality requirement of the formed granules in terms of content uniformity and physicochemical properties such as granule size, bulk density, porosity, hardness, moisture, compressibility, and the like together with physical and chemical stability of the drug. Typical granulation process can be divided into two types: wet granulation that utilize a liquid in the process and dry granulation that requires no liquid. The type of process selection requires thorough knowledge of physicochemical properties of the drug, excipients, required flow and release properties as well as other properties.

Further, techniques such as wet granulation, which consists of multiple steps and use of liquids, are unsuitable for numerous APIs because of their tendency for degradation in presence of liquids or binders as well as heat during drying. Techniques such as dry granulation may also have certain limitations and may not work. For example, when the drug loading is outside the range between 20-60%. In addition, when more than one API or multiple component APIs are used, the tableting process becomes more complicated and has increased failures in making a tablet.

In the prior art technologies, silicas (silicon dioxide) are used in the pharmaceutical formulation (for example as glidants, as anti-caking agents, and as adsorbents) for potentially enhancing the blend flowability. For most such usage, the amount of silica typically ranges from 0.25 to 2.00 wt % of the blend. The lower values of this range are usually insufficient for flow enhancement for the blends with finer APIs and the higher values of this range may have adverse impacts such as uneven distribution of silica, potential separation of silica in the downstream processing, or variability of ensuing flow properties including reduction in the bulk density. In numerous prior art examples, it has been shows that direct addition of silica within the blend does not provide the required blend property enhancements, see for example; Improved blend and tablet properties of fine pharmaceutical powders via dry particle coating, Z. Huang, J. V. Scicolone, X. Han, R. N. Davé, (2015) International Journal of Pharmaceutics, Vol. 478(2) p 447-455.

The above cited prior art and others, for example, "Improved properties of fine active pharmaceutical ingredient powder blends and tablets at high drug loading via dry particle coating"; K. Kunnath, Z. Huang, L. Chen, K. Zheng, R. Davé, (2018), International Journal of Pharmaceutics, 543(1-2), pp. 288-299 have addressed enhancement of flow properties of blends and in some cases, compaction properties of blends by dry coating the API powder with silica for API loadings ranging from 10 to 60 wt % and using adequate amounts of silica. However, as discussed herein, the above article did not consider either exceptionally low API loading or exceptionally low amounts of silica. Besides, for higher drug loading cases, the entire amount of API in the formulation had to be dry coated, hence requiring significant amount of processing and higher amounts of silica.

Indeed, current technologies require additional process steps in generating tablets that contain low amounts of API and/or have fine particle sizes and/or have multicomponents. Such additional steps generate quality issues due to reproducibility and increase manufacturing costs. Compaction properties such as tensile strength of the tablet suffer as agents are added to the pharmaceutical blend to increase flowability for better tablet processing. It is generally known and accepted in the art that as the flow properties increase for a pharmaceutical blend having fine particles or nanoparticles then the tensile strength of the tablet significantly decreases making the tablet process more difficult.

The use of flow promoting agents such as silica by itself does not lead to improved blend compaction properties. Examples are shown where dry blending of the similar ingredients does not lead to improved compaction properties as compared to the same ingredients that undergo wet granulation type processes that create intimate contact between microcrystalline cellulose (MCC) and silica. The addition of silica may reduce the free surface energy of the mixture because, in most cases, silica has lower surface energy than the excipient. However, the presence of silica can lead to inferior compaction properties since lower surface energy leads to weaker tablets. For example, in Fichtner, F., et al., "Effect of surface energy on powder compactability," Pharmaceutical Research 25, 2750-2759 (2008), the article showed a decrease in tablet strength correlated to the decrease in powder surface energy at constant tablet porosities.

Thus, dry processing of an ordinary excipient with silica is not expected to lead to improved tablet compaction properties, even though the flow may be enhanced because of silica.

Overall, the prior efforts have attempted to disclose various aspects of better compacting excipients that include silica, surfactant, and other materials, they have not shown how dry processing can lead to better blends or better compacting individual excipients. Rather, it has been demonstrated that dry blending did not provide improved compaction properties, see for example, Chattoraj, S., et al., "Profoundly improving flow properties of a cohesive cellulose powder by surface coating with nano-silica through co-milling," Journal of Pharmaceutical Sciences 100, 4943-4952 (2011); and Zhou, Q., et al., "Preparation and Characterization of Surface-Engineered Coarse Microcrystalline Cellulose Through Dry Coating with Silica Nanoparticles," Journal of Pharmaceutical Sciences, 101:4258-4266 (2012). It was shown by these authors that dry coating of silica on fine (Avicel® 105), and coarse (Avicel 102) excipients may be achieved using many passes of a conical milling device, e.g., comil.

It was shown by the present inventors that dry coating of silica on fine (Avicel® 105), and coarse (Avicel 102) excipients may be achieved using one or two passes of a conical milling device, e.g., comil, if silica and excipient were pre-blended in a conventional mixer such as the V-blender prior to running through a comil. The resulting product from either approach was found to have enhanced flow. These dry coated excipients, however, produced weaker 100% MCC placebo tablets, although the tablet strength was found to be still acceptable for Avicel 105 as long as sufficiently high compaction force was used. However, this prior art did not consider or report tablet compaction using pharmaceutical blends of API and/or low loading API and/or dry coated excipients. It also did not examine the impact on the other solid dosage form production, such as filling of capsules and sachets.

Overwhelmingly, the prior art suggests that dry coating will lead to poorer compaction properties because it is likely to lead to reduced surface energy after dry coating (Sun, C., "Decoding Powder Tabletability: Roles of Particle Adhesion and Plasticity," Journal of Adhesion Science and Technology, 25:483-499 (2011); Fichtner, et al. 2008; Etzler, F. M., et al., Tablet tensile strength: An adhesion science perspective. Journal of Adhesion Science and Technology 25, 501-519 (2011); and Han, X., et al., Passivation of high-surface-energy sites of milled ibuprofen crystals via dry coating for reduced cohesion and improved flowability. Journal of Pharmaceutical Sciences 102, 2282-2296 (2013)).

The blends of dry coated excipients with poorly flowing and poorly compacting APIs, particularly for very high or very low API loadings, are expected to have inadequate compaction properties required for high quality tablets, and formation of plug or densification via tapping required for capsule formation would also be adversely impacted. Likewise, filling sachets is also expected to be challenging for blends of poorly flowing and compacting APIs.

Some prior attempts are seen in US 2018/0055775A1 and U.S. Pat. No. 10,751,288B2. These documents focus on the improvements in the powder flowability and compressibility in blends where one of the excipient components was dry coated. However, for the binary blends, comprised of micronized and cohesive active pharmaceutical ingredient (API) with the surface engineered excipient, the lowest amount of dry coated component was 40 wt %. For that case, the amount of nano-sized fumed silica (Acrosil®) used in the formulation ranged from 0.5 to 1.00 wt %. Based on the results shown in these documents in which as the amount of dry coated component decreased, the flowability enhancements diminished. Therefore, reducing the dry coated component and hence the total amount of silica would be expected to continue to exhibit significant undesired decrease in level of flowability enhancements.

In Huang, Z., J. V. Scicolone, X. Han and R. N. Davé (2015), "Improved blend and tablet properties of fine pharmaceutical powders via dry particle coating," International Journal of Pharmaceutics 478(2) 447-455, multi-component blends of micronized acetaminophen (~10 microns size) with either fine (~20 microns) or conventional, coarse (~100+ microns) excipients was researched. The drug/API loads considered were 10, 30 and 60 wt % hence in the lowest component of dry coated components was 10 wt %, and the lowest amount of silica in the blend was 0.26 wt %. Unfortunately, for that embodiment, the flow function coefficient (FFC) enhancement due to coating of the API was not adequate, i.e., FFC of about 5, to promote direct compaction, capsule, and sachet filling with reduced segregation tendency.

The flowability of solids may be classified according to shear-testing based assessment of the flow function coefficient (FFC), which is the ratio of the consolidation pressure or stress ($\sigma 1$) divided by the cohesive strength (fc) or flow function or flow factor (FF) values. It is generally accepted that very cohesive and non-flowing solids, granules, powders, and the like have a FFC less than 2. Cohesive is defined as having a FFC greater than 2 and less than 4. An easy flowing solids, granules, powders, and the like have a FFC greater than 4 and less than 10. And free flowing is defined as having a FFC greater than 10. (See, Andrew Jenike, Storage and flow of solids, Bulletin 123 of Utah Engineering Experiment Station, Vol. 53, No. 26, November 1964).

In Huang, Z., J. V. Scicolone, X. Han and R. N. Davé (2015), "Improved blend and tablet properties of fine pharmaceutical powders via dry particle coating," International Journal of Pharmaceutics 478(2) 447-455, multi-component blends of micronized acetaminophen (~10 microns size) with either fine (~20 microns) or conventional, coarse (~100+ microns) excipients was researched. The drug/API loads considered were 10, 30 and 60 wt % hence in the lowest component of dry coated components was 10 wt %, and the lowest amount of silica in the blend was 0.26 wt %. Unfortunately, for that embodiment, when the blend utilized fine excipients, the flow function coefficient (FFC) enhancement due to coating of the API was not adequate, i.e., FFC of about 5, to promote direct compaction, capsule, and sachet filling with reduced segregation tendency.

However, FFC improved to almost 7 for the embodiment where the dry coated component was at 30 wt %, and the amount of silica in the blend was 0.78 wt %. A FFC of over 8 was achieved for the embodiment where the dry coated component was at 60 wt %, and the amount of silica in the blend was 1.57 wt %. The best FFC enhancements occurred for the case where the API loading was 10 wt % but all the fine components including the API and excipients were dry coated, amounting to excessive burden to carry out dry coating and the amount of silica in the blend to be well above 1 wt %. These results suggested that the trend for flowability enhancements favor increasing of the dry coated component such as the API and as silica increased significantly to over 1 wt % of the blend. Discouragingly, these prior art results further show a reduction in silica amounts along with the percentage of dry coated API component will result in decreased FCC.

In Huang, Z., W. Xiong, K. Kunnath, S. Bhaumik, and R. N. Davé (2017), "Improving blend content uniformity via dry particle coating of micronized drug powders." European Journal of Pharmaceutical Sciences 104: 344-355, reported was a study of the binary blend which was comprised of the dry coated minor component in the amounts equivalent to 3, 5, or 10 weight percent of a cohesive API (with or without dry coating) and the Avicel PH102. The purpose of the work was to demonstrate if dry coating of the API would improve the drug content uniformity and not the flowability or processability of the blend. Huang et al. used a binary blend instead of more pharmaceutically relevant multi-component blends that offer additional challenges in processability.

In Kunnath, K., Z. Huang, L. Chen, K. Zheng, and R. Davé (2018). "Improved properties of fine active pharmaceutical ingredient powder blends and tablets at high drug loading via dry particle coating." International Journal of Pharmaceutics 543(1-2): 288-299, considered was additional cases of APIs to assess the repeatability of the prior-art publication that only included a single API test-case. Kunnath et al. 2018 investigated multi-component pharmaceutical powder blend at high loadings or 60 weight percent API loading for assessing blend's flowability and bulk density change due to the dry coated APIs with 1 wt % of either hydrophobic or hydrophilic silica. While the property enhancements reported were adequate, the paper focused only on high dry loading of 60 wt %, hence the dry coated component in the blend was high, at 60 wt %, and correspondingly, the silica was 0.6 wt % of the total blend.

In Kim, S., E. Bilgili and R. N. Davé (2021), "Impact of altered hydrophobicity and reduced agglomeration on dissolution of micronized poorly water-soluble drug powders after dry coating." International Journal of Pharmaceutics 606 reported was the competition between the increase in the surface hydrophobicity and decrease in the agglomerate size on the dissolution rate of the poorly water-soluble API without forming a blend. Researched was the examination of properties of the API with and without dry coating, and hence the dry coated constituent was 100%, and the lowest silica amount was 0.28 wt %. Multicompetent APIs were not investigated as well as low loading APIs of less than 5 wt %. The prior research indicated that low loading and low use of silica would not be favored for direct tabulation, and other processing would be needed. Interestingly, this work pointed out that the flowability and natural agglomeration of fine powders are inversely correlated, implying improved flowability may also be associated with reduced agglomeration, which could be a quick indicator of the fine powder cohesivity.

Osorio and Muzzio (2013), "Effects of powder flow properties on capsule filling weight uniformity" Drug Development and Industrial Pharmacy 39(9): 1464-1475, noted that for the optimal encapsulation, powder blends or single component powders must have the right flowability and bulk density. They concluded that "the better the flow, the higher the weight and the lower the variability for such as capsule filling system." These properties become even more critical as the API loading is reduced as they affect the product's homogeneity. The paper also mentioned that while a single measure of flowability may be insufficient to discern various powder blends cases, overall, better flowability and bulk density ensure processability and product quality for capsules. However, this paper did not discuss reliable methods to enhance blend properties.

Thus, there remains a need in the art to address the significant problems faced by formulators in pharmaceutical, nutraceutical and other industries that deal with preparing multi-constituent blends of active ingredient mixed with other functional materials. For example, in pharmaceutical industry, this requires significant amount of development time, materials, and effort for developing blends to form tablet, capsule or sachet formulations that exhibit desirable properties such as flowability, bulk packing density, compressibility or compactability, blend content uniformity, as well as dissolution from the API powders, without having to resort to granulation, especially wet granulation that consists of multiple steps and use of liquids.

This problem is even more challenging for multicomponent APIs when the APIs are fine sized powders, ranging from 10 to 70 micron, usually further categorized as fine (10-15 micron) or semi-fine (30-50 micron) with low (less than about 5 wt %) active pharmaceutical ingredient (API) loading. While it is well known that when the blend includes flow aids such as fumed silica, the blend properties such as flowability can be improved. Unfortunately, the improvements by simply adding the silica during blending are not adequate as compared to those achieved if the silica was indeed dry coated, see for example Huang, Z., J. V. Scicolone, X. Han and R. N. Davé (2015), "Improved blend and tablet properties of fine pharmaceutical powders via dry particle coating," International Journal of Pharmaceutics 478(2) 447-455.

The problem remains challenging even for the very high drug loading formulations since a large amount of API powder must be dry coated. For example, a 100 Kg batch would require dry coating of 600 Kg fine API for a 60 wt % drug loaded formulation such as that discussed by Huang, Z., J. V. Scicolone, X. Han and R. N. Davé (2015), "Improved blend and tablet properties of fine pharmaceutical powders via dry particle coating," International Journal of Pharmaceutics 478(2) 447-455. Handling such large quantities per batch for a specialized processing step like dry coating also poses practical challenges. Therefore, it would be beneficial to be able to dry coat only a smaller portion of the batch and yet achieve adequate flow enhancements. For example, what if only 50 Kg of API were to be dry coated instead of 600 Kg in this example, yet achieve adequate flow for the final blend, where the total amount of silica used would be reduced by 10 times.

Current art does not provide such approaches and hence for nano-sized additives such as silica when dry coated on APIs, some of these properties could be improved, but require high silica amounts, e.g., over 1 wt % of the blend, and also require dry coating of very large amounts of material per batch while making tablet formation difficult. Further, it remains a challenge to achieve simultaneous improvements in all such properties while using lesser amounts of silica and when the APIs (or active ingredients in other industry applications) are fine.

SUMMARY OF THE INVENTION

The present invention overcomes the drawbacks of previous attempts and provides additional benefits. Specifically the composition and method concerns significant synergistic enhancement of desirable critical properties, such as the powder or blend flowability, bulk packing density, blend uniformity, compactability, or drug dissolution, of multicomponent blends of fine powders through solventless dry mechanical coating of at least one selected minor component that is surface coated with nano-sized powders in exceedingly lesser amounts by wt % of the blend. In some embodiments the multicomponent blend includes at least three individual components that make up the API-based formulation and all or a small portion of any one of the fine constituents may be dry coated, not exceeding 10 wt % and preferably no more than 10 wt %, followed by blending with the rest of the constituents using conventional powder mixers. In some embodiments, a small amount of a single powder constituent, such as the fine API powder, not exceeding 10 wt % and preferably no more than 10 wt %, is dry coated followed by blending with the rest of the single constituent. Thus the need is eliminated to dry coat the entire fine powder sample.

This present disclosed method and formulation is highly advantageous because dry coating is an environmentally benign process that does not require use of liquids and additional steps and such blends lead to simple dry mixing to form compressed tablets, filled capsules and sachets. Further, the disclosed formulation and method reduce the need for dry coating the majority or the entirety of ingredients, hence reducing the processing burden. In one aspect, in a multicomponent API blend having more than three components, and preferably at least 5 components, one or more components together as low as 1-5 wt % were dry coated keeping silica concentration in the blend in the range of 0.116 to 0.007 wt %.

Surprisingly it was found that there is a synergy in flow enhancement (FFC is increased) along with counter-intuitive results of dissolution and tensile strength (both dissolution and tensile strength increased) when the API loading is high, e.g. 10%-50% or API is low, e.g. less than 5% and 5%-10% of the minority component in either case is dry coated as further described herein. The present invention utilizes a relatively low amount of silica dry coated (and not wet granulation or dry granulation techniques) on a minority component that results in an API blend of surprisingly high FFC values as well as unexpected high tensile strength and dissolution properties. A "minority" component for the purposes of this specification is defined as for a binary or at least a two component API blend the component that has less than 50% by weight volume, or for a single constituent, a minority fraction of material selected and processed for dry coating. In blends that have more than two API components, the minority component is the API with the least amount of weight per volume or a part thereof. Prior-art examples show that typically the majority component would need to be dry coated and not the minority component, or at the least, the entire minority component, equal to or exceeding 10 wt %. An average FFC calculated for the blend constituents including the dry coated minority component showed an expected low FFC.

However as shown herein, a high FFC resulted when the minority component was coated. This surprising result also occurred when the excipient was dry coated as a minority component instead of the API. It is within the scope of the invention to dry coat the minority component whether it is an API, an excipient, or dry coating both the API and the excipient together so long as it is a minority component.

Depending on the implementation, the APIs or excipients may be different or all the same at different concentrations. The current prior art failed approaches to enhance critical blend properties involve employing of dry granulation or wet granulation that are multi-step processes, or use of excessive amounts of silica additives to promote just one or two properties. In contrast, the novel formulation taught by this invention leads to surprising outcomes for simultaneous enhancements of all such desirable properties, facilitating formulation design, product manufacturing, product quality, and patient experience. Such advantages are also expected in other applications involving the use of fine constituents.

Dry coating of a minor component in a blend, including a minor fraction of the component if it is not a minor component, improves upon these deficiencies of the prior art and surprisingly, it is found that dry coating does not have detrimental effect on tablet strength of blends of cohesive APIs at low drug loadings (less than 5 wt % such as 1, 3 or 5 wt %) that have multicomponent APIs, and APIs with fine particle size. For purposes of this disclosure fine particle size is defined as active ingredients, ranging from 10 to 70 microns, and further categorized as fine (10-15 micron) or semi-fine (30-50 micron) with low (less than about 5 wt %) active pharmaceutical ingredient (API) loading.

The use of the silica in the present disclosure has a simplified manufacturing scheme and minimal use of silica or other flow promoting agents. Accordingly, dry coated excipients can be produced by a manufacturing process that does not require the use of any liquids via simultaneous milling and dry coating. Dry coated excipients can also advantageously be used to form cohesive API blends by direct compression or roller compaction without the need for wet granulation. In addition, such practice will simplify the manufacturing processes for filling capsules and sachets.

The dry coating in the current invention addresses the use of minor components in the more challenging cases of multi-component blends, where the dry coated component is at the most at 5 wt %, and more remarkably, silica concentration in the entire blend is in the range of 0.116 to 0.007 wt %. Even at this low silica concentration, it presents remarkable flowability and density improvement, beyond the flowability range described in the prior patents.

The current invention tackled the challenges associated with poor flowability and processability of API blends that adversely impact quality of products such as tablets, capsules, or filled sachets by investigating the improved multicomponent (e.g., in some embodiments five (5) API components) blend uniformity, including the case of much lower API (hence the dry coated component being even lower) content of 1 wt %. In such cases, attaining acceptable blend uniformity is more challenging. The results in the current invention are due to unknown and unexpected synergy between the minute amounts of additives such as flow-aids, including silica (nanoparticle) used as the dry coating agent on the surface of a minor component of the total blend, which is later mixed with other blend components. Although in the current art, representative hydrophilic or hydrophobic nano-sized fumed silica were selected as the dry coating agent, the dry coating agents are not limited to those, and could also include materials that tend to smear under mixing shear, for example, magnesium stearate (MgSt), Leucine, stearic acid, or a surfactant, such as Sodium Lauryl Sulfate (SLS) also known as Sodium Dodecyl Sulfate (SDS). The above materials also categorized as flow aids may also be used alone or in any combination depending on the embodiment.

Other exemplary materials include nanoparticles of alumina, titania, carbon black, aluminum calcium silicate, calcium silicate, magnesium silicate, potassium silicate, sodium silicate, sodium aluminosilicate, sodium calcium aluminosilicate, tricalcium silicate, silica aerogel, talc, iron oxide, other metal oxides and mixtures thereof. The nanoparticle may have a particle size in the range of 2-50 nm and more preferably about 7 to 20 nm. Preferably, the materials to be used have dispersive surface energy low enough as compared to the surface energy of the host, which could be either API or one or the other excipient core particles so that the nanoparticles can be deagglomerated and easily spread and coated over the host core particles. In the examples provided here, the synergy between the dry coating and subsequent blending or mixing processes caused the unexpected blend properties enhancements. Similar enhancements are expected for other types of additive materials.

The silica particles used in the present invention may be of any type, such as hydrophobic treated silica or fumed silica. Examples of suitable silicas include Acrosil R972 silica (Evonik), CAB-O-SIL EH-5 silica (Cabot), CAB-O-SIL M-5P silica (Cabot), CAB-O-SIL M-5DP silica (Cabot), AEROSIL® 200 Pharma (Evonik), AEROSIL® 300 Pharma (Evonik), AEROPERL® 300 Pharma (Evonik), OX-50 silica (Evonik), and TS530 silica (Cabot). In general, preferred are the fumed amorphous silicas with a specific surface area of greater than about 100 $m^2/g$. Hydrophobic silica may be obtained by hydrophobic treatment. In one embodiment, the hydrophobic treatment of hydrophilic silica may be accomplished by treating the hydrophilic silica with dichlorodimethanolsilane. Any other suitable methods known to a skilled person that are capable of modifying silica to hydrophobic silica may be used. Hydrophobic silica, in addition to improving flow and bulk density properties, may aid in improved dispersion of the coated API and greatly reducing the size of agglomerated API particles, aiding in their faster release.

In some embodiments, the silica comprises hydrophilic silica having a specific surface area ranging from about 175 $m^2/g$ to about 300 $m^2/g$.

In some embodiments, the silica comprises a functionalized hydrophobic having a specific surface area ranging from about 90 $m^2/g$ to about 130 $m^2/g$.

In some embodiments, the API or the selected minor component of the blend has a bulk density ranging from about 0.05 g/mL to 0.5 g/mL and a flow function coefficient (FFC) ranging from about 1.0 to 3.5.

In some embodiments, the API or the selected minor component of the blend is present in an amount ranging from about 0.1 wt % to about less than 5%, based on the total weight of the pharmaceutical blend.

In some embodiments, a flow function coefficient (FFC) of the dry coated pharmaceutical ranges from 3 to 30.

In some embodiments, the bulk density of the pharmaceutical blend ranges from about 0.2 g/mL to about 0.99 g/mL.

In some embodiments, the flowability of the pharmaceutical blend ranges from about 2 to about 30.

In some embodiments, the silica has a particles size ranging from about 10 to about 50 nanometers and is present in an amount of about 0.01 wt % to about 1 wt %, based on the total weight of the pharmaceutical.

In some embodiments, a pharmaceutical tablet is made from the blend, the tablet having a porosity ranging from about 0.05 to about 0.35 and a tensile strength ranging from about 1 MPa to about 10 MPa.

In some embodiments, a method of forming a pharmaceutical tablet includes compressing a multicomponent blend of an API or the selected minor component of the blend that is dry coated with a silica to directly compress the blend into a pharmaceutical tablet, wherein the method does not include a wet granulation step.

In some embodiments, a pharmaceutical capsule is made from the blend, the capsule of size 1 is filled with blend weight ranging from about 250 mg to about 400 mg and its weight variation under 5%.

In some embodiments, a method of filling a pharmaceutical capsule includes using a dosator to compress a plug of a multicomponent blend of an API that is dry coated with a silica, wherein the method does not include a wet granulation step.

In another aspect, using a material sparing high-intensity vibrational mixer, one of the minor components within a multi-component blend which contains more than three components was dry coated with the 2.31 to 1 wt % of either Aerosil R972P or Aerosil 200, hence resulting in the silica amount of only 0.023 to 0.01 wt % in the multi-component blend. The coating materials were selected based on the surface energy differentials in the API and silica.

Depending on the implementation of the current invention, finer sized silica is preferred as defined herein. The flowability, bulk density, API release rate, and compaction strength were remarkably improved unexpectedly even at such a low silica concentration. For example, for cohesive and fine multi-components (three to five components), the flowability improved up to 100%, resulting in the flow regime shift from cohesive to easy flowing. Likewise, the bulk density was improved, and remarkably, the compaction properties also surprisingly improved even in presence of silica.

Most impressively, using the current invention for five components blend, the drug dissolution rate was significantly improved as compared to the untreated five components blend. Current approaches involve employing of dry or wet granulation and multi-step processes to enhance one or two of the desirable blend properties such as blend flowability, bulk packing density, blend uniformity, compaction, or drug dissolution. The challenges are more significant for the blends that have fine powders. Further, current approaches may also require use of significant amounts of additives to promote one or more properties.

In contrast, the novel formulation of the current invention and approach leads to surprising synergistic results for simultaneous enhancements of all such desirable properties, facilitating formulation design, product manufacturing, product quality, and patient experience. Such advantages are also expected in other applications involving the use of fine constituents. The flexibility and variations in the invention arise from the synergy during blending as the additives such as nano silica are coated via any method on to one of the fine powder ingredients, including the smaller fraction of the same ingredient.

In another aspect, dry coating on a reduced multicomponent active pharmaceutical ingredient (API) agglomeration is disclosed herein. Fine cohesive API agglomeration through dry coating was shown to enhance uniformity and processability of multi-component blends at low (1, 3, or 5 wt %) API loadings. Dry coating with two distinct types/amounts of silica was systematically assessed of fine milled ibuprofen (~10 µm). Dry coated ibuprofen powders exhibited dramatic agglomeration reduction, decreased cohesion, unconfined yield strength, and improved flowability attributed to nano-scale surface morphology imparted by silica coating. Blends exhibited profound enhancement in flowability/bulk density at above low API loadings. Hydrophobic silica coating improved drug dissolution rate without appreciably reducing tablet tensile strength. Dry coating all three low drug loading APIs improved blend uniformity and tablet dissolution due to agglomerate size reduction. Blend flowability, bulk density, and blend processability were improved without adverse impact on tablet compaction. Although these examples illustrate objects and advantages of the present invention for a poorly water-soluble drug ibuprofen, which is a BCS (biopharmaceutical classification system) Class II drug, it is applicable to other such cases, including fenofibrate, griseofulvin, itraconazole, naproxen, sulfamethoxazole, phenylbutazone, azodicarbonamide, danazol, albendazole, nifedipine, cilostazol, ketoconazole, budesonide, loviride, glimepiride, biphenyl dimethyl dicarboxylate, digitoxin, paclitaxel, predinisolone acetate, hydrocortisone acetate and any suitable mixtures thereof.

The above objects and advantages are met by the presently disclosed method and apparatus. In addition, the above and yet other objects and advantages of the present invention will become apparent from the hereinafter set forth Brief Description of the Drawings, Detailed Description of the Invention, and claims appended herewith.

These features and other features are described and shown in the following drawings and detailed description. Furthermore, any combination and/or permutation of the embodiments are envisioned.

Again, other objects and features will become apparent from the following detailed description considered in conjunction with the accompanying drawings. It is to be understood, however, that the drawings are designed as an illustration only and not as a definition of the limits of the present disclosure.

BRIEF DESCRIPTION OF THE DRAWINGS

So that those having ordinary skill in the art will have a better understanding of how to make and use the disclosed composition and methods, reference is made to the accompanying figures wherein:

FIG. 2 illustrates a bar graph showing bulk density (BD) and Unconfined Yield Strength (UYS) of the API before and after dry coating.

FIGS. 3a-d illustrates typical images of uncoated and dry coated API, ibuprophen via Gradis/QicPic.

FIG. 4 illustrates flowability and visual comparison or benefit of the synergic impact from the dry coating of the minor component (API) and the mixing on the overall bulk properties of the entire blend.

FIG. 5 illustrates an agglomerate ratio of the API and blends with and without dry coating.

FIG. 6 depicts blend uniformity for three different API loadings before and after dry coating.

FIG. 7 is a plot diagram showing agglomerate ratio of dry coated API and blend uniformity plotted as a function of the API agglomerate size ratio.

FIG. 8 is a plot diagram illustrating compaction pressure and tablet tensile strength of the 3% wt API loading blend.

FIGS. 9a-9c illustrate faster API release rate from the tablets even with the hydrophobic silica coating due to the agglomerate size reduction impact of both the API and the blends.

FIG. 27 is a list of components in the blends and their mean particle sizes and particle densities.

FIG. 28 is an exemplary blend formulations and details thereof.

FIG. 29 illustrates characteristic API particle size (primary and agglomerated) PSD before and after the dry coating.

FIG. 30 illustrates Characteristic Blend particle size (primary and agglomerated) PSD for all the blends studied.

FIG. 31 illustrates bulk properties (bulk density, cohesion, and flowability) of API before and after the dry coating.

FIG. 32 illustrates a list of components in the blends and their mean particle sizes and particle densities.

FIG. 33 illustrates an example of dry coating formulation applied on the API.

FIG. 34 illustrates another example of blend formulation for 5 and 1 weight percent API loaded blends.

FIG. 35 illustrates characteristics particle size of the uncoated and dry coated APIs for their primary and agglomerated states.

FIG. 36 illustrates characteristics particle size of the blends with 5 weight percent loaded uncoated or dry coated APIs for their primary and agglomerated states. Blends were prepared at different length of mixing times.

FIG. 37 illustrates characteristics particle size of the blends with 1 weight percent loaded uncoated or dry coated APIs for their primary and agglomerated states. Blends were prepared at different length of mixing times.

FIG. 38 illustrates bulk properties (bulk density and flowability) of 5 wt % API loaded weakly cohesive coarse blends, wherein the blends were prepared at different mixing times.

FIG. 39 illustrates bulk properties (bulk density and flowability) of 1 wt % API loaded weakly cohesive coarse blends, wherein the blends were prepared at different mixing times.

FIG. 40 illustrates details of blend formulation for cohesive and fine blends.

FIG. 41 illustrates a characteristic particle size of the 5 weight percent uncoated or dry coated API loaded cohesive and fine blends showing their primary and agglomerated states, wherein the blends were prepared at different length of mixing times.

FIG. 42 illustrates a characteristic particle size of the 1 weight percent uncoated or dry coated API loaded cohesive and fine blends showing their primary and agglomerated states, wherein the blends were prepared at different length of mixing times.

FIG. 43 illustrates bulk properties of the 5 wt % uncoated or dry coated API loaded cohesive and fine blends prepared by mixing at different length of times to show synergistic impact from the dry coating and mixing on the blend flowability.

FIG. 44 illustrates bulk properties of the 5 wt % uncoated or dry coated API loaded cohesive and fine blends prepared by mixing at different length of times to show synergistic impact from the dry coating and mixing on the blend flowability.

FIG. 45 illustrates one embodiment of the blend formulation.

FIG. 46 illustrates a summary of the bulk properties of the blends comparing the between the blends with uncoated and dry coated API which were blended at different length of mixing times.

FIG. 47 illustrates formulations of example 14.1 to example 14.8.

FIG. 48 illustrates formulations of example 16.1 and 16.2.

FIG. 49 illustrates The bulk density, cohesion and FFC of placebo blend and uncoated and dry coated blends at three different API loadings along with one case where silica was added instead of coated onto API.

FIG. 50 illustrates The bulk density, cohesion and FFC of uncoated and dry coated blends (30% API loading) mixed for varying number of rotations. Placebo blend is included as a comparison (number of rotations, 750).

DETAILED DESCRIPTION

Figures 1A, 1B, 1C, 1D, 1E:
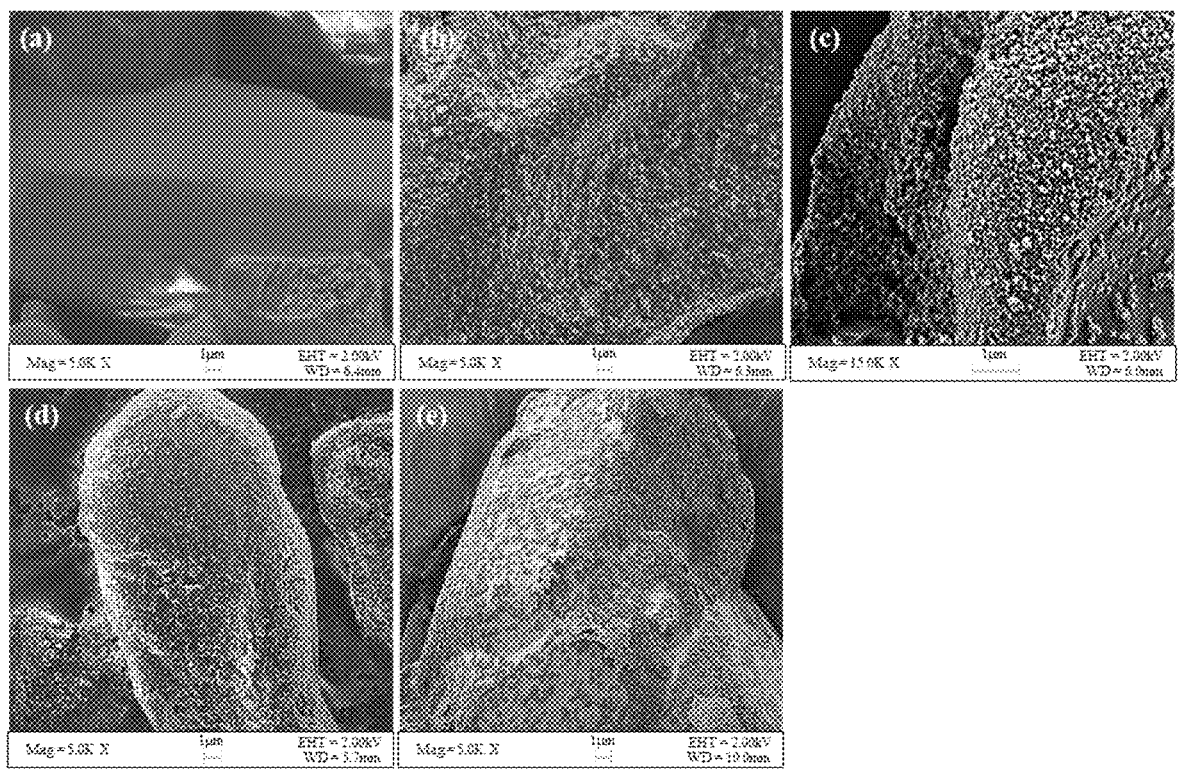
FIGS. 1a-e are, respectively, scanning electron microscope (SEM) images of before and after dry coating of an API.

For purposes of this description, range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 and the like, as well as individual numbers within that range, for example, 1, 2, 2.3, 3, 4, 5, 5.7 and 6. This applies regardless of the breadth of the range.

Unless noted otherwise, particle size distribution provided herein is volume-based particle size distribution was measured by a laser diffraction particle analyzer (Rodos/Helos system, Sympatec, NJ). Size statistics in terms of $d_{10}$, $d_{50}$ and $d_{90}$ are reported, which are the values of the particle diameter at 10%, 50% and 90% respectively in the cumulative volumetric particle size distribution. In the Rodos/Helos system, the Rodos device works by venturi principle to disperse the powder, and the Helos unit uses laser diffraction principles of Fraunhofer Enhanced Evaluation (FREE) and Mie Extended Evaluation (MIEE) theories of light scattering to determine the particle size. Size statistics of $d_{10}$, $d_{50}$ and $d_{90}$ at dispersion pressure of 0.1 bar are reported utilizing the FREE theory, the details for which can be found in Han et al. "Passivation of high surface energy sites of milled ibuprofen crystals via dry coating," *Journal of Pharmaceutical Sciences*, Vol. 102(7), 1-15 (2013) and Jallo et al. "Improvement of flow and bulk density of pharmaceutical powders using surface modification," *International Journal of Pharmaceutics,* 423 213-225 (2012).

Unless otherwise noted, bulk density and flowability, i.e., flow function coefficient (FFC), as provided herein is obtained using a Freeman FT4 powder tester (Freeman Technologies Ltd., Worcestershire, UK), where the bulk density and the flow function coefficient (FFC) were defined as the ratio of consolidation stress to the unconfined yield stress. The FFC was evaluated from a shear test under the consolidation pressure of 3 kPa on the recommendation of 205 ASTM standard for powders having low density (Emery et al., 2009; Emery, E., Oliver, J., Pugsley, T., Sharma, J., Zhou, J., 2009, "Flowability of moist 688 pharmaceutical powders," Powder Technol. 189, 689 409-415.) and the range normally used for pharmaceutical powders. Detailed procedures for both may be found in Freeman et al., Measuring the flow properties of consolidated, conditioned, and aerated powders—A comparative study using a powder rheometer and a rotational shear cell. Powder Technology 174, 25-33 (2007) and Huang et al., Flow and bulk density enhancements of pharmaceutical powders using a conical screen mill: A continuous dry coating device. Chemical Engineering Science 125, 209-224 (2015).

Though FFC is the flowability measure used herein, one of ordinary skill in the art would recognize that other flow indices can be used, such as angle of repose, Carr index, Hausner ratio, flow through orifice testing device, and others. In addition an agglomerate ratio may provide one such measure that requires lesser samples. Further, one of ordinary skill in the art would be able to use a suitable ring shear tester or equivalent at a suitable pre-compaction pressure, for example a novel material sparing powder strength tester device called the SpinTester-X (by Material Flow Solutions, Inc.), to determine FFC at low pre-consolidation in a manner comparable to FT4. A classification of powder flow behavior based on FFC is defined by Schulze, D., Powders, and Bulk Solids. Springer (2008) according to the FFC value: "FFC<1—not flowing, 1<FFC<2—very cohesive, 2<FFC<4—cohesive, 4<FFC<10—easy flowing, and FCC>10—free-flowing".

Bulk density was measured through a standard FT4 testing procedure that first conditions the powder to yield very repeatable results for the bulk density as discussed in the detailed procedures of Freeman, et al. mentioned above. Prior to powder characterization the powder was conditioned to remove stress or excess air from the powder bed by passing a conditioning blade through the powder bed. This process will be referred to as the conditioning cycle. The conditioned bulk density was measured by loading the powder samples into the 25 ml split vessel above the minimum fill level. After a conditioning cycle was performed, the vessel was split to remove the top portion of the powder; the density was determined from the mass of the remaining powder in the 25 ml vessel.

The powder mixing process is a common yet critical part of numerous industry sectors including, agriculture, food, cement, plastics, and pharmaceutical. The mixedness or homogeneity of powder blends is one of the key factors affecting the final product quality, especially for pharmaceutical products, as it is a major regulatory requirement for the final dosage. For active pharmaceutical ingredients (API) loading at or below 5 weight percent, achieving the targeted content uniformity is challenging. In particular, even if mixing were ideal, the lowest possible coefficient of variation ($C_v$), a standard measure for the quality of mixing, is inversely proportional to the drug dose and proportional to the API particle size.

Hence, available models to estimate $C_v$ recommend using finer drug powders for improving blend homogeneity as drug dose and loading are reduced. Unfortunately, these models assume ideal mixing, which is a non-trivial operation for fine API powders due to their cohesive nature, and further, they do not explicitly account for API agglomeration, hence model predicted $C_v$ values are not achievable.

Classical approaches to achieving excellent drug content uniformity (CU), which may be assessed via $C_v$, include using wet granulation, and in some cases using ordered mixtures. For the latter, cohesive and finely milled API particles are deposited during mixing onto the surface of the coarse excipients that are one or more magnitudes larger in size than the API. The advantage of wet granulation is that it can be used for both high and low drug loaded blends because it could improve the flowability due to the size enlargement or enhance drug content uniformity due to better API dispersion within the granules that naturally counters the tendency for fine API particle agglomeration. However, the process is energy and resource-exhaustive due to the number of steps required and the need to use water and other solvents that could impair API stability. For exceptionally low drug loadings, ordered mixtures are also an option where fine API particles stay attached due to their interparticle cohesion force with coarse excipient particles. As a result, API agglomeration problem is reduced, and uniform distribution of the API could be achieved along with improved flowability of the powder blend without being adversely impacted by fine API particles. Potential shortcomings of this approach include, limited drug loading, the need for using excipients that have narrow particle size distribution (PSD), specific mixing requirements, and a limited range of drug loadings. For example, the use of specialized higher intensity mixing devices and preferred types of excipients may be needed to attain desirable CU at exceptionally low drug loadings. Such difficulties in uniformly coating micro-sized APIs on carrier particles were also confirmed through an energy-based stick-bounce model.

The impregnation method has been used recently due to its capability of achieving good uniformity for ultra-low API loading where the API is deposited on porous non-dissolving and inert excipients. This approach could naturally provide excellent CU, since, in theory, the API is distributed throughout a larger, well flowing porous carrier particle. However, for commercial usage where avoiding downstream segregation could be challenging, as it would require excellent PSD control through milling or using a rather narrow sieve-cut size range. Other challenges could be the selection of suitable solvents that result in low viscosity API solutions, solvent recovery for reduced environmental footprint, and effective drying for complete removal of the solvents. Recent work pointed to additional issues such as slow and/or incomplete drug release and reduced storage stability in cases where the drug could attain nano-confinement induced amorphous state.

An alternate approach to encounter poor processability of fine APIs is the dry coating, a solvent-less method to reduce the cohesion of fine powders leading to improved bulk powder properties such as, but not limited to, flowability, packing density, fluidization, and dissolution. A significant advantage of dry coating is in enhancing powder blend properties such as flowability, bulk density, dissolution rate, as well as promoting direct compression tableting along with improved tablet properties at high drug loadings, even when only one of the constituents is dry coated. Most relevant to the current paper, several studies have also examined the impact of dry coating on reduced agglomeration, including subsequent impact on mixture uniformity at low API loading. For example, a model fine-sized (~10 μm) water-soluble API, micronized acetaminophen (mAPAP), was used at API loadings of 3, 5 and 10 wt % in binary blends with Avicel Ph-102 (~120 μm) to examine the influence of dry coating with a fixed amount (1 wt %) of hydrophobic silica R972P on the blend CU. Owing to the disparate sizes of the API and excipient, the condition where achieving uniformity would be challenging, and the effects of mixing time and the dry coating on the blend uniformity were explored.

However, the impact of dry coating on flowability and bulk density of the blends to promote direct compression tableting was not examined, nor the effect of diverse types and amounts of silica, as well as their impact on tablet dissolution was investigated, presumably because the API was readily water soluble. A major shortcoming was the assessment of agglomerate size estimated through sieving which provided limited resolution. A more recent study examined the impact of silica type and amounts on dissolution to better understand the combined effect of reduced agglomeration and altered surface hydrophobicity by considering poorly water-soluble APIs. Although it considered multiple methods for better assessing the size of agglomerates, it did not consider forming blends or tablets.

Dry coating with distinct types and amounts of silica may influence the API agglomerate sizes and consequently, the blend properties including CU at lower drug loadings as compared to the work by Huang et al (2017). It would be also interesting to examine the influence of altered surface hydrophobicity as well as agglomeration on dissolution from tablets. In addition, the impact of dry coating could be assessed on the blend flowability and bulk density that can improve downstream processability.

Although the examples and prior art discuss challenges in powder handling and powder-based solid dosage products concern pharmaceutical products, the current invention can be beneficially applied to wide ranges of powder based applications, ranging from food, agrochemical, specialty chemical, energy, metal, and cement industries, which require well flowing (FFC over 5 or 6) and well compacting (bulk density over 0.45 g/mL) powders ("Powder Flow Properties" by Kerry Johanson, Encapsulated and Powdered Foods, (2005) CRC Press, 9780429120152; Diederich, P., Mouret, M., Ryck, A., Ponchon, F., EScadeillas, G. "The nature of limestone filler and self-consolidating feasibility-Relationships between physical, chemical and mineralogical properties of fillers and the flow at different states, from powder to cement-based suspension." Powder Technology. 218: 90-101).

In this present disclosure and invention, three lower levels of API loadings, 1, 3, and 5 wt %, are considered in pharmaceutically relevant multi-component blends to assess the impact of reduced agglomeration as well as altered surface hydrophobicity after dry coating the API with diverse types and amounts of silica on the blend uniformity, as well as critical tablet properties such as the hardness, and dissolution. Since dissolution could pose a challenge for poorly water-soluble drugs for which finer API sizes are preferred, milled ibuprofen (d50~10 μm) was selected as the model poorly water-soluble API. It was dry coated with a hydrophobic (R972P) or hydrophilic (A200) silica at either fixed silica wt % or fixed value of theoretical surface area coverage (SAC) by silica. Unlike a previous study, where there was a significant size difference between blend components, which could promote segregation, all major components in this study were selected to have less significant size difference. That would also help better understand the impact of API agglomeration on mixedness and subsequent content uniformity. Accordingly, the blend formulation included fine grades of microcrystalline cellulose (Avicel 105) and lactose (Pharmatose 450) at equal weight concentrations, magnesium stearate as the lubricant, and crospovidone as the disintegrant.

Another important reason for selecting such fine sized constituents was to better discern the impact of dry coating on blend flowability and bulk density even though the only constituent to be dry coated would be the API at low concentrations. The particle size distributions were assessed via two different dry powder-based methods as per Kim et al. (2021), and blend sampling was done using a spinning riffler as per Huang et al. (2017).

The blends processing parameters such as the mixing time, intensity, and vessel filling degree were fixed to eliminate mixing operation impact on the blend properties. It was hypothesized that for all three low drug loading cases, all dry coating formulations would aid in improving the blend uniformity to the targeted range due to the agglomerate size reduction as well as appreciably improve blend flowability and bulk density without adverse impact on tablet compaction and hence in principle, enhancing blend processability.

Again, the following materials and methods and examples are merely given as illustrations of the principles of the invention. The invention is not so limited to the following examples. Instead the examples are given to illustrate the principles of the invention in certain aspects. Various deviations from the examples given herein are possible.

2.0 Materials and Method

Materials

As received ibuprofen (Ibu), donated by BASF, USA, was milled down to a finer size (~10 μm) for all the experiments. Microcrystalline cellulose (Avicel PH105, donated from FMC Biopolymer, USA) and lactose (Pharmatose 450, a gift from DFE pharma, USA) served as the filler and binder.

Crospovidone was selected as the disintegrant, to aids tablet disintegration during the dissolution process (Kollidon-CL, a donation from BASF, USA). Magnesium stearate (MgSt, Mallinckrodt Inc., USA) was used as a lubricant for smooth compaction. For coating materials, Acrosil 200 (nano-sized hydrophilic fumed silica) and R972P (nano-sized hydrophobic fumed silica) were selected.

Evonik Corporation (Piscataway, NJ, USA) donated these silicas. The sizes and particle densities of the excipients are listed in FIG. 27.

Method

Preparation of API by Milling

The as-received Ibu was milled to smaller sizes (~10 μm) by employing a fluidized energy mill (FEM). The feeding rate, feeding pressure, and grinding pressure are the three parameters that control the milled size. These three parameters were adopted from a previous study, and further fine-tuned to 8 g/min, 30 psi, and 25 psi as the feeding rate, feeding pressure, and grinding pressure, respectively.

Dry Coating

The current study employed an established material sparing high-intensity vibratory mixer (LabRAM, Resodyn, USA) to dry coat the milled Ibu. LabRAM can be operated at up to 100 times gravitational force and up to 100 Hz vibration frequency to achieve mechanical coating of silica on the surface of the host particles, in this case, the milled Ibu. A predetermined amount of either hydrophobic (R972P) or hydrophilic (A200) silica was added with the milled Ibu in a 300 mL plastic screw-top container. The container was placed in LabRAM and mixed for 5 minutes under 75 times the gravitation force at 60 Hz. Further details of operations may be found in the previous papers.

To examine the impact of dry coating formulation on the properties of blends and tablets, four cases were selected, each representing a certain objective: R972P (hydrophobic), representing lowest wettability, and A200 (hydrophilic), representing highest wettability, each at fixed 2.31 wt % as two extreme surface hydrophobicity cases, and lesser, intermediate yet adequate amounts of R972P or A200 silica to achieve fixed 50% available surface area coverage (SAC).

SEM Imaging

Although the effectiveness of the dry coating could be inferred from flowability enhancements, it was qualitatively assessed by analyzing the surface of milled Ibu before and after the dry coating via Scanning Electron Microscopy (SEM, EM JSM-7900f, JEOL). Details of the sample preparation method are discussed elsewhere. The resulting images are presented in FIG. 1.

Powder Sizing: Primary and Agglomerate Size Evaluations

Particle sizes of powder constituents before and after blending were evaluated via two different particle sizing methods to assess their primary sizes as well as naturally agglomerated state. Primary particle sizes were measured utilizing a compressed dry air dispersion (1 bar dispersion)

basis laser diffraction particle sizer (Rodos/Helos, Sympatec, USA). Agglomerated particle sizes were assessed by a gravity dispersion based dynamic imaging particle sizer (Gradis/QicPic, Sympatec, USA).

Preparing Multi-Component Blends at Low API Loading

Mixing parameters such as the order of filling each constituent, fill level, mixing intensity, and mixing time were held constant. The powder blend, except for MgSt, was hand mixed before adding it to a 4-pint V-shaped container. MgSt was added during the last 90 seconds of mixing time. The filling level was held constant at ~37% of the capacity by volume (280 g of blend weight). Both total mixing time and intensity were fixed to 30 min and 25 rpm, respectively, as per previous work. FIG. 28 presents the details of blend formulations, which vary as per API loading and the dry coating formulations of the API.

Bulk Powder Properties Tests: Bulk Density, Cohesion, and Flowability

The bulk powder properties, such as the conditioned bulk density, bulk powder cohesion (shear strength measured at zero normal force), and powder flow function coefficient (FFC, the ratio between the major principal stress and unconfined yield strength), of the milled Ibu before and after the dry coating, as well as blends (placebo and 1, 3, and 5 wt % loaded API), were evaluated using FT4 (Freeman Technology, UK). Details of measurement methods may be found elsewhere. The FT4 evaluations also provide quantitative assessments to judge the effectiveness of the dry coating, including the unconfined yield strength (UYS) and the powder cohesion.

Content Uniformity Assessment

The API concentration was measured after mixing to determine the blend uniformity. A spinning riffler (SP-230, Gilson Company, INC., USA), a widely used sampling method in the powder industry, was used for collecting powder samples. The riffler has 16 collection ports, each equipped with a test tube, fed by a vibratory chute feeder tray. After the first pass, one randomly selected tube was processed one more time to reduce the size of samples per test tube (Huang et al. 2017).

Subsequently, 400 mg of the samples from each tube were taken and added to a 250 mL glass bottle containing 100 mL of pH 7.2 phosphate buffer. The prepared solution was left for 48 hours with the magnetic stirrer rotating at 400 rpm to ensure complete extraction of the API. From that, 5 mL of filtered solution was transferred to a 25 mL volumetric flask and diluted by adding 20 mL buffer solution, which was vortexed at 1500 rpm for 10 seconds.

The target Ibu concentrations for 5, 3, and 1 wt % loaded blends were 40 mg/L, 24 mg/L, and 8 mg/L (equivalent to 20 mg, 12 mg, and 4 mg API dissolved in 500 mL solvent), respectively. The concentration of the extracted Ibu in the solution was detected using a UV-visible spectrophotometer (Thermo Scientific, USA) at a wavelength of 221 nm. For each sample, triplicate measurements were taken and averaged to ensure repeatability. The measured absorbance was converted into the concentration based on a calibration curve. To determine the uniformity of the tested blend, <USP 905> guideline was adopted. For any of the powder blends, initially, 10 samples were evaluated to determine if the dosage per sample is within 90-110% of the target dosage (stage 1). Then, utilizing Eq. (1), the relative standard deviation (RSD) of the API concentration was calculated to check if % RSD is less than 5%.

$$\text{Percent } RSD = \frac{\text{Standard Deviation of the texted samples' drug content}}{\text{Average of the drug content measured from the samples}} \times 100 \quad (1)$$

If both the criteria from stage 1 were satisfied, the blend was uniform. If, not additional 20 samples were analyzed.

Particle True Density Measurement

The true particle density of the uncoated and coated milled Ibu and each blend component were measured before blending. A Multipycnometer (P/N 02029-1, Quantachrome Instruments, USA) was used to take five to ten repeated measurements under a helium environment. Assuming the ideal granular mixture after blending, Eq. (2) was utilized to calculate the blend's particle density.

$$\rho_{particle\ density\ of\ blend} = \sum_{i=1}^{5} x_i \rho_i \quad (2)$$

Here, $x_i$ and $\rho_i$ denote the mass fraction and particle density of component i, respectively.

Surface Energy Measurement

The changes in the surface energy of the milled Ibu after dry coating was measured using an automated inverse gas chromatography (SEA-IGC; Surface Energy Measurement Systems Ltd., UK) to evaluate the Lifshitz-van der Waals (LW) dispersive surface energy of the powder samples.

The dispersive surface energy values of the blends were also measured to assess any potential silica transfer from the dry coated Ibu onto the surfaces of other components. The infinite dilution method was employed for the dispersive surface energy measurement for API and the blends. The details of sample preparation and analysis methods are known to those skilled in the art.

Tablet Preparation and Tensile Strength Test

Carver platen press (Carver, Inc., USA) with a 0.5-inch inner diameter stainless die and a flat-faced round punch was used to prepare 400 mg tablets under 1.0 metric ton (equivalent to 77 MPa) compaction pressure. The die set was cleaned thoroughly with alcohol wipes and air-dried before and after. The tablet breaking force was measured using a diametrical compression test in a texture analyzer (Texture Technologies Corp., USA). The measured breaking force was converted into the tablet tensile strength based on Eq. (3).

$$\sigma_T = \frac{2 \times F}{\pi D_T \delta_T} \quad (3)$$

Here, $\sigma_T$, F, $D_T$, and $\delta_T$ represent the tensile strength of tablet, measured tablet breaking force, the diameter of the tablet, and thickness of the tablet, respectively. A minimum of 10 tablets were evaluated and the calculated values were averaged.

Wettability Evaluation: Modified Washburn Method

As reported by Kim et al. 2021, the surface wettability of the powders varies with the dry coating formulation, which could impact the dissolution behavior. Here, the surface wettability of the coated and uncoated milled Ibu was evaluated to assess the influence of surface wettability of Ibu on the API release rate from the tablets. The details of the method and sample preparation are known by those skilled in the art. The surface wettability of the powder samples was computed by measuring the liquid penetration rate using Attension Sigma 700 (Biolin Scientific Inc., Linthicum). Both the reference and testing liquids were pre-saturated by dissolving Ibu for a minimum of 48 hours before conducting the experiments.

API Release Rate Test: USP II Method Basis Tablet Dissolution

The API release rate from the prepared tablets was analyzed through the dissolution testing of the tablets in pH 7.2 phosphate buffer (the dissolution medium), employing the USP II paddle method, USP <711>, (USP II, SOTAX, Switzerland). To ensure the sink condition during the dissolution process and adequate absorbance peak response via UV-vis analysis without further dilution (UVvis spectrometer, Thermo Scientific, USA), 500 mL dissolution medium was used, considering both the low API dosage and the solubility of 2 mg of Ibu per 1 mL of PBS buffer in PBS pH 7.2 buffer at the ambient condition. Both the temperature of the system and the rotating speed of the paddle were fixed at 37° C.±0.2° C. and 50 rpm, respectively, during dissolution.

At the predetermined time intervals, 3 mL of samples were drawn, while replenishing the buffer amount by immediately adding 3 mL make-up solvent. The absorbance of the sample was measured in duplicate at the wavelength of 221 nm after filtering the collected 3 mL with 0.45 µm syringe filter, without further dilution. To ensure the repeatability of the measured API release rate for each blend formulation, the experiments were repeated at least three times to obtain the averaged values.

Thermogravimetric Analysis (TGA): Tablet Moisture Content Analysis

The moisture content within a blend and tablets could have a notable impact on the API dissolution or tablet disintegration rate as well as the tablet strength. Hence, the moisture contents were measured, in particular, to discern the impact from the dry coating formulation on the API, blend, and tablet properties.

It was assumed that the measured moisture content from the tablet is also representative of the powder blend since tablets were formed immediately after the blends were prepared. A 50 mg of crushed tablet in a ceramic crucible was placed to assess the moisture content of the tablet using a thermogravimetric analyzer (TGA, TGA/DCS1/SF STARTe system, Mettler Toledo Inc., USA).

The percent change in the tablet weight was measured while the sample was heated in the nitrogen environment from 25° C. to 200° C. at the temperature rising rate of 10° C. per min. The system was cooled back to 25° C. at the same rate as the heating rate. The averaged values for each formulation and API loading were measured by testing three samples.

Results

Bulk Powder Properties of API and Blends Before and After Dry Coating

Bulk Density, Flowability, and Agglomeration of the API Powders

The bulk properties such as the bulk density, unconfined yield strength (UYS), cohesion, and FFC, of the API before and after dry coating, were evaluated using the FT4 powder tester. The results for the API bulk density and UYS before and after the dry coating are shown in FIG. 2, while FIG. 29 also includes cohesion, FFC, and the corresponding flow regime. Remarkably, the bulk density doubled after dry coating with both types and amounts of silica (fixed wt % and fixed % SAC, equivalent to 2.31 wt % and 50% SAC, respectively), whereas the UYS became as low as one-tenth of the original for fixed wt % R972P and one-fifth for other silica cases. Similarly, the FFC values improved, starting with under 2, indicating a very cohesive flow regime, reaching high FFC values, translating to respective changes by two or even three flow regimes, the latter being for both the cases of R972P coating. One probable reason for such enhancements in UYS and FFC could be the reduced surface energy after silica coating as per previous reports. Therefore, the dispersive and polar components (electron acceptor and donor) of surface energy of dry coated APIs were measured via inverse gas chromatography (IGC). The total surface energy (sum of dispersive energy and polar components), provided in FIG. 30, indicated that the reduction was higher due to R972P as compared to that from A200, which was expected due to the lower surface energy of R972P. However, these results demonstrated that the reductions in surface energy values were only about 20 to 30 percent, which are while significant, were insufficient to cause the dramatic reduction in the UYS (FIG. 2) or enhancement in FFC (FIG. 29). That means that such significant enhancements are due to the creation of nano-scale asperities after dry coating that leads to over an order of magnitude cohesion reduction as per the Chen multiasperity particle contact model.

Next, Agglomeration of the API, the most important quality attribute affecting drug content uniformity, was assessed for APIs with and without dry coating. The Gradis/QicPic method was used since it provides gentler dispersion as compared with pressure dispersion method using Rodos/Helos so that a better measure of API agglomeration could be assessed. The Gradis/QicPic also provided much better agglomerate size resolution as compared with the sieving method used in previous work that only provided coarse, limited resolution. These results in terms of d10, d50, d90 and d99 along with associated standard deviations are provided in FIG. 31. The d99 values, although not used in any computations, were reported since they better captured typical large agglomerates evident in the entire PSDs as compared to d90 and could explain the relative impacts of four different silica formulations on either the uniformity or bulk properties of the blends.

FIG. 3, showing typical agglomerate images captured by the instrument, provided visualization of the causes for significantly different standard deviations in the agglomerate sizes for the uncoated versus dry coated APIs. The d50 and d90 values of the agglomerates (Gradis/QicPic) of the uncoated API were 1379 µm and 2492 µm, respectively, whereas the d50 of the primary particle (Rodos/Helos) was ~14 µm, indicating the agglomerate ratio (AR) of almost 99 (FIG. 31).

In contrast, dry coated APIs exhibited significantly reduced agglomeration, particularly for fixed wt % formulations that led to AR of less than 4, hence well over an order of magnitude improvement through dry coating. The worst case was for fixed % SAC of A200 leading to AR of about 40. The AR results for the APIs are also presented in a graphical form, discussed in the next section, which examines if such dramatic reductions in the AR values could have a positive impact on the blend uniformity and blend bulk properties.

Bulk Density, Flowability and Agglomeration of the API Blends

Dry coating with both types and amounts of silica resulted in enhancement of key bulk properties of the API powders as discussed in the previous section. However, such enhancements cannot assure improvements in these properties of their blends since the drug loading is low. Therefore, following the mixing protocols described previously, all 15 blends as well as placebo presented in FIG. 28 were prepared. Their bulk properties such as the bulk density, unconfined yield strength (UYS), cohesion, and FFC were evaluated using FT4 powder tester.

The particle size distributions were measured using the gentler dispersion method discussed previously to assess the level of agglomeration even though that cannot guarantee the extent of API agglomeration or deagglomeration that could occur during the blending and sampling process for the content uniformity measurements.

The results of the flow function coefficient (FFC) as a flow index are plotted for all three levels of API loading (FIG. 4), whereas all the bulk properties including the bulk density and cohesion for all the blends are summarized in FIG. 32. Remarkably, even at such low drug loadings including just the 1 wt % case shown in FIG. 4, the flowability of the blends with dry coated Ibu improved from cohesive to well flowing, hence by one flow regime.

Specifically, the net amount of either type of silica addition to each blend at the API loading of 1 wt % was just 0.007 to 0.023 wt % (FIG. 28). In contrast, as per standard industry practice of addition of flow aids or glidants such as silica to improve powder flow would have required much higher amounts, e.g., 1 wt % of silica, and could not have resulted in the FFC enhancements comparable to what was achieved here.

As shown from the flowability results (FIG. 32), without silica, the FFC for the API loading of 1 wt % was 3.6, implying poor flow, it increased to 6.0 and 5.4 for mere ~0.012 wt % of R972P and A200 silicas, and to 7.1 and 7.5 for mere ~0.023 wt % of R972P and A200 silicas, respectively.

It was surprising that at such low level of silica in the 1 wt % API blends, specifically for 0.023 wt % (fixed wt % cases), A200 appeared to have outperformed R972P, which could be attributed to the smaller size hence greater number of silica particles for A200.

Such dramatic effect could also be because although the flowability of a blend is adversely affected by the presence of cohesive fine powders like the API, dry coating that poorest flowing constituent would mitigate that adverse impact. As expected, compared to the placebo blend, the flowability of the blends containing uncoated API did not improve; in fact, it deteriorated for the highest level of API loading, i.e., 5 wt % (FIG. 4 and FIG. 32).

In contrast, for all the blends at all four cases of silica formulations, flowability improved to attain easy flowing category, hence significantly improving the blend processability and nearly reaching the FFC levels to promote high-speed direct compression tableting. To discern the impact of added silica during blending instead of dry coated silica on flowability enhancement of blends, the blend with the highest level of hydrophobic silica was considered.

Accordingly, the 5 wt % API loaded blends with fixed wt % silica was prepared via blending the mixture of uncoated API, 0.116 wt % R972 silica, and other excipients (44.4 wt % each Avicel 105 and Pharmatose 450, 5 wt % Kollidon-CL, followed by final addition of 1.0 wt % MgSt).

This mixture led to cohesion of 0.37 and FFC of 4.22 (last row of FIG. 32), in contrast to cohesion of 0.21 and FFC of 6.50 when the same amount of silica was dry coated (FIG. 32), highlighting the power of silica dry coating, even when the dry coated constituent has such low level, over simple blending with added silica.

The values of agglomerate ratio (AR), defined as d50 Gradis/d50 Rodos, were computed based on the PSD data in FIG. 33, and plotted in FIG. 5 for the API, placebo, as well as powder blends. While the AR for the uncoated API was about 100, it was reduced by over an order of magnitude and ranged from ~2 to ~4 for various dry coated API formulations, shown in red bars, FIG. 5.

For the blends, the AR for placebo was ~14, whereas it ranged from ~15 to 24 for uncoated API blends, increasing monotonously with the API loading from 1 to 5 wt %. The agglomeration (AR values) decreased significantly for the blends with dry coated APIs, although the reduction was less for 1 wt % blends, which was expected.

However, for 3 wt % blends, some of the silica coating formulations led to AR reductions higher than the API alone, indicating synergistic effects such as the silica transfer from the API to the excipients during the mixing time, as was also reported in another work.

Interestingly, such a synergistic effect was less apparent for 5 wt % blends with dry coated APIs. Nonetheless, all the blends with dry coated APIs demonstrated significantly lesser agglomeration than placebo or uncoated API, indicating a remarkable impact of API dry coating. These results for the blends and the APIs suggest that reduced API agglomeration before and after blending conformed with improved flowability and hence would lead to better drug content uniformity for all the blends as discussed in the next section.

Blend Uniformity

Blend uniformity for three different API loadings and four varying dry coating formulations were evaluated by calculating % RSD per USP <905>, see FIG. 34. The impact of the dry coating formulation and the drug loading on the blend uniformity (% RSD) better visualized in FIG. 6. For 5 and 3 wt % drug loading blends, % RSD values were particularly good for all the silica formulation cases as they were well under 6%.

Remarkably, even the 1 wt % API loading blends, which were not considered by Huang et al. 2017, resulted in excellent RSD values under 6% for two of the blends that included API dry coated with either silica type at fixed SAC %.

However, two other blends with the API dry coated at fixed wt % failed to achieve the targeted uniformity, and the calculated % RSD values were above 6%. Such results could not be explained based on the API and blend AR ratios (see FIG. 5), which are based on d50 measured using Gradis (FIG. 31).

Interestingly, those two cases had significantly higher d99 sizes as compared to d90 values, which may suggest the presence of a group of large secondary agglomerates.

Nonetheless, neither the API nor blend agglomerate sizes could capture the state of API agglomeration and API distribution within the blends resulting from the mixing process. For these two cases, it could be concluded that in addition to the major factors such as cohesiveness, agglomerate size and mixing process, other secondary factors such as wall friction, stresses, moments, and particle shapes could also be affecting the blend uniformity.

Therefore, future research should consider quantitative measurement of the state of API agglomeration within the blends to better understand the mixing dynamics that would certainly impact the blend uniformity.

It is remarkable that selectively dry coating APIs, acceptable % RSD values could be achieved for both silica types for drug loading as low as 1 wt % API.

Predicting Blend Uniformity for Low API Loading Cases

The agglomerate size distributions measured using Gradis had significantly higher resolution compared to those obtained by sieving in previous work. That allowed for evaluating the blend uniformity model proposed by Johnson in 1972 (Eq. (4)), valid for the API loading between 1 to 10 wt %, allowing for the inclusion of entire PSD.

$$RSD\ (\%) = 100\ y \left(\frac{\pi\rho}{\theta G 10^{-2}}\right)^{1/2} \left(\sum_{i=1}^{n} f_i (d_i\ 10^{-4})^3\right)^{1/2} \quad (4)$$

In the above, 10-3 and 10-4 are conversion factors, y represents the weight fraction of the major components in the blends, while p and G are the particle density of API in g/mL, and the API dosage per sample in mg, respectively. Further, fi is the weight fraction of size di of the API, where di is the size class in µm. As evident from Eq. (4), the blend uniformity of low API loading between 1 to 10% is directly dependent on the agglomerate size or particle size distribution, as fi and di terms infer. Johnson model (Eq. (4)) assumes spherical non-agglomerated API particles that are randomly distributed within the blend hence not directly applicable in the present situation. Regardless, it was used for the purpose of obtaining a crude estimate of the expected blend uniformity by replacing the primary particle size with the agglomerate sizes distributed over 25 bin sizes. The connection to the API cohesiveness was evident since the equation accounts for the PSD data obtained from Gradis, which captures the variations in the agglomerate sizes (FIG. 31), affected by API cohesion (FIG. 31).

The analysis based on Johnson's model resulted in RSD predictions presented in FIG. 35. Despite major assumptions behind the Johnson model including simplifications employed, the outcomes based on the Gradis assessed agglomerate sizes for the blend uniformity of both the uncoated dry coated API blends agreed with the experimental results, except for two specific cases of dry coated blends. For both those cases, the API loading was the lowest at 1 wt %, and the silica amounts were high, pointing to a significant challenge posed at low drug loadings along with the need for judicious selection of silica. In addition, the agglomerate size distribution via 25 bin sizes in Eq. 4 may have been inadequate for two fixed silica wt % coating cases because of the potentially lop-sided effect of a large secondary peak that resulted in much larger d99 sizes as compared to d90 sizes. Such a large disparity between d99 and d90 sizes was not present for the fixed % SAC cases. Further, the assumptions of perfect mixing, spherical particles, and using API density as agglomerate density need to be examined to achieve better agreement in all cases. Nonetheless, Johnson's model along with Gradis based agglomerate size distributions could provide a first order estimate of drug content uniformity for low API loaded blends. Overall, the outcomes confirmed the positive impact of dry coating on agglomerate size reduction leading to improved uniformity of low drug loaded blends.

Tablet Properties and API Release Rate

Tablet properties such as tensile strength and API release may be impacted because of dry coating. First, the tensile strength of the tablets, an important quality attribute towards blend processability, was analyzed to evaluate if dry coating had any adverse impact on tablet tensile strength since applying silica could reduce the overall surface energy that could reduce the bonding strength. In addition, since the tensile strength is a critical factor for tablet dissolution, it was measured to ensure that the improved API release rate was due to dry coating induced agglomerate size reduction and altered API hydrophobicity and not the tensile strength. Tensile strength testing was conducted at a low-level compaction force of 77 MPa, see Table 10. As was expected, the inclusion of API, even at a low percentage, led to a reduction in tensile strength as compared to the placebo for all cases including uncoated. Remarkably, however even at such a low compaction force, the tablets attained tensile strength of well above 1.00 MPa.

Higher compaction forces were considered for one set of blends with lower tensile strength values, namely, 3 wt % blends containing either uncoated or R972P fixed wt % dry coated API, to further discern the impact of dry coating on tensile strength. For these two blends, 400 mg tablets were compressed at three additional compaction pressures, see FIG. 8. Although the tablets containing the dry coated API had slightly lower tensile strength values, the reductions were marginal, and both the cases could achieve over 2 MPa tablet tensile strength at the compaction pressure of 130 MPa and above. The moisture contents of the tablets were also analyzed to assess if dry coating had any major impact. However, it was found that the moisture content for tablets at any fixed API loading were all statistically similar and there were no meaningful differences between the uncoated API tablet and all dry coated API tablets.

Figure 9B:
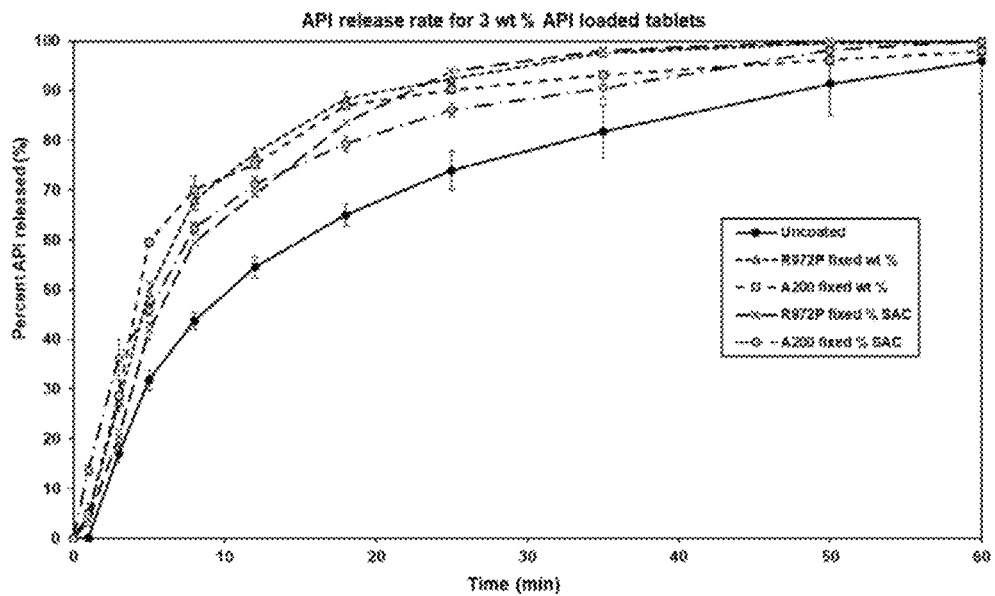
Figure 9C:
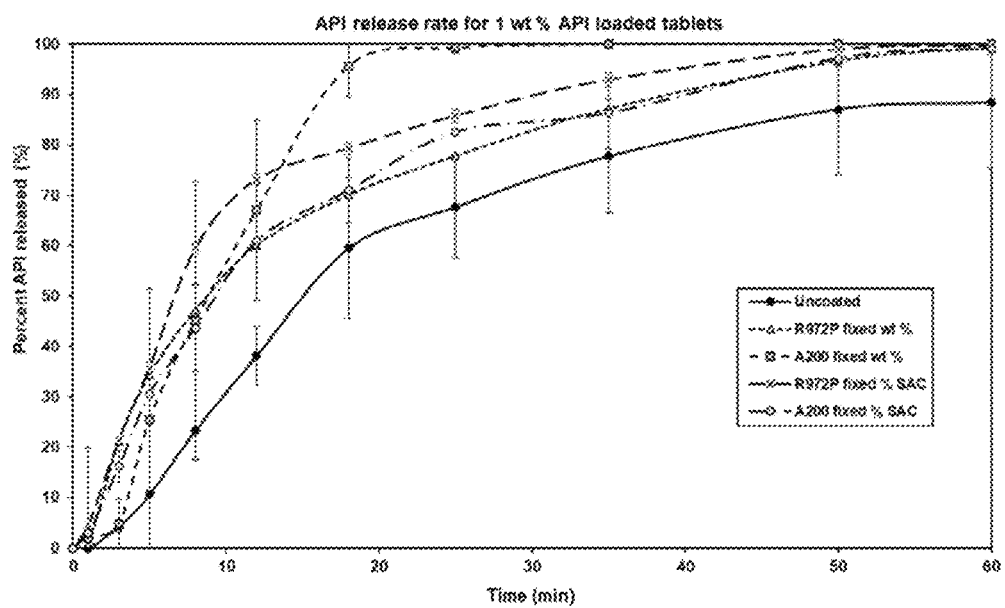

Next, the API release rates were measured using the USP II method in pH 7.2 PBS buffer to evaluate any impact on the API release rate due to different dry coating formulations on each API loading case. Ibu release rates from the tablets for all the formulations were presented in FIGS. 9(a) through 9(c), representing 5 wt %, 3 wt %, and 1 wt %, respectively. For all three loading cases, even at such low API loadings, the tablets containing the dry coated Ibu showed faster release rates than those of tablets containing uncoated Ibu. This was a favorable outcome as compared with API impregnation into porous supports such as neusilin, which could lead to slowed down dissolution.

Interestingly, the API release rates differed depending on the dry coating formulations as well as drug loadings. For example, at 5 wt % drug loading, A200 at 50% SAC yielded the fastest release, whereas at 1 wt % drug loading, A200 at fixed 2.31 wt % yielded the fastest release. Regardless of these differences, the expedited API release rates were due to the combined effect from the agglomerate size reduction and change in the surface hydrophobicity. Relative impacts from API agglomerate size reduction and surface hydrophobicity increase (decrease) due to R972 (A200) silica could be assessed based on conducting wettability testing via the modified Washburn method for uncoated and dry coated APIs. As seen in FIG. 37, as compared with uncoated Ibu, coating with hydrophobic silica led to a slight increase in hydrophobicity since the contact angle increased from 82.5 degrees to 83.1 and 85.8 degrees for fixed % SAC and fixed wt % R972P silica, respectively. In contrast, the agglomerate ratio went down from 98.9 for uncoated Ibu to 3.7 and 2.3 for fixed % SAC and fixed wt % R972P silica coated Ibu, respectively. Hence despite increases in hydrophobicity, the dissolution after R972P was faster, confirming a higher contribution towards faster dissolution due to agglomerate size reduction.

Overall, this investigation demonstrated the benefit of dry coating in enhancing the API release rate without having to change either excipients or disintegrants because of reduced API agglomeration despite hydrophobicity increase for the case of R972P.

Dry coating with silica led to reduced cohesion, flowability enhancement by one or two flow regimes, and most importantly, over an order of magnitude reduction in fine ibuprofen agglomeration, all of which could not be attributed to reduced surface energy alone and hence were due to the nano-scale morphology imparted by silica coating on the API surface. It was concluded that dry coating of API, even at the lowest drug loading amounting to extremely low silica fraction in the blend, influenced the flowability of multi-component blends having all fine sized excipients, noting that its flowability was poor (classified in the cohesive range) without API dry coating or even when silica was added during blending for one selected case.

The reduced API agglomeration after dry coating was the main driver for enhanced blend uniformity for all three low API loadings as compared to that with uncoated APIs. In addition, the analysis of surface hydrophobicity and agglomerate reduction for various coating formulations that included hydrophobic or hydrophobic silica, confirmed the significant role that API agglomeration (or lack of it) could play on tablet dissolution, negating even the adverse impact of increased drug hydrophobicity with R972P coating.

In conclusion, for all three low drug loadings, dry coating improved blend uniformity and tablet dissolution due to the agglomerate size reduction, without adverse impact on tablet compaction. Thus, while underexplored, dry coating based reduced agglomeration of fine APIs offers a new direction for future investigations that could better explore its positive and synergistic impact on drug product performance, including the blend uniformity, dissolution, and overall processability.

Dry coating of APIs as shown herein offers an alternative to wet granulation and other methods to address processability of low drug loaded formulations with potential for promoting direct compression tableting.

EXAMPLES

Example 1 (Fine and Cohesive Multi-Component Blend, Fixed Mixing Time): Synergistic Effect from the Dry Coating and Mixing on the Fine Particle Sized Multi-Component Blend of Low API Loading—Blend Agglomerate Reduction Example 1 illustrates the reduction in the agglomerate size of multi-component cohesive and fine low API loaded blends when the APIs are coated. Five components of similar particle sized (10~30 μm) blends were studied in this study. FIG. 27 provides the physical properties of the employed components. As the model active pharmaceutical ingredient (API), ibuprofen (Ibu), which belongs in BCS II classification was selected.

The ibuprofen was milled from the mean particle size of 50 μm to 10-15 μm using a fluidized energy mill (FEM, Pharmaceutical Micronizer Fluidized Energy Grinding Jet mill, Sturtevant Inc., Hanover, Massachusetts). The feeding rate, feeding pressure and grinding pressure were set as 8 g/min, 30 psi, and 25 psi, respectively. Micronization of the powders can be done with other than the described FEM method. The summarized mean particle size and particle density for the blend components are shown in FIG. 27.

Prior to the blending, the milled Ibu was dry coated with either Acrosil R972P or Acrosil A200 using a high-intensity vibratory mixer (LabRAM, Resodyn, USA) at the intensity of 75 times the gravitational force and 60 Hz for 5 minutes. The dry coating could be done with other methods. A 300 mL screw top plastic container was used for the dry coating. For each dry coating run, about 66% of the container volume was taken up by powder, which comprised the milled Ibu and nano fumed silica. For the dry coating formulation, four cases were prepared. In the first case, fixed wt % of either hydrophobic (R972P) or hydrophilic (A200) silica was used as the dry coating agent (guest particles). For the second case, fixed surface area coverage (SAC) % of either hydrophobic (R972P) or hydrophilic (A200) was used. The SAC % calculation is known by those skilled in the art. The uncoated and dry coated milled Ibu surfaces are shown in FIGS. 1(a) through 1(c), which present the Scanning Electron Microscopy (SEM, EM JSM-7900F, JEOL) analysis.

FIG. 2 presents the bulk powder properties of the API before and after the dry coating. For preparing the blends, mixing parameters such as the order of filling each constituent, fill level, mixing intensity, and mixing time were held constant. The powder blend, except for MgSt, was hand mixed before adding it to a 4-pint V-shaped container. For the hand mixing process, the pre-weighted components were added in a 1-gallon ziplock plastic bag and were gently shaken a couple of times, where the total time spent in the bag was less than ten seconds. MgSt was added during the last 90 seconds of mixing time. The filling level was held constant at ~37% of the capacity by volume (280 g of blend weight). Both total mixing time and intensity were fixed to 30 min and 25 rpm, respectively. The blending could be done with any other methods. FIG. 28 presents the formulation details for the resulting blends.

The primary particle size of API before and after dry coating and the resulted blends were evaluated using a compressed air dispersion method basis a laser diffraction particle sizer, Rodos/Helos (Sympatec Inc., NJ). The agglomerate particle size distributions of the API before and after the dry coating and blends were evaluated using a gravity dispersion-based dynamic imaging particle sizer, Gradis/QicPic (Sympatec Inc., NJ). Unlike traditional sieving or SEM-imaging or optical microscope based agglomerate size estimation, employed Gradis/QiPic provides statistically representative and repeatable full agglomerate particle size distribution based on more than $10^7$ particle image analysis while gentling dispersing the powders minimizing the impact on the agglomerates and preserving their original state as close as possible (see FIGS. 3(a) through 3(d)).

The summarized characteristic primary and agglomerated particle size distributions for the uncoated and dry coated APIs are shown in FIG. 29 and the summarized results for the blends are shown in Table 4. Based on the evaluated primary and agglomerate particle size assessments, the agglomerate ratio ($d_{50\ Gradis}/d_{50\ Rodos}$) was found and plotted as shown in FIG. 5.

As shown in FIG. 5, the agglomerate size had reduced significantly with the inclusion of the dry coated API within the blends. The outcome was not expected considering the minute concentration of either hydrophobic (R972P) or hydrophilic (A200) silica in all the blends (see FIG. 28).

Example 2 (Fine and Cohesive Multi-Component Blend, Fixed Mixing Time): Synergistic Effect from the Dry Coating and Mixing on the Fine Particle Sized Multi-Component Blend of Low API Loading—Blend Flowability Improvement Example 2 discusses the notable improvement in flowability for the cohesive and fine multi-component low API loaded blends once the APIs are coated. Identical powder preparation and mixing methods were used for Example 2. The blends evaluated for Example 2 are identical to the blends described in Example 1.

Processability (flowability and bulk density) of the uncoated and dry coated API and the blends including the placebo were evaluated using a powder rheometer, FT4 (Freeman Technology, UK) under 3.0 kPa of pre-compaction pressure for shear testing. The processability of the powders can also be assessed using a ring shear tester or other types of powder rheometer. The remarkable flowability and bulk density improvements after the dry coating of API were observed as shown in FIG. 31. To the great surprise, the blends flowability after the inclusion of the dry coated API, especially the one contains 0.023 wt % of hydrophilic silica (A200) showed unexpectedly high FFC improvement as shown in FIG. 4.

As shown in FIG. 4, For 1 wt % API loading blend, which contains A200 fixed wt % dry coated, Ibu showed remarkable FFC improvement from 3.6 to 7.5, which was not expected. This particular blend includes 0.023 wt % of silica which is minute in its composition. For the other cases, the flowability of the blends was improved by one flow regime, containing 0.007 to 0.116 wt % of silica, enabling a direct compaction process, higher weight and low weight variability capsule filling, or easy sachet filling. Compared to placebo and blends with uncoated API, the bulk density of the blends with dry coated API was improved marginally, from a minimum of 0.41 g/mL to up to 0.44 g/mL.

Example 3 (Fine and Cohesive Multi-Component Blend, Fixed Mixing Time): Synergistic Effect from the Dry Coating and Mixing on the Fine Particle Sized Multi-Component Blend of Low API Loading—Blend Content Uniformity Improvement Example 3 discusses the notable improvement in flowability for the cohesive and fine multi-component low API loaded blends once the APIs are coated. Identical powder preparation and mixing methods were used for Example 3. The blends evaluated for Example 3 are identical to the blends described in Example 1.

The content uniformity of the prepared blends was assessed and summarized in FIG. 6. After evaluating the blend uniformity, API concentration assay analysis was conducted. The powder sampling was done with a spinning riffler (SP-230, Gilson Company, INC., USA). 400 mg of collected powder samples were dissolved in a 100 mL pH 7.2 phosphate buffer over 24 hours. The dissolved API concentration in the buffer solution was measured with UV spectrophotometry (Thermo Fisher Scientific Inc., USA). To determine the uniformity of the blends, the averaged API concentration and relative standard deviation (RSD) in % was calculated following USP <905> guideline.

In general, the blends with dry coated API showed much enhanced blend uniformity especially for the blends with less amount of silica (0.012 wt % for R972P and 0.007 wt % for A200). Overall, the blend flowability and uniformity assessments demonstrated the much-enhanced fine multi-component blend's processability and its mixedness which leads to case of processing and better medicinal product quality.

Example 4 (Fine and Cohesive Multi-Component Blend, Fixed Mixing Time): Synergistic Effect from the Dry Coating and Mixing on the Fine Particle Sized Multi-Component Blend of Low API Loading—API Release Rate Improvement Example 4 discusses the notable improvement in flowability for the cohesive and fine multi-component low API loaded blends once the APIs are coated. Identical powder preparation and mixing methods were used for Example 4. The blends evaluated for Example 4 are identical to the blends described in Example 1. Observing significant reduction in the agglomerate ratio of the blends (see FIG. 5), API release rate from the blends were evaluated by preparing 400 mg tablets. Carver platen press (Carver, Inc., USA) with a 0.5-inch inner diameter stainless die and a flat-faced round punch was used to prepare 400 mg tablets under 1.0 metric ton (equivalent to 77 MPa) compaction pressure. To measure API release rate USP II paddle method was used with pH 7.2 phosphate buffer as the dissolution medium.

To ensure the sink condition during the dissolution process and adequate absorbance peak response via UV-vis analysis without further dilution (UV-vis spectrometer, Thermo Scientific, USA), 500 mL dissolution medium was used, considering both the low API dosage and the solubility of 2 mg of Ibu per 1 mL of PBS buffer in PBS pH 7.2 buffer at the ambient condition. Both the temperature of the system and the rotating speed of the paddle were fixed at 37° C.±0.2° C. and 50 rpm, respectively, during dissolution.

At the pre-determined time intervals, 3 mL of samples were drawn, while replenishing the buffer amount by immediately adding 3 mL make-up solvent. The absorbance of the sample was measured in duplicate at the wavelength of 221 nm after filtering the collected 3 mL with 0.45 μm syringe filter, without further dilution.

FIGS. 9($a$), 9($b$), and 9($c$) presents the API release from the blends containing 5, 3, and 1 wt % of API in the order. The tablet tensile strength (evaluated with a texture analyzer, Texture Technologies Corp., USA) and moisture content which was analyzed with a Thermo-gravimetric analysis (TGA/DSC1/SF STAR tare system, Mettler Toledo Inc., OH, USA) were not statistically different between the formulations of the blends (see FIG. 8). However, API release rates were significantly different, showing notable improvement in the API release rate compared to the blends containing uncoated API.

The comprehensive analysis of the low API loaded cohesive and fine blends, which contain either hydrophobic or hydrophilic silica in the range of 0.007 to 0.116 wt %, demonstrated the feasibility of processing cohesive and fine multi-component pharma relevant powders without relying on the wet-granulation process, enabling a direction compaction process with improved flowability, content uniformity, and API release rate thereby promoting the enhance product quality with case of process operation.

Such improvements are also beneficial for the encapsulation processes, where the process requires powder flowability greater than FFC of 6 and bulk density greater than 0.45 g/mL. As summarized in Table 5, the dry coating of the minor component (API) with either a hydrophobic or hydrophilic silica of fixed weight percent satisfied the requirements for effective encapsulation process, which is unexpected and surprising since very minute amount of silica was used.

Example 5 (Coarse and Weakly Cohesive Multi-Component Blend Varying Mixing Time): Synergistic Effect from the Dry Coating and Mixing on the Coarse (≥100 μm) Particle Sized Multi-Component Blend of Low API Loading—Blend Agglomerate Reduction Example 5 discusses the reduction in the agglomerate size of multi-component coarse and weakly cohesive low API loaded blends at different mixing times once the APIs are coated.

Five components of disparate particle sized (10~120 μm) blends were studied in this study. FIG. 32 provides the physical properties of the employed components. As the model active pharmaceutical ingredient (API), ibuprofen (Ibu), which belongs in BCS II classification was selected.

The ibuprofen was milled from the mean particle size of 50 μm to 10-15 μm using a fluidized energy mill (FEM, Pharmaceutical Micronizer Fluidized Energy Grinding Jet mill, Sturtevant Inc., Hanover, Massachusetts). The feeding rate, feeding pressure and grinding pressure were set as 8 g/min, 30 psi, and 25 psi, respectively. Micronization of the powders can be done with other than the described FEM method. The summarized mean particle size and particle density for the blend components are shown in FIG. 32.

Prior to the blending, the milled Ibu was dry coated with either Acrosil R972P or Acrosil A200 using a high-intensity vibratory mixer (LabRAM, Resodyn, USA) at the intensity of 75 times the gravitational force and 60 Hz for 5 minutes. The dry coating could be done with other methods. A 300 mL screw top plastic container was used for the dry coating. For each dry coating run, about 66% of the container volume was taken up by powder, which comprised the milled Ibu and nano fumed silica.

For the dry coating formulation, four cases were prepared. In the first case, fixed wt % of either hydrophobic (R972P) or hydrophilic (A200) silica was used as the dry coating agent (guest particles). For the second case, fixed surface area coverage (SAC) % of either hydrophobic (R972P) or hydrophilic (A200) was used. The dry coating formulation is summarized in FIG. 33. The SAC % calculation was done using techniques known to those skilled in the art. FIGS. 1(a) through 1(e) which were discussed in Example 1, represent the dry coated API used for Example 5 as well.

To prepare blends, mixing parameters such as the order of filling each constituent, fill level, mixing intensity, and mixing time were held constant. The powder blend, except for MgSt, was hand mixed before adding it to a 4-pint V-shaped container. For the hand mixing process, the pre-weighted components were added in a 1-gallon ziplock plastic bag and were gently shaken a couple of times, where the total time spent in the bag was less than ten seconds. MgSt was added during the last 90 seconds of mixing time. The filling level was held constant at ~37% of the capacity by volume (280 g of blend weight). The mixing times were varied from 5 to 60 minutes to investigate the impact from the different mixing times on the blends agglomerate size. The mixing rotational speed was fixed at 25 rpm. The blending could be done with any other methods. FIG. 34 presents the formulation details for the resulting blends. The presented formulation includes 1 and 5 wt % API loaded blends, but the API loading needs are not limited to these two, could be anything in between 1 and 5 or greater than 5 wt %, extending to 30% or higher.

The primary particle size of API before and after dry coating and the resulted blends were evaluated using a compressed air dispersion method basis a laser diffraction particle sizer, Rodos/Helos (Sympatec Inc., NJ). The agglomerate particle size distributions of the API before and after the dry coating and blends were evaluated using a gravity dispersion-based dynamic imaging particle sizer, Gradis/QicPic (Sympatec Inc., NJ). Unlike traditional sieving or SEM-imaging or optical microscope based agglomerate size estimation, employed Gradis/QiPic provides statistically representative and repeatable full agglomerate particle size distribution based on more than $10^7$ particle image analysis while gentling dispersing the powders minimizing the impact on the agglomerates and preserving their original state as close as possible.

Figure 10A:
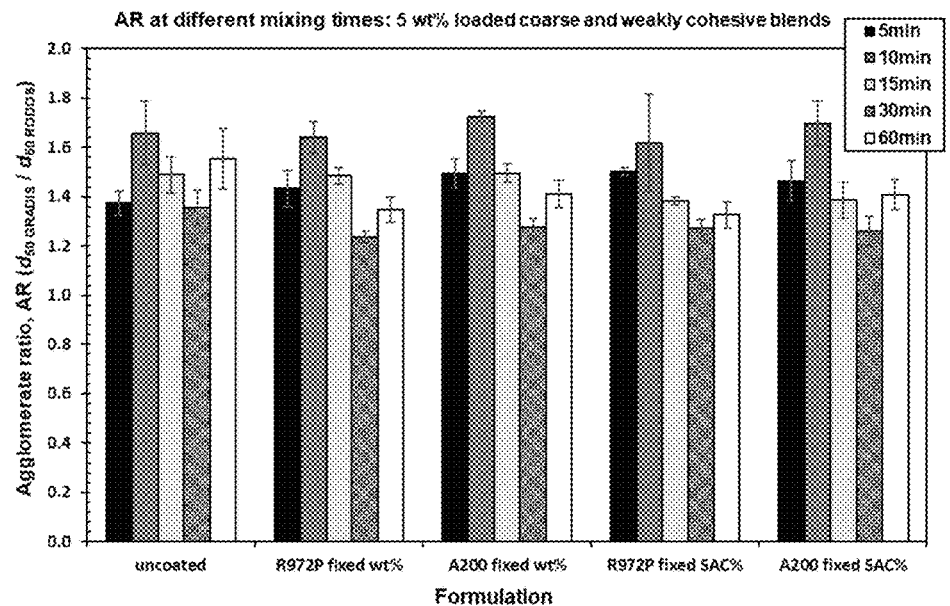
FIGS. 10a-10b are illustrations of a visual comparison of the dry coating and mixing impact on the agglomeration state of the low API loaded coarse and weakly cohesive blends at varying dry coating formulations and different length of mixing times.
Figure 10B:
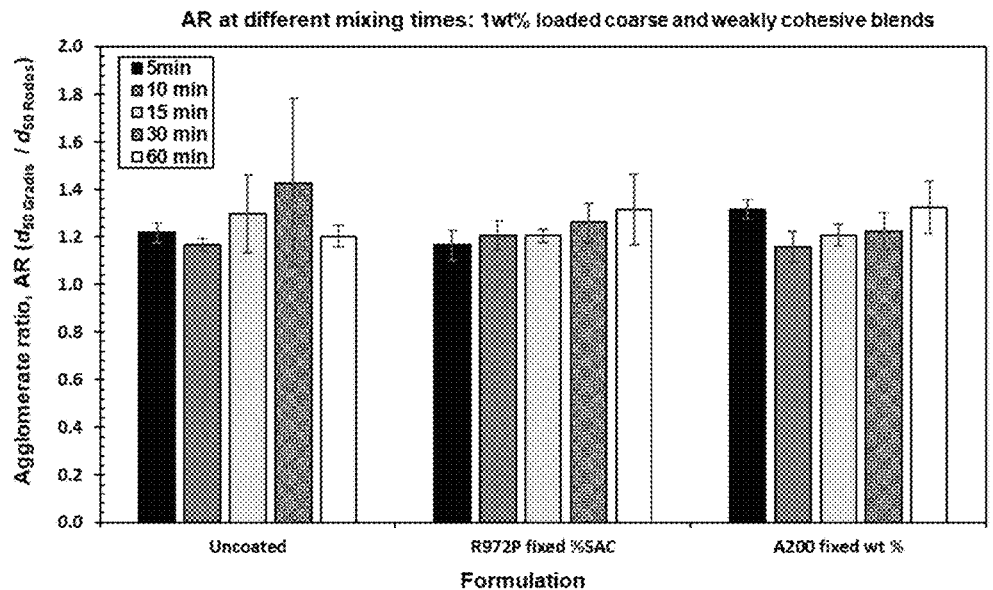

The summarized characteristic primary and agglomerated particle size distributions for the uncoated and dry coated APIs are shown in FIG. 35 and the summarized results for the blends are shown in FIG. 36 for 5 wt % API loaded coarse and weakly cohesive blends and FIG. 37 for 1 wt % API loaded coarse and weakly cohesive blends. Based on the evaluated primary and agglomerate particle size assessments, the agglomerate ratio ($d_{50\ Gradis}/d_{50\ Rodos}$) was found and plotted as shown in FIGS. 10 (a) and 10(b). Owing to the coarse sizes of the blends and their weak cohesiveness, after the dry coating, only marginal improvement in the agglomerate size reduction was achieved. Unexpectedly, the standard deviation calculated for $d_{50}$ Gradis significantly reduced for all mixing times when the API in the 1 wt % blends was dry coated, and the reduction increased as the mixing time increased. In addition, for 1 wt % blends with dry coated API, which contain the either hydrophobic or hydrophilic silica between 0.012 to 0.023 wt % demonstrated significant agglomerate particle size span reduction as shown in FIG. 37. The change in the agglomerate particle size span indicates that with the dry coating, the blend's agglomerate PSD reduced its width, which affects the mechanical properties of the powders when the blends are subjected to compaction. More uniform compaction behavior is expected with a reduced agglomerate particle size span.

Example 6 (Coarse and Weakly Cohesive Multi-Component Blend Varying Mixing Time): Synergistic Effect from the Dry Coating and Mixing on the Coarse (≥100 μm) Particle Sized Multi-Component Blend of Low API Loading—Blend Flowability and Bulk Density Improvements Identical blends used in Example 5 were using an Example 6 to demonstrate the increase in the blend flowability and bulk density improvements.

Processability (flowability and bulk density) of the uncoated and dry coated API and the blends including the placebo were evaluated using a powder rheometer, FT4 (Freeman Technology, UK) under 3.0 kPa of pre-compaction pressure for shear testing. The processability of the powders can also be assessed using a ring shear tester or other types of powder rheometer.

The bulk properties assessments including bulk density, bulk cohesion, and flowability are summarized in FIG. 38 for 5 wt % loaded blends. The results for 1 wt % loaded blends are summarized in FIG. 39. For all cases of 5 wt % and 1 wt % loaded blends at different mixing times and dry coating formulation, although the concentration of the silica is minute in its amount ranging from 0.116 to 0.012 wt %, the bulk densities of the blends were all improved, increasing from 0.42 g/mL to as high as 0.50 g/mL.

Figure 11:
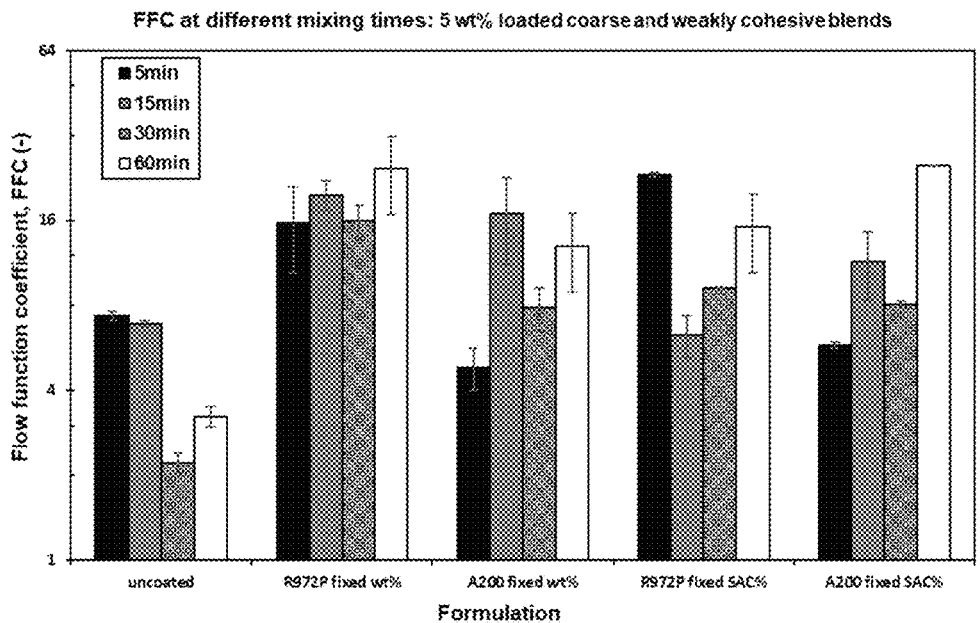
FIGS. 11a-11b are bar graphs illustrating synergistic impact from the dry coating and mixing on the flowability of the low API loaded coarse and weakly cohesive blends.
Figure 11B:
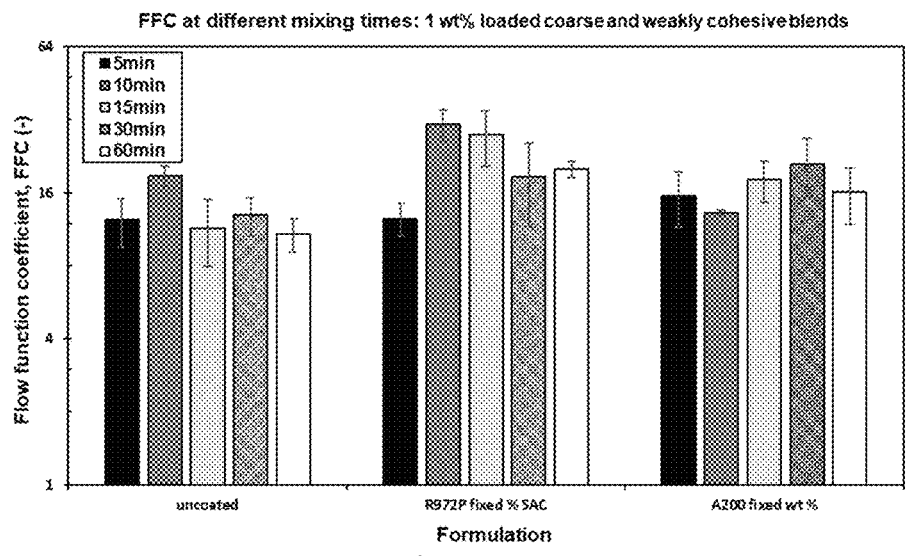

But most importantly, the notable improvement in FFC were observed with 5 wt % blends as the mixing time increased, as shown in FIG. 11(a). The increase was highest with Acrosil R972P 0.116 wt % in the blend. The increase in the FFC was observed with increase in the mixing time, while the FFC of the blends with 5 wt % loaded uncoated API blends FFC worsened from 7 to as low as 2. This infer that during the extended mixing time, due to the collisions between the powders, they are be subjected to charging, increasing their bulk cohesiveness. However, with the dry coated API, such effect seemed to significantly subdue overall improving the bulk powder flowability. Likewise, for the 1 wt % loaded blends (sec FIG. 11(b)), combined with the dry coating and mixing effect, the FFC of the blends with the dry coated API show notable improvement in FFC, following similar trend as observed in FIG. 11(a).

In most cases, the FFC of the blends with the dry coated API achieved 6, with bulk density above 0.45 g/mL, satisfy requirements for direct compression tableting, easier encapsulation, and sachet filling.

Example 7 (Coarse and Weakly Cohesive Multi-Component Blend Varying Mixing Time): Synergistic Effect from the Dry Coating and Mixing on the Coarse (≥100 µm) Particle Sized Multi-Component Blend of Low API Loading—Blend Content Uniformity Improvement Identical blends used in Examples 5 and 6 were used in Example 7 to demonstrate the increase in the blend content uniformity due to the synergistic effect from the dry coating and mixing.

Figure 12A:
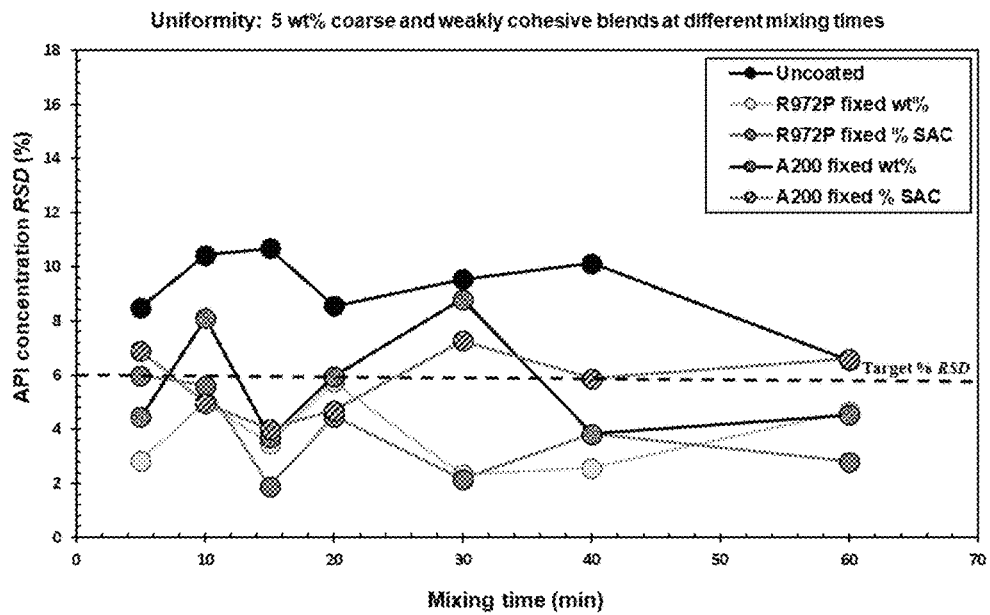
FIGS. 12a-12b are illustrations of improved blend uniformity for the weakly cohesive and coarse blends of low API loaded blends with the dry coating of the API.
Figure 12B:
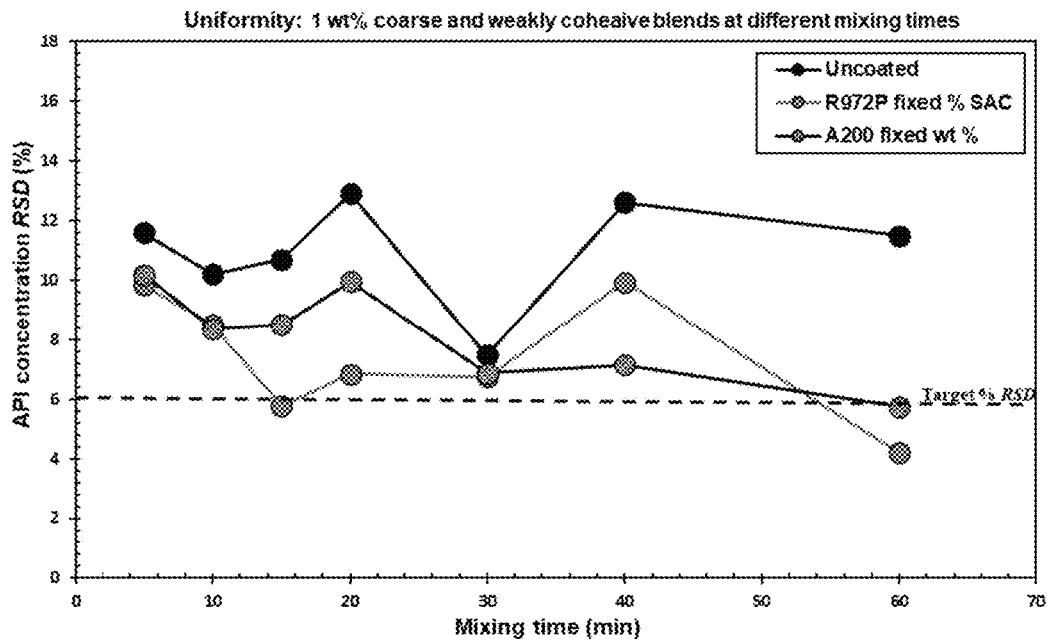

The content uniformity of the prepared blends was assessed and summarized in FIGS. 12(a) and 12(b) for 5 wt % and 1 wt % loaded coarse and weakly cohesive multi-component blends. Upon evaluating the blend uniformity, API concentration assay analysis was conducted. The powder sampling was done with a spinning riffler (SP-230, Gilson Company, INC., USA). 400 mg of collected powder samples were dissolved in a 100 mL pH 7.2 phosphate buffer over 24 hours. The dissolved API concentration in the buffer solution was measured with UV spectrophotometry (Thermo Fisher Scientific Inc., USA). To determine the uniformity of the blends, the averaged API concentration and relative standard deviation (RSD) in % was calculated following USP <905> guideline. Overall, to the great surprise, the blend uniformity was significantly improved at all mixing times. Especially for 5 wt % loaded blends, the target RSD was satisfied at most cases except few exceptions.

Figure 13A:
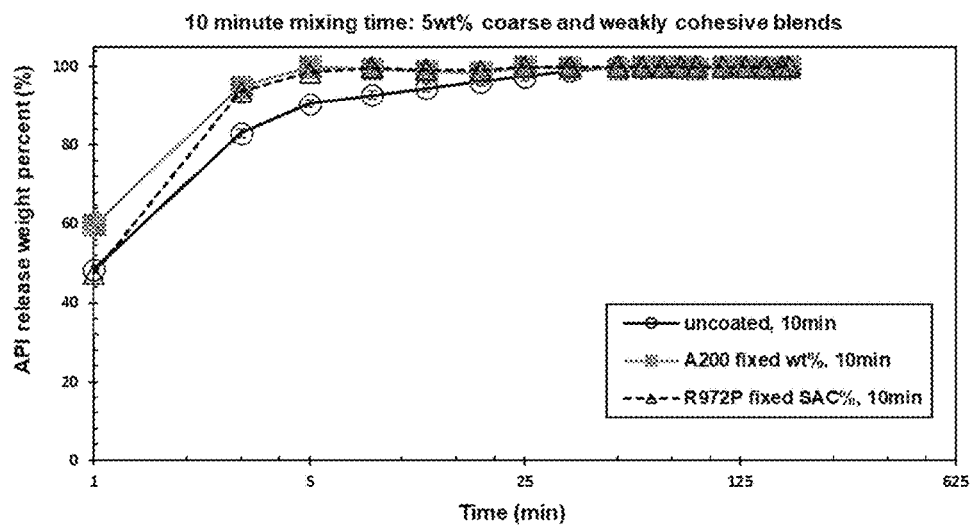
FIGS. 13a-13b are illustrations of faster API release rate from the tablets even with the hydrophobic silica coating due to the agglomerate size reduction impact of both the API and the blends.
Figure 13B:
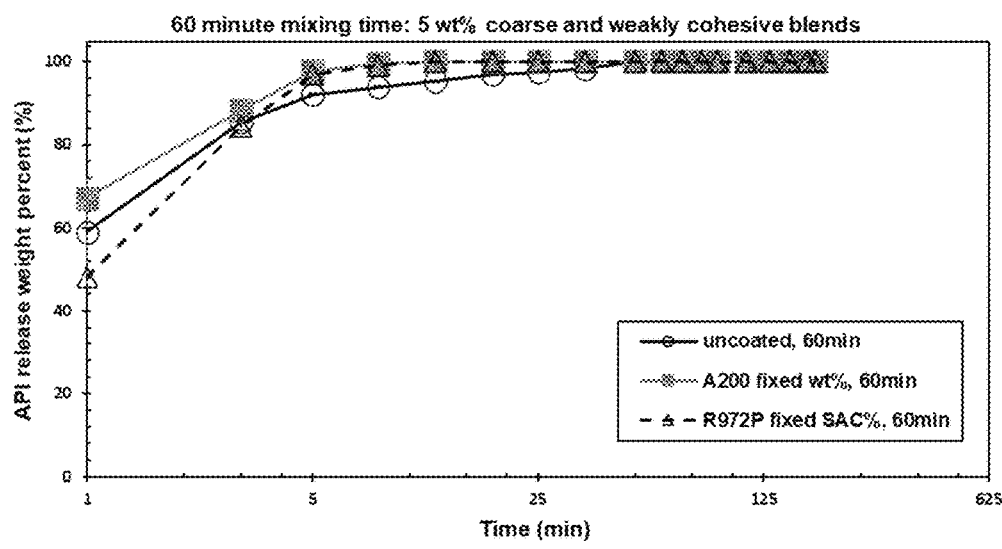

Example 8 (Coarse and Weakly Cohesive Multi-Component Blend Varying Mixing Time): Synergistic Effect from the Dry Coating and Mixing on the Coarse (≥100 µm) Particle Sized Multi-Component Blend of Low API Loading—API Release Rate Improvement Identical blends used in Examples 5, 6 and 7 were used in Example 8 to demonstrate the increase in the API release rate. For the demonstration, selective cases of 5 wt % loaded coarse and weakly cohesive multi-component were evaluated. However, the similar API release rate profiles are expected from the 1 wt % loaded coarse and weakly cohesive multi-component blends as well. For the dissolution analysis, identical procedures and methods used in Example 4 were adopted. FIG. 13(a) and FIG. 13(b) are the resulted API release rate from the prepared 400 mg tablets.

Carver platen press (Carver, Inc., USA) with a 0.5-inch inner diameter stainless die and a flat-faced round punch was used to prepare 400 mg tablets under ~2.0 metric ton (equivalent to ~155 MPa) compaction pressure. The compaction condition could be varying.

To measure API release rate USP II paddle method was used with pH 7.2 phosphate buffer as the dissolution medium. To ensure the sink condition during the dissolution process and adequate absorbance peak response via UV-vis analysis without further dilution (UV-vis spectrometer, Thermo Scientific, USA), 500 mL dissolution medium was used, considering both the low API dosage and the solubility of 2 mg of Ibu per 1 mL of PBS buffer in PBS pH 7.2 buffer at the ambient condition. Both the temperature of the system and the rotating speed of the paddle were fixed at 37° C.±0.2° C. and 50 rpm, respectively, during dissolution. At the pre-determined time intervals, 3 mL of samples were drawn, while replenishing the buffer amount by immediately adding 3 mL make-up solvent.

The absorbance of the sample was measured in duplicate at the wavelength of 221 nm after filtering the collected 3 mL with 0.45 µm syringe filter, without further dilution. FIGS. 13(a) and 13(b) presents the API release from the blends at different mixing times and dry coating formulations for 5 wt % loaded coarse and weakly cohesive multi-component blends.

The tablet tensile strength (evaluated with a texture analyzer, Texture Technologies Corp., USA) and moisture content which was analyzed with a Thermo-gravimetric analysis (TGA/DSC1/SF STAR$^e$ tare system, Mettler Toledo Inc., OH, USA) were not statistically different between the formulations of the blends. However, API release rates were notably different, showing notable improvement in the API release rate compared to the blends containing uncoated API.

Example 9 (Fine and Cohesive Multi-Component Blend Varying Mixing Time): Synergistic Effect from the Dry Coating and Mixing on the Fine (≤35 µm) Particle Sized Multi-Component Blend of Low API Loading—Blend Agglomerate Reduction Example 9 discusses the reduction in the agglomerate size of multi-component fine and cohesive low API loaded blends at different mixing times once the APIs are coated.

Five components of disparate particle sized (10~30 µm) blends were studied in this study. FIG. 27 provides the physical properties of the employed components. As the model active pharmaceutical ingredient (API), ibuprofen (Ibu), which belongs in BCS II classification was selected.

The as received ibuprofen was milled from the mean particle size of 50 µm to 10-15 µm using a fluidized energy mill (FEM, Pharmaceutical Micronizer Fluidized Energy Grinding Jet mill, Sturtevant Inc., Hanover, Massachusetts). The feeding rate, feeding pressure and grinding pressure were set as 8 g/min, 30 psi, and 25 psi, respectively. Micronization of the powders can be done with other than the described FEM method. In Example 9, the components used in the Example 1 were used. For component properties detail, refer to FIG. 27.

Prior to the blending, the milled Ibu was dry coated with either Acrosil R972P or Acrosil A200 using a high-intensity vibratory mixer (LabRAM, Resodyn, USA) at the intensity of 75 times the gravitational force and 60 Hz for 5 minutes. The dry coating could be done with other methods. A 300 mL screw top plastic container was used for the dry coating. For each dry coating run, about 66% of the container volume was taken up by powder, which comprised the milled Ibu and nano fumed silica.

For the dry coating formulation, four cases were prepared. In the first case, fixed wt % of either hydrophobic (R972P) or hydrophilic (A200) silica was used as the dry coating agent (guest particles). For the second case, fixed surface area coverage (SAC) % of either hydrophobic (R972P) or hydrophilic (A200) was used. The dry coating formulation is summarized in FIG. 33. The SAC % calculation was done following the previous works [5, 6]. The SAC % calculation was done as previously described and known by those skilled in the art. FIGS. 1(a) through 1(e) which were discussed in Example 1, represent the dry coated API used for Example 9 as well.

Identical mixing procedures and methods from Example 5 were used in Example 9 to prepare blends. The filling level was held constant at ~37% of the capacity by volume (280 g of blend weight). The mixing times were varied from 5 to 60 minutes to investigate the impact from the different mixing times on the blends agglomerate size. The mixing rotational speed was fixed at 25 rpm. The blending could be done with any other methods. Table 14 presents the formulation details for the resulting blends. The presented formulation includes 1 and 5 wt % API loaded blends, but the API loading needs are not limited to these two, could be anything in between 1 and 5 or greater than 5 wt %, extending to 30% or higher.

Figure 14A:
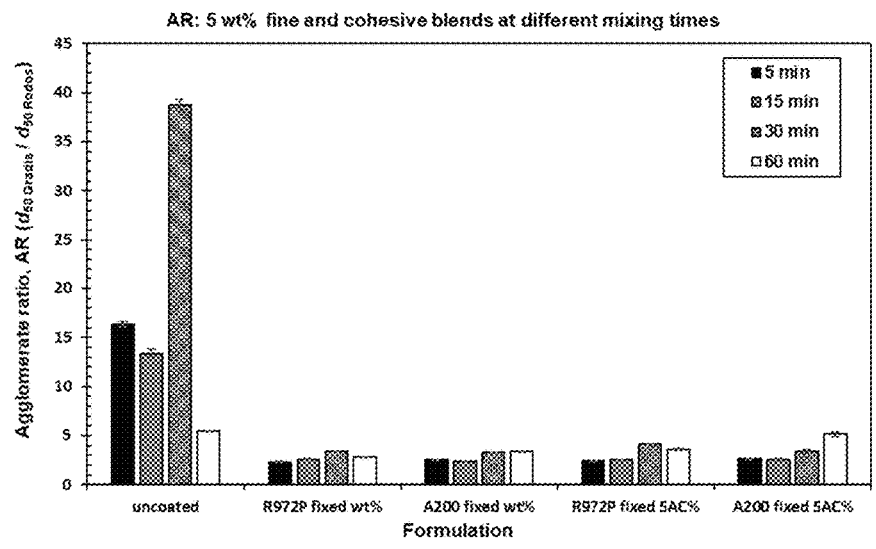
FIGS. 14a-14b are illustrations of a visual comparison of the dry coating and mixing impact on the agglomeration state of the low API loaded cohesive and fine blends at varying dry coating formulations and different length of mixing times.
Figure 14B:
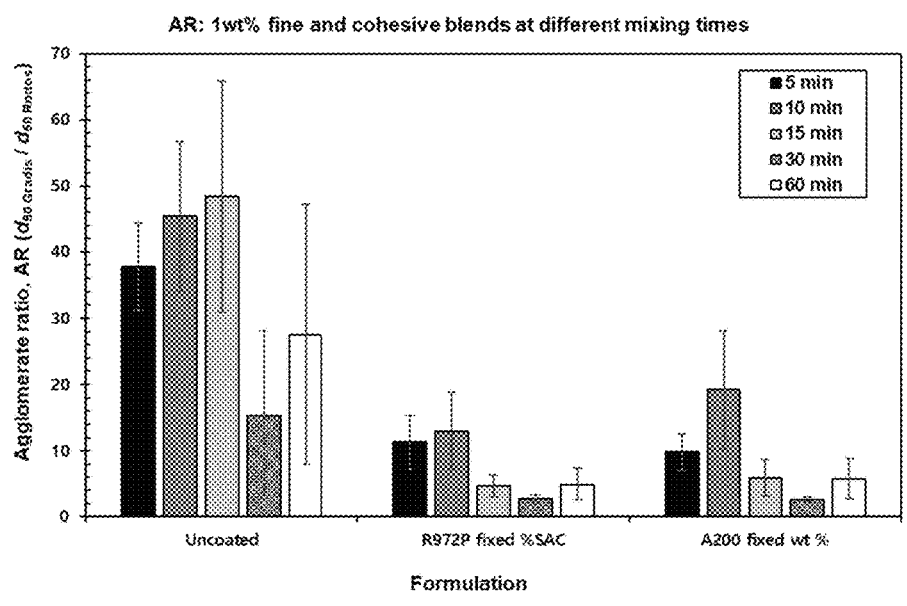

To evaluate primary and agglomerate particle sizes of the API before blending and multi-component blends at different mixing times, same methods from Example 5 were used in Example 9. The summarized primary and agglomerate size results for 5 wt % loaded fine and cohesive blends are shown in FIG. 41. FIG. 42 presents the results for 1 wt % API loaded fine and cohesive blends. Based on the evaluated primary and agglomerate particle size assessments, the agglomerate ratio ($d_{50\ Gradis}/d_{50\ Rodos}$) was found and plotted as shown in FIGS. 14(a) and 14(b). Based on the FIG. 41 and FIG. 42, notable reduction in the agglomerate particle size spans were observed for both loading cases, expecting more predictable compaction behavior due to the synergistic effect from the dry coating and mixing. Also, FIGS. 14(a) and 14(b) demonstrate notable reduction in the agglomerate size despite the minute amount of silica added in the blends, which ranges from 0.116 to 0.012 wt % of silica.

Example 10 (Fine and Cohesive Multi-Component Blend Varying Mixing Time): Synergistic Effect from the Dry Coating and Mixing on the Fine (≤35 μm) Particle Sized Multi-Component Blend of Low API Loading—Blend Flowability and Bulk Density Improvements Identical blends used in Examples 9 were used in Example 10 to demonstrate the increase in the processability (flowability and bulk density) improvement due to the synergistic effect from the dry coating and mixing.

Processability (flowability and bulk density) of the uncoated and dry coated API and the blends including the placebo were evaluated using a powder rheometer, FT4 (Freeman Technology, UK) under 3.0 kPa of pre-compaction pressure for shear testing. The processability of the powders can also be assessed using a ring shear tester or other types of powder rheometer.

The bulk properties assessments including bulk density, bulk cohesion, and flowability are summarized in FIG. 43 for 5 wt % loaded blends. The results for 1 wt % loaded blends are summarized in FIG. 44. For all cases of 5 wt % and 1 wt % loaded blends at different mixing times and dry coating formulation, although the concentration of the silica is minute in its amount ranging from 0.116 to 0.012 wt %, the bulk densities of the blends were all improved, increasing from 0.42 g/mL to as high as 0.50 g/mL, favorably supporting direction compaction and encapsulation processes.

Figure 15A:
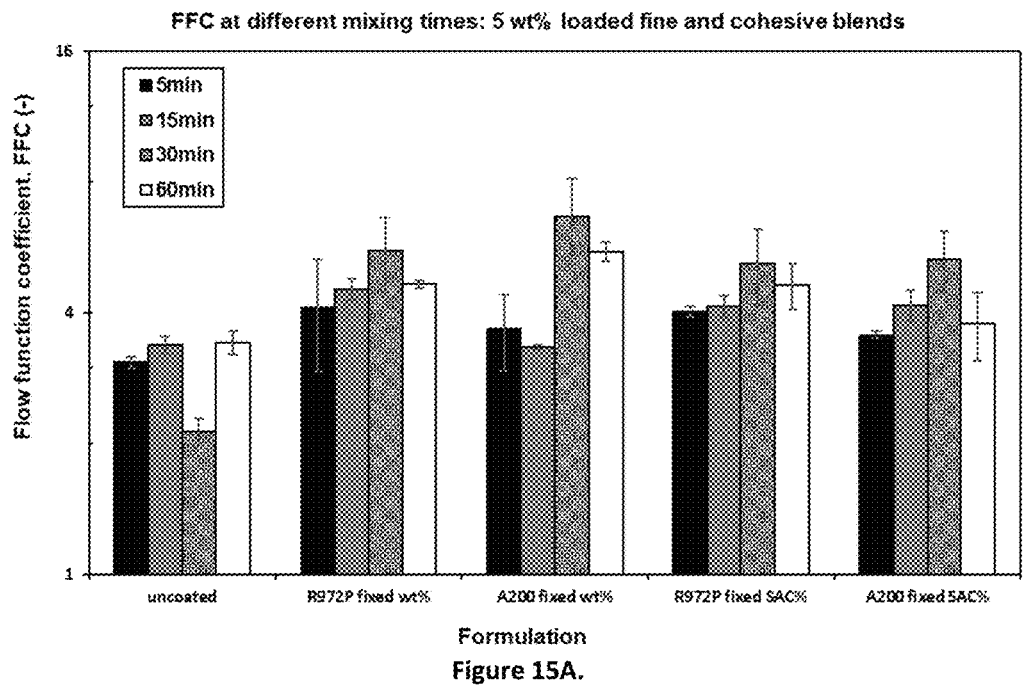
FIGS. 15a-15b are bar graphs illustrating synergistic impact from the dry coating and mixing on the flowability of the low API loaded cohesive and fine blends.
Figure 15B:
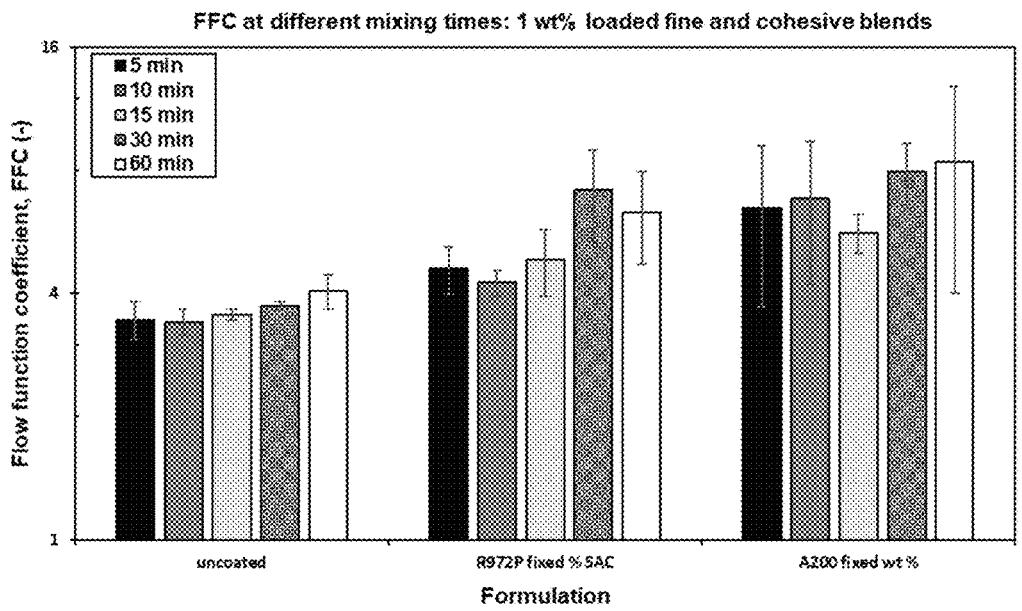

But most importantly, the notable improvements in FFC were observed with 5 wt % blends as the mixing time increased, as shown in FIG. 15(a). The increase was highest with Acrosil A200 0.116 wt % in the blend. The increase in the FFC was observed with increase in the mixing time, while the FFC of the blends with 5 wt % loaded uncoated API blends FFC worsened from 3 to as low as 2. This implies that during the extended mixing time, due to the collisions between the powders, they are be subjected to charging, increasing their bulk cohesiveness. However, with the dry coated API, such effect seemed to significantly subdue overall improving the bulk powder flowability. Likewise, for the 1 wt % loaded blends (sec FIG. 15(b)), combined with the dry coating and mixing effect, the FFC of the blends with the dry coated API show notable improvement in FFC, following similar trend as observed in FIG. 15(a). Interestingly for both 5 and 1 wt % blends, the blend flowability improved by one flow regime, enabling both direction compaction and encapsulation processes. The FFC improvement were in general, higher in 1 wt % where the silica concentration was as low as 0.012 wt %.

Example 11 (Fine and Cohesive Multi-Component Blend Varying Mixing Time): Synergistic Effect from the Dry Coating and Mixing on the Fine (≤35 μm) Particle Sized Multi-Component Blend of Low API Loading—Blend Content Uniformity Improvement Identical blends used in Examples 9 and 10 were used in Example 11 to demonstrate the increase in the blend content uniformity due to the synergistic effect from the dry coating and mixing.

Figure 16A:
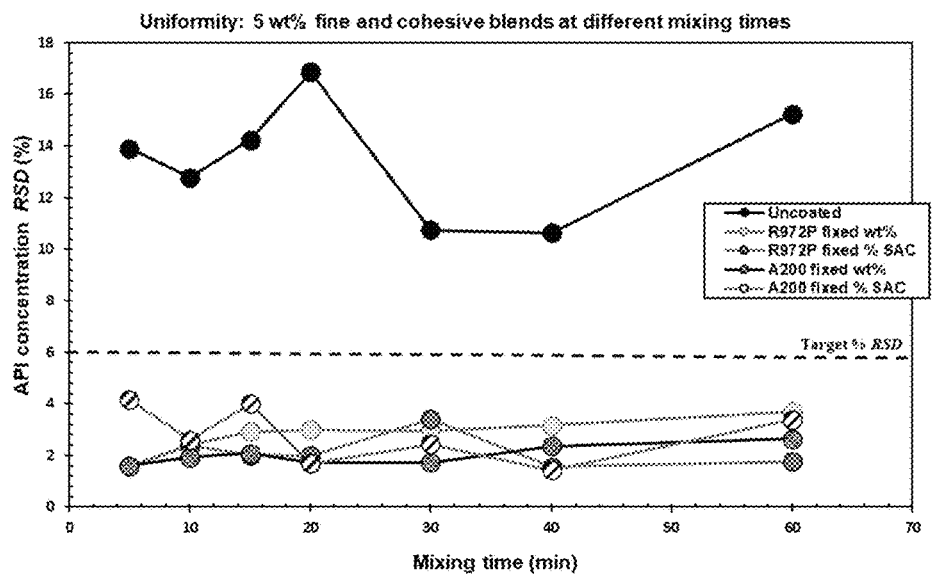
FIGS. 16a-16b illustrate the improved content uniformity of low API loaded cohesive and fine blends with the inclusion of the dry coated API, wherein blends were prepared by mixing at different length of mixing times.
Figure 16B:
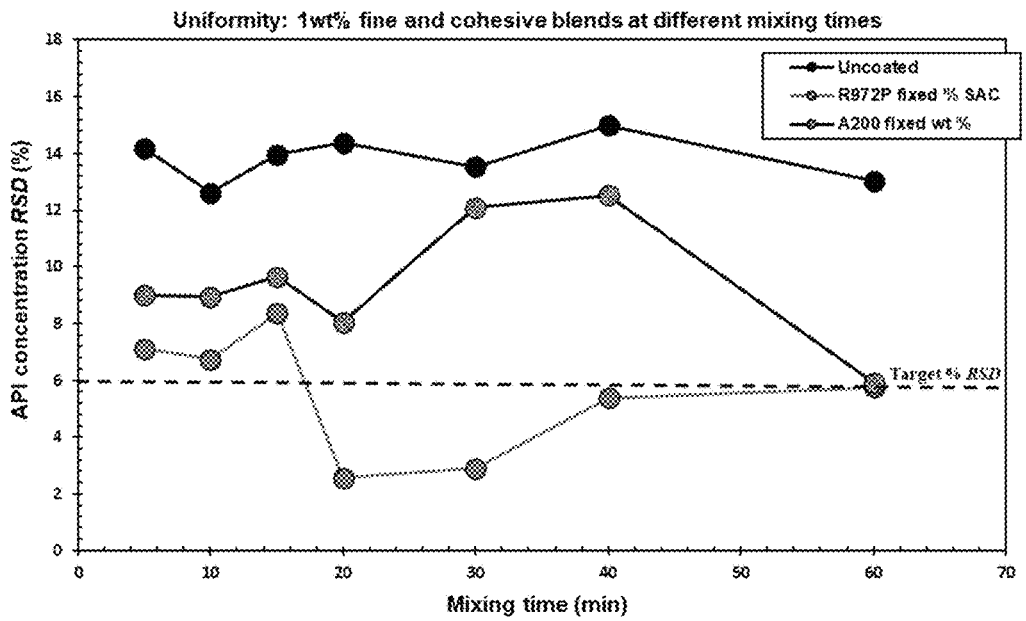

The content uniformity of the prepared blends was assessed and summarized in FIGS. 16(a) and 16(b) for 5 wt % and 1 wt % loaded fine and cohesive multi-component blends. Upon evaluating the blend uniformity, API concentration assay analysis was conducted. The powder sampling was done with a spinning riffler (SP-230, Gilson Company, INC., USA). 400 mg of collected powder samples were dissolved in a 100 mL pH 7.2 phosphate buffer over 24 hours. The dissolved API concentration in the buffer solution was measured with UV spectrophotometry (Thermo Fisher Scientific Inc., USA). To determine the uniformity of the blends, the averaged API concentration and relative standard deviation (RSD) in % was calculated following USP <905> guideline. Overall, to the great surprise, the blend uniformity was significantly improved at all mixing times. Especially for 5 wt % loaded blends, the target RSD was satisfied for all different mixing times.

Figure 17A:
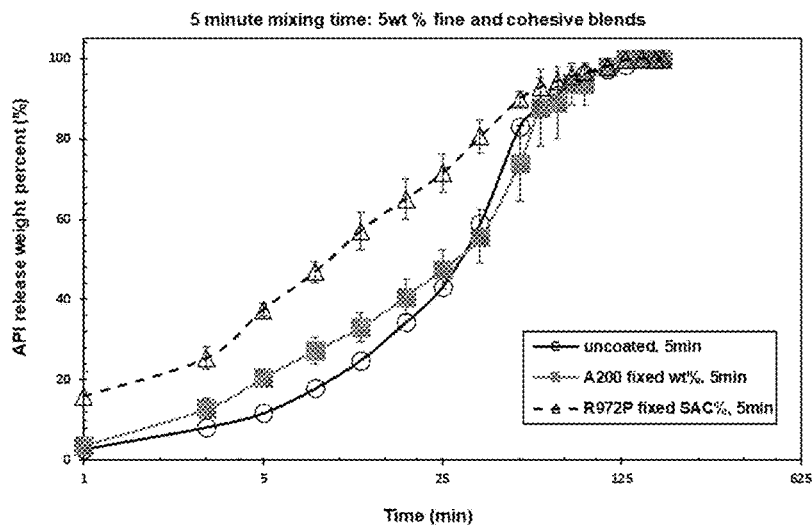
FIGS. 17a-17b illustrate the increase in the API release rate from the tablets with the dry coated API where the API release rate was improved even with the hydrophobic silica coating, due to the outweighing impact from the reduced particle agglomeration.
Figure 17B:
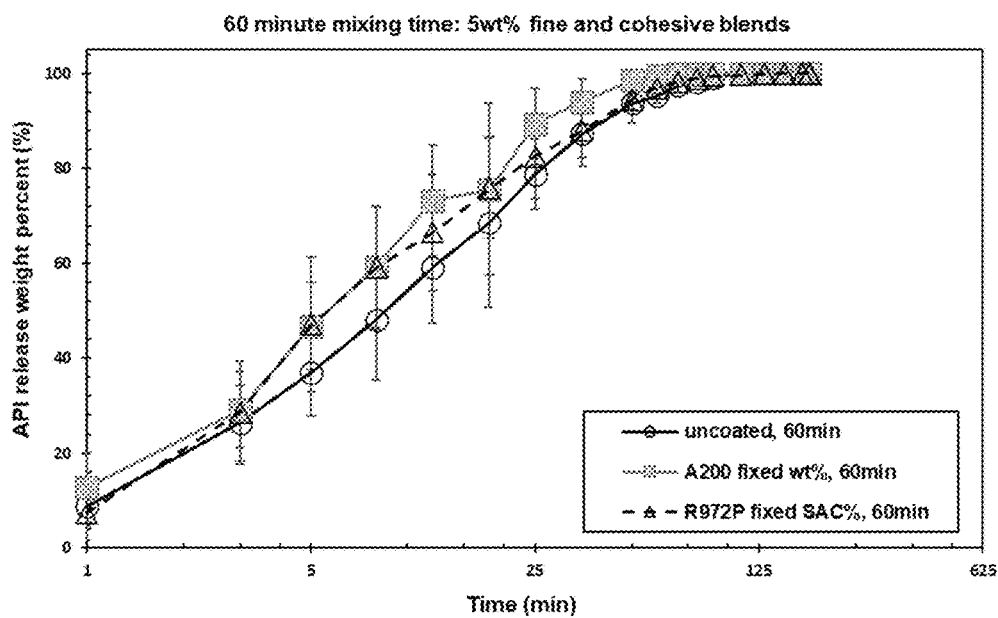
Figures 18A, 18B, 18C, 18D, 18E, 18F:
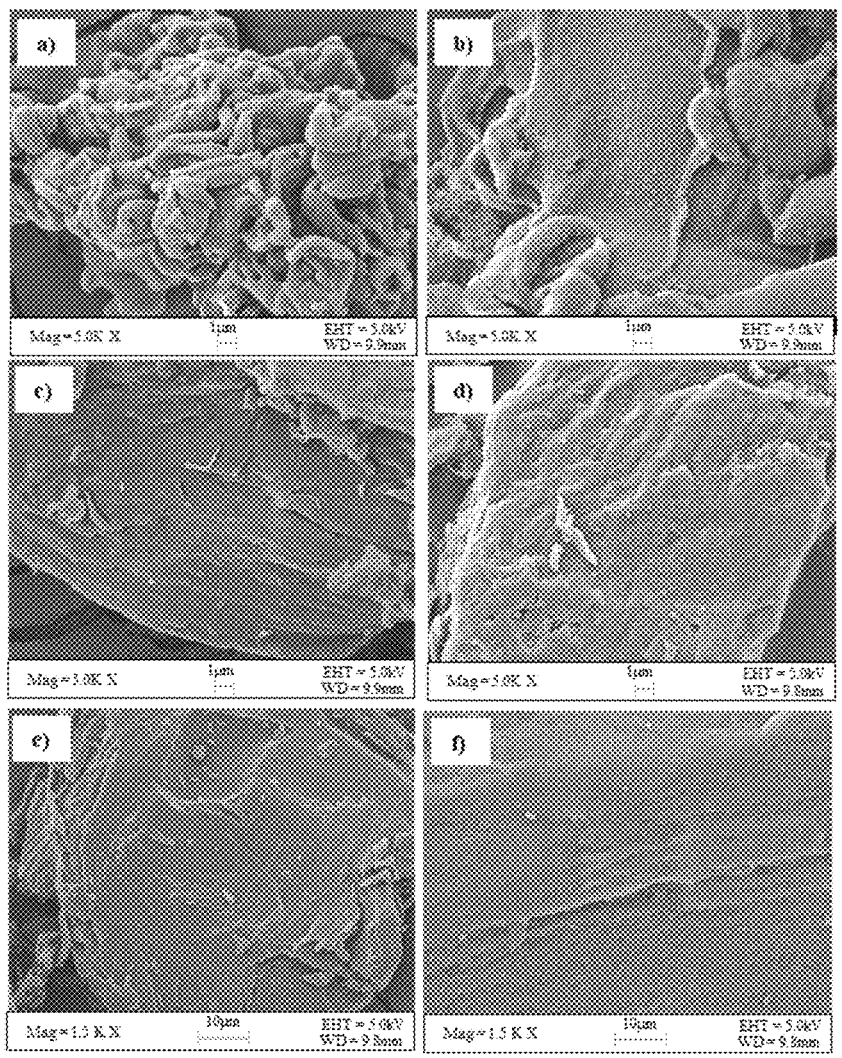
FIGS. 18a-18f are SEM images of disintegrants before and after dry coating.
Figure 19A:
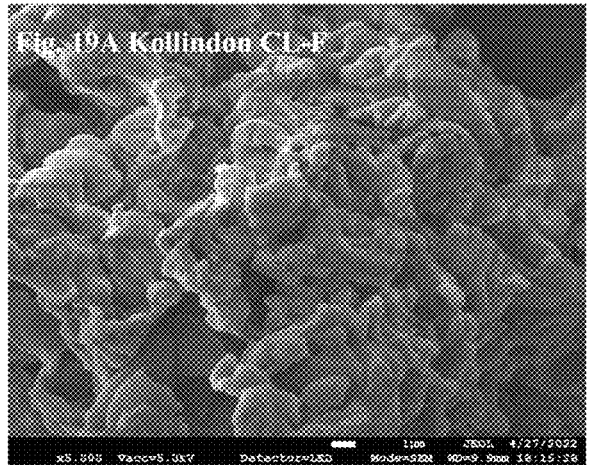
FIGS. 19a-19d are SEM images of various uncoated and coated particles.
Figure 19B:
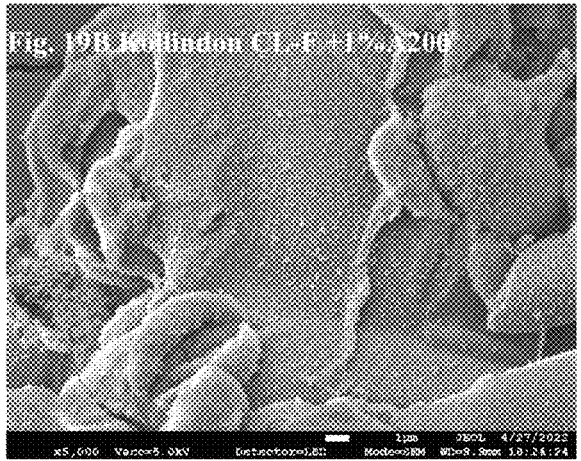
Figure 19C:
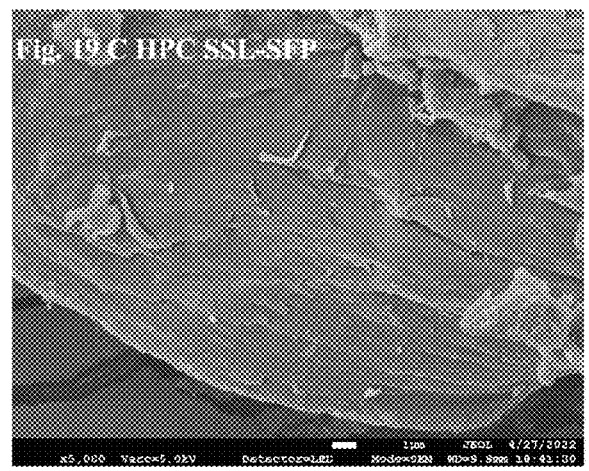
Figure 19D:
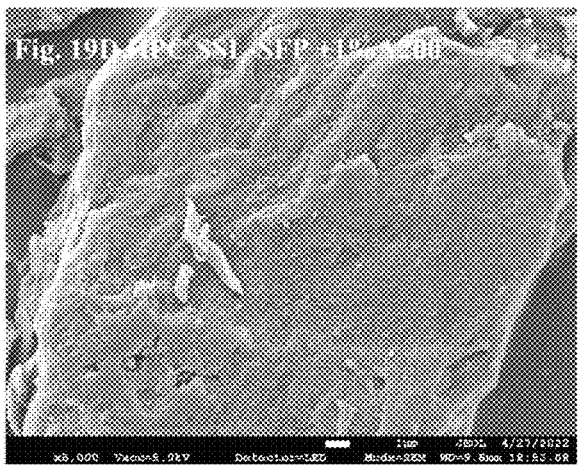

Example 12 (Fine and Cohesive Multi-Component Blend Varying Mixing Time): Synergistic Effect from the Dry Coating and Mixing on the Fine (≤35 μm) Particle Sized Multi-Component Blend of Low API Loading—API Release Rate Improvement Identical blends used in Examples 9, 10 and 11 were used in Example 12 to demonstrate the increase in the API release rate. For the demonstration, selective cases of 5 wt % loaded fine and cohesive multi-component were evaluated. However, the similar API release rate profiles are expected from the 1 wt % loaded fine and cohesive multi-component blends as well. For the dissolution analysis, identical procedures and methods used in Example 4 were adopted. FIG. 17(a) and FIG. 17(b) are the resulted API release rate from the prepared 400 mg tablets.

Carver platen press (Carver, Inc., USA) with a 0.5-inch inner diameter stainless die and a flat-faced round punch was used to prepare 400 mg tablets under ~1.0 metric ton (equivalent to ~77 MPa) compaction pressure. The compaction condition could be varying.

To measure API release rate USP II paddle method was used with pH 7.2 phosphate buffer as the dissolution medium. To ensure the sink condition during the dissolution process and adequate absorbance peak response via UV-vis analysis without further dilution (UV-vis spectrometer, Thermo Scientific, USA), 500 mL dissolution medium was used, considering both the low API dosage and the solubility of 2 mg of Ibu per 1 mL of PBS buffer in PBS pH 7.2 buffer at the ambient condition. Both the temperature of the system and the rotating speed of the paddle were fixed at 37° C.±0.2° C. and 50 rpm, respectively, during dissolution. At the pre-determined time intervals, 3 mL of samples were drawn, while replenishing the buffer amount by immediately adding 3 mL make-up solvent.

The absorbance of the sample was measured in duplicate at the wavelength of 221 nm after filtering the collected 3 mL with 0.45 μm syringe filter, without further dilution. FIGS. 13(a) and 13(b) presents the API release from the blends at different mixing times and dry coating formulations for 5 wt % loaded fine and cohesive multi-component blends.

The tablet tensile strength (evaluated with a texture analyzer, Texture Technologies Corp., USA) and moisture content which was analyzed with a Thermo-gravimetric analysis (TGA/DSC1/SF STAR$^e$ tare system, Mettler Toledo Inc., OH, USA) were not statistically different between the formulations of the blends. However, API release rates were notably different, showing notable improvement in the API release rate compared to the blends containing uncoated API.

Example 13 (Fine and Cohesive Multi-Component Blend Varying Mixing Time): Synergistic Effect from the Dry Coating and Mixing on the Fine (≤35 μm) Particle Sized Multi-Component Blend of Higher (30%) API Loading—Blend Flowability Improvement Example 13 discusses the improvement in the blend flowability of multi-component fine and cohesive high API loaded blends at different mixing times once the APIs are coated.

Five components of disparate particle sized (10~30 μm) blends were studied in this study. FIG. 27 provides the physical properties of the employed components. As the model active pharmaceutical ingredient (API), ibuprofen (Ibu), which belongs in BCS II classification was selected.

Sample preparation and blending preparation followed the identical methods and procedures described in Example 9. FIG. 45 presents the blend formulation details. The example blends shown in Example 13 tested 30% API loaded cohesive and fine multi-component blends. However, the API loading could be higher than 30%.

Processability (flowability and bulk density) of the uncoated and dry coated API and the blends including the placebo were evaluated using a powder rheometer, FT4 (Freeman Technology, UK) under 3.0 kPa of pre-compaction pressure for shear testing. The processability of the powders can also be assessed using a ring shear tester or other types of powder rheometer.

The summarized results are shown FIG. 46, which demonstrates linear increase in the powder flowability with the increase in the number of rotations. This is a remarkable finding where the unexpected linear increase in the synergistic impact from the dry coating and mixing time as the number of rotations increases for the blending.

Example 14 Synergistic Effect from the Dry Coated Excipient on Binary or Ternary Blend of High API Loading of Up to 95 wt %—Blend Bulk Density and Flowability Improvement Example 14 concerns with API loading of 90 wt % and up to 95 wt %. It determines the bulk density and FFC of several blends using uncoated and dry coated excipients. Prior to the blending, as received excipient was dry coated with 1 wt % Acrosil A200 (A200) using a high-intensity vibratory mixer (LabRAM, Resodyn, USA) at the intensity of 70 times the gravitational force and 60 Hz for 5 minutes. The dry coating could be done with other methods. A 300 mL screw top plastic container was used for the dry coating. For each dry coating run, about 66% of the container volume was taken up by powder, which comprised the host excipient and 1 wt % guest silica A200. In all cases where there is a dry coated component, it is limited to 5 wt %, which may be identified in FIG. 47 for various cases.

For the blends formulation used in Example 14 are shown in FIG. 47. Upon preparing blends, mixing parameters such as the order of filling each constituent, mixing intensity, and mixing time were held constant. The powder blend was mixed via a 4-pint V-shaped container for 12 min at 25 rpm. The blending could be done with any other methods.

SEM micrographs (FIG. 19A-19D, coated and uncoated LFP were not shown here) indicated coating of guest material is evident. Even when the excipient has irregular shape, such as for Kollidon CL-F, dry coating of guest material is good and visible on the surface without appreciable agglomeration of the guest material.

Figure 20:
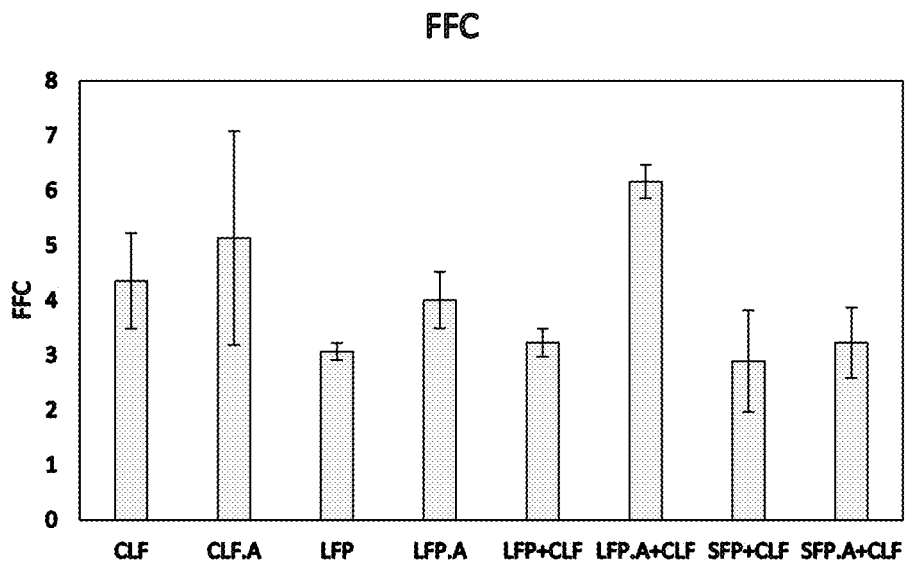
FIG. 20 is a bar graphs illustrating a plot of FFC for blends in Example 14.

FIG. 20 depicts FFC for the as received and dry coated excipient blends listed in FIG. 47. The bars in FIG. 20 are labeled as CLF (only uncoated Kollidon CL-F is included as excipient), CLF.A (only dry coated Kollidon CL-F is included as excipient), LFP (only uncoated HPC L-FP is included as excipient), LFP.A (only dry coated HPC L-FP is included as excipient), LFP+CLF (uncoated Kollidon CL-F and uncoated HPC L-FP are included as excipients), LFP.A+CLF (uncoated Kollidon CL-F and dry coated HPC L-FP are included as excipients), SFP+CLF (Uncoated Kollidon CL-F and uncoated HPC SSL-SFP are included as excipients), and SFP.A+CLF (Uncoated Kollidon CL-F and dry coated HPC SSL-SFP are included as excipients). As shown in FIG. 20, 5 wt % of dry coated excipient is enough to lead to remarkable improvement in the FFC of blends. FFC enhancements show largest gain for LFP.A+CLF, followed by CLF.A, LFP.A and then SFP.A+CLF. 5 wt % of dry coated excipient can achieve 10.2%-47.7% improvement of blend flowability. Although there is the high standard deviation of FFC of CLF.A which is mostly due to rough surface and uneven coating, the blends mostly show good repeatability.

Figure 21:
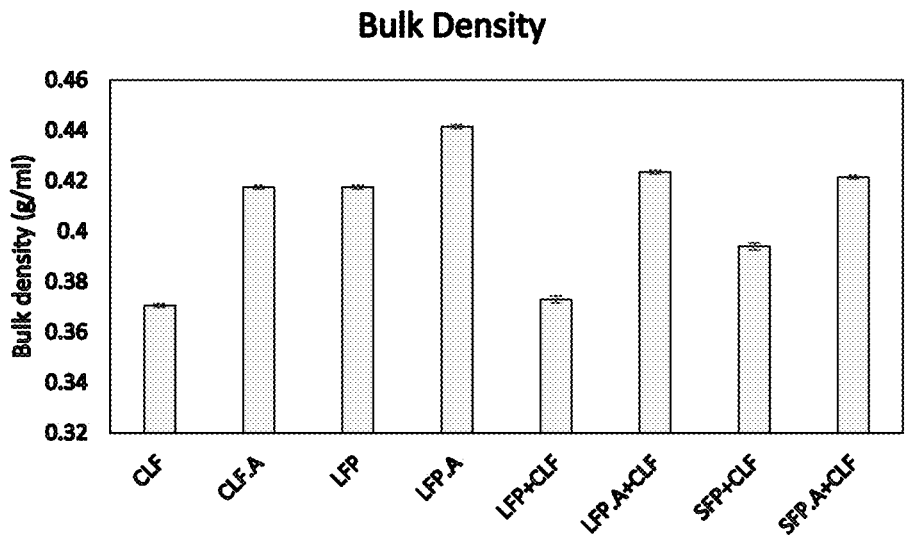
FIG. 21 is a plot of bulk density for blends in Example 14.

FIG. 21 depicts bulk density for the as received and dry coated excipient blends listed in FIG. 47. As shown in FIG. 21, 5 wt % of dry coated excipient could lead to as high as over 10% bulk density improvement of blends. Bulk density enhancements show largest gain for LFP.A+CLF, followed by CLF.A, LFP.A, and then SFP.A+CLF. 5 wt % of dry coated excipient can achieve 5%-13% improvement of blend bulk density, although it is not as high as flowability.

Example 14 Demonstrates that Dry Coated Excipients as Minor Component can Lead to Improvement in the Blends Over as Received Excipients in Terms of Flowability and Bulk Density However, Example 14 does not determine the effects of dry coated excipients on compaction properties of blends, which is discussed in Example 15. In next set of examples, compaction results for blends (Formulations are shown in FIG. 47) are presented.

Figure 22:
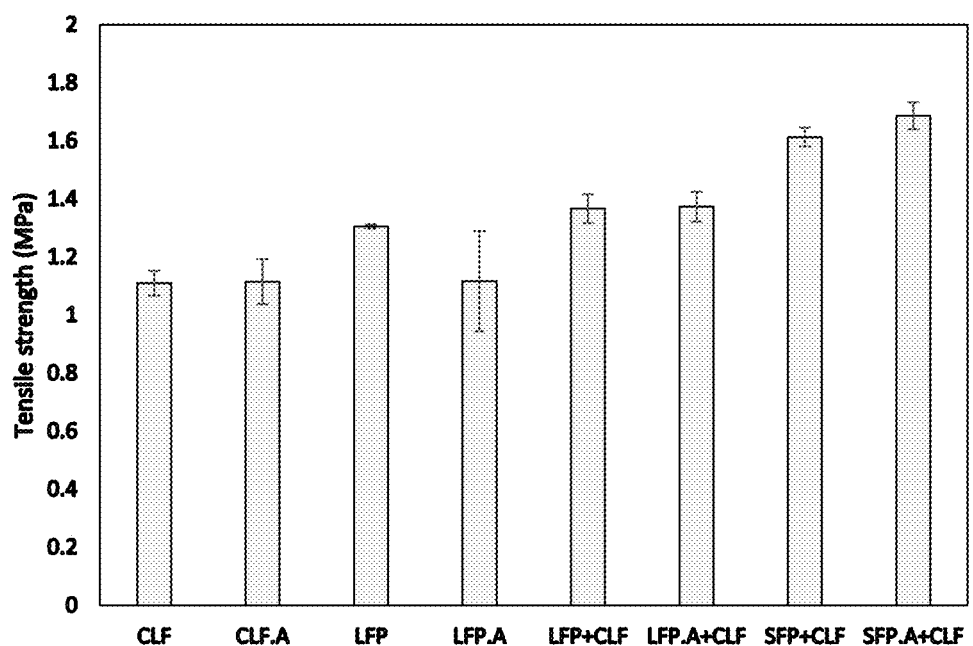
FIG. 22 is a plot of tensile strength for blends in Example 15.

Example 15 Synergistic Effect from the Dry Coated Excipient (Crospovidone and Hydroxy-Propyl Cellulose Based) on Binary or Ternary Blend of High API Loading of Up to 95 wt %—Blend Compaction Improvement Example 15, which is based on the same formulations as Example 14, demonstrates tablet compaction of blends with as received and dry coated excipients (Formulations are shown in FIG. 47). Here, too, it concerns with API loading of 90 wt % and up to 95 wt %. In all cases where there is a dry coated component, it is limited to 5 wt %, which may be identified in FIG. 47 for various cases. The bars in FIG. 22 are labeled in the same way as FIG. 21. The suitability of an excipient intended for a tablet dosage form can be evaluated by its tabletability, compressibility, and compactability. Tabletability, i.e., tablet tensile strength as a function of compaction pressure, is the capability of a powder to gain strength under pressure, and useful to evaluate manufacturability. The tablet tensile strength was evaluated with a texture analyzer (Texture Technologies Corp., USA). Carver platen press (Carver, Inc., USA) with a 0.5-inch inner diameter stainless die and a flat-faced round punch was used to prepare 500 mg tablets under 1.5 metric ton (equivalent to 114 MPa) compaction pressure.

FIG. 22 depicted tensile strength under 1.5 metric ton compression force of blends with the as received and dry coated excipient blends of FIG. 47. As shown in FIG. 22, dry coated blends CLF.A and LFP+CLF.A had almost similar tabletability compared with as received excipient blends, while dry coated SFPA.A+CLF had enhanced tabletability compared with as received excipient blends. Although LFP.A blend shows decreased tabletability, the high variation of tensile strength implies that the loss of tensile strength may have resulted from the uneven mixing of dry coated HPC L-FP. It is surprising that when Ibuprofen 70 is blended with uncoated Kollidon CL-F and dry coated HPC L-FP, the tensile strength is higher than the blends of Ibuprofen 70 with only uncoated Kollidon CL-F or dry coated HPC L-FP (the ternary blend of Ibuprofen 70 has lower amount of Ibuprofen 70).

Examples 14 and 15 suggest that apart from improved flow and packing, dry coating does not have significantly negative impact on forming a tablet.

Example 16 Synergistic Effect from the Dry Coated Excipient (Microcrystalline Cellulose Based) on Binary or Ternary Blend of High API Loading of 60 wt %—Blend Bulk Density and Flowability Improvement Example 16 determines the bulk density, FFC and tensile strength of several blends using as received Avicel® 105, dry coated Avicel® 105, and Prosolv® 50. Prosolv® 50 is used for comparison. In this case, the API loading is high, 60 wt %.

Prior to the blending, as received Avicel® 105 was dry coated with 1 wt % A200 using a high-intensity vibratory mixer (LabRAM, Resodyn, USA) at the intensity of 70 times the gravitational force and 60 Hz for 5 minutes. The dry coating could be done with other methods. A 300 Ml screw top plastic container was used for the dry coating. For each dry coating run, about 66% of the container volume was taken up by powder, which comprised the excipients and 1 wt % guest silica A200.

For the blends formulation used in Example 16 are shown in FIG. 48. Upon preparing blends, mixing parameters such as the order of filling each constituent, mixing intensity, and mixing time were held constant. The powder blend was mixed via a 4-pint V-shaped container for 12 min at 25 rpm. The blending could be done with any other methods.

Figures 23A, 23B:
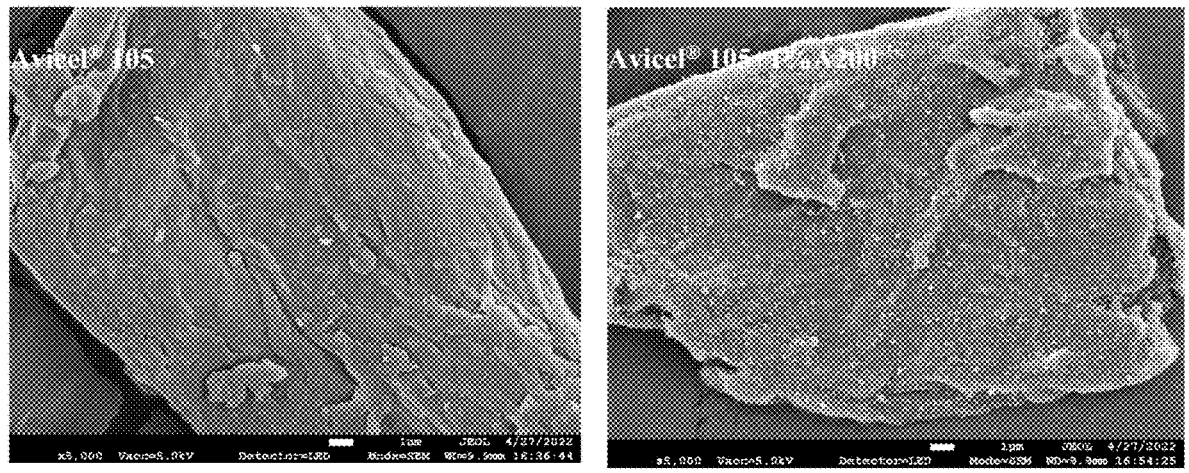
FIGS. 23a-23b are SEM images of uncoated and coated particles of Avicel.

SEM micrographs (FIGS. 23A-23B) indicated coating of guest material is evident. Even when the excipient has irregular shape, such as for Avicel® 105, dry coating of guest material is good and visible on the surface without appreciable agglomeration of the guest material.

The tablet tensile strength was evaluated with a texture analyzer (Texture Technologies Corp., USA). Carver platen press (Carver, Inc., USA) with a 0.5-inch inner diameter stainless die and a flat-faced round punch was used to prepare 500 mg tablets under 1.5 metric ton (equivalent to 114 Mpa) compaction pressure.

Figure 24:
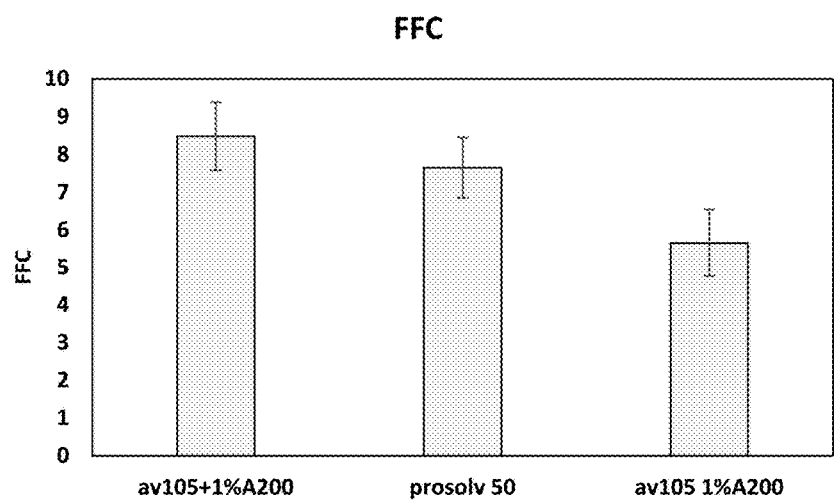
FIG. 24 is a plot of FFC for blends in Example 16.
Figure 25:
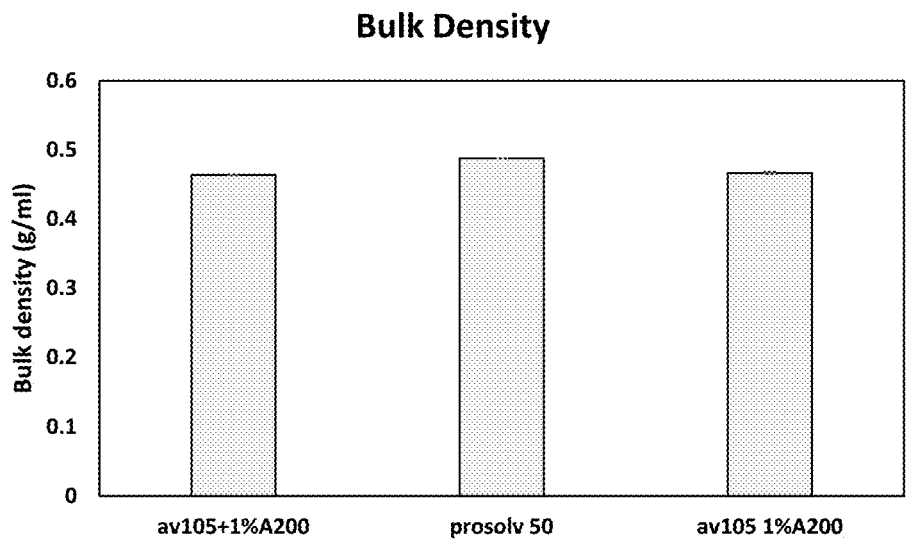
FIG. 25 is a plot of bulk density for blends in Example 16.
Figure 26:
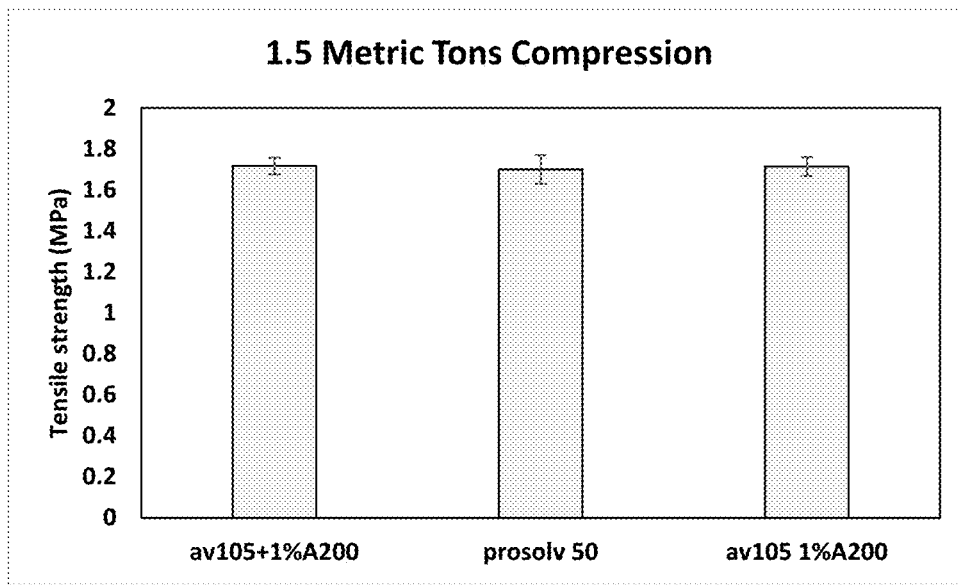
FIG. 26 is a plot of tensile strength for blends in Example 16.

FIG. 24 depicts FFC for the as received excipient and dry coated excipient blends listed in FIG. 48. The bars in FIG. 24-FIG. 26 are labeled as av105 1% A200, av105+1% A200 and Prosolv 50, which mean the blends containing Avicel® 105 blended with 1 wt % A200, Avicel® 105 dry coated with 1 wt % A200, and Prosolv® 50, respectively. FIG. 25 depict bulk density for the of av105 1% A200, av105+1% A200 and Prosolv 50 listed in FIG. 48. FIG. 26 depict tensile strength for the blends of av 105 1% A200, av105+1% A200 and Prosolv 50 listed in FIG. 48.

Three blends show almost similar bulk density and tensile strength, while are differentiated by FFC. It is predictable that the av105 1% A200 blend, where silica was blended only, shows lowest FFC due to the smaller size and higher cohesiveness of Avicel® 105. However, the av105+1% A200 blend has best flowability and has higher FFC than Prosolv 50 blend.

Example 16 proves that dry coated minor component in the blends can bring significant improvement in FFC while there is no compromise on bulk density and tensile strength. The improvement of FFC by 5 wt % dry coated Avicel® 105 is higher than commercialized excipient Prosolv® 50, and the improvement resulted from dry coating cannot be replaced by effect of simply blending.

The synergistic effect resulting from minor dry coated component shows significant enhancement in bulk density and FFC in the blend, which could then not only be formed into tablets but also lead to better quality of sachets and capsules.

Example 17 (Fine and Cohesive Multi-Component Blend, Fixed Mixing Time): Limitation of Simple Physical Mixing of Nano Fumed Silica Compared to the Synergistic Effect from the Dry Coating and Mixing on the Fine Particle Sized Multi-Component Blend of Low API Loading—Blend Flowability Improvement Example 17 compares the low API loaded (5 percent by weight) blends which were prepared by simply mixing nano fumed silica with the multi-component blends with uncoated milled API to the multi-component blends with the dry coated and milled API to highlight the synergistic effect of the dry coating in conjunction with the mixing, which the mixing alone cannot be achieved even with identical components in the blends.

Among 1 to 5 weight percent API loaded cases, a blend case which had the most amount of silica that showed notable synergistic effect from the dry coating and mixing was recreated. Instead of the dry coating the milled and cohesive API, the fumed nano silica was simply mixed into the blend and mixed for 30 minutes.

Using a powder rheometer, FT4 (Freeman Technology, UK) bulk density and flowability under 3.0 kPa of pre-compaction pressure were evaluated. The processability of the powders can also be assessed using a ring shear tester or other types of powder rheometer as well. The results comparing the dry coated then blended versus physical blend are shown in FIG. 49.

FIG. 49 shows that the physical mixture showed notably lesser flowability (Flow Function Coefficient, FFC) improvement than the identical blend with the dry coated API, though still better FFC than the blend with the uncoated API. For instance, the blend containing 5 wt % of API dry coated with R972P at fixed wt % showed FFC increase from 3.30 to 6.50, while the corresponding physical mixture blend showed an FFC improvement from 3.30 to 4.22.

However, interestingly compared to the blend with 5 wt % of uncoated API, the physical mixture blend showed a worsening in bulk density (BD), moving from 0.43 g/Ml to 0.41 g/Ml. Whereas for the blend with the dry coated API, the BD showed no change, which could be attributed to low API loading. These results signify the apparent synergistic effect of the dry coating and mixing combination, which cannot be achieved by simple mixing even if identical compositions and powders from the same batch were used. Also, BD measurement highlights the physical mixture.

Simple mixing would aid the flowability of the cohesive blend marginally. It affects the powder compressibility or BD adversely, showing questionable benefits compared to the synergistic impact from the dry coating and mixing.

Example 18 (Fine and Cohesive Multi-Component Blend, Different Mixing Times): Limitation of Simple Physical Mixing of Nano Fumed Silica Compared to the Synergistic Effect from the Dry Coating and Mixing on the Fine Particle Sized Multi-Component Blend of Higher API Loading of 30 wt %—Blend Flowability Improvement Example 18 compares the high API loaded blends (30 percent by weight) which were prepared by simply mixing nano fumed silica with the multi-component blends with uncoated milled API to the multi-component blends with the dry coated and milled API to highlight the synergistic effect of the dry coating in conjunction with the mixing, which the mixing alone cannot achieve even with identical components in the blends.

Instead of the dry coating of the milled and cohesive API, the fumed nano-silica was simply mixed into the blend and mixed for different mixing times. The selective cases of mixing times were chosen to prepare physical mix blends. All the components used, and the formulation devised for the physical mixture blends are identical to the blend with the dry coated API. FT4 (Freeman Technology, UK) measured bulk density and flowability under 3.0 kPa of pre-compaction pressure. The processability of the powders can also be assessed using a ring shear tester or other types of powder rheometer. The results comparing the dry coated then blended versus physical blend are shown in FIG. 50.

The summarized results from the FT4 assessment are shown in FIG. 50. At the beginning of the mixing, where only 125 rotations were completed, and inadequate mixing was done, the measured powder flowability (Flow Function Coefficient, FFC) was highest for the physical mixture. However, as the mixing time increased, so did the number of rotations, and the clear and steady FFC improvement from the blend with the dry coated API was observed. Whereas for the physical mixture blend, only marginal improvement was observed. Likewise, the blend with dry coated API showed greater BD improvement than the physical mixture. The blend with uncoated API showed BD measurements around 0.385 g/mL, while the blend with dry coated API and physical mixture showed average BD measurements of 0.455 g/mL and 0.438 g/mL, respectively. Both FFC and BD assessments showed that simply mixing silica in the blend cannot increase the powder processability in the range where the dry coating and mixing can induce.

Again, the results shown herein demonstrate that the dry coating of API for all three low drug loadings improved blend uniformity and tablet dissolution due to the agglomerate size reduction along with improved blend flowability and bulk density without adverse impact on tablet compaction, implying enhanced blend processability.

This work aimed at quantifying fine cohesive API agglomeration reduction through dry coating and its impact on enhanced uniformity and processability of multi-component blends at low (1, 3, or 5 wt %) API loadings.

The impact of dry coating with two diverse types and amounts of silica was systematically assessed on cohesion, agglomeration, flowability, bulk density, wettability, and surface energy of fine milled ibuprofen (~10 µm). Agglomerated sizes were measured via gentler gravity-based dispersion, resulting in excellent size resolution. Multi-component blends with fine-sized excipients, selected for reduced downstream segregation, were assessed for their bulk density, blends were evaluated for tensile strength and dissolution.

All dry coated ibuprofen powders exhibited dramatic agglomeration reduction, decreased cohesion, unconfined yield strength, and improved flowability, which are attributed to the nano-scale surface morphology imparted by silica coating. Their blends exhibited profound enhancement in flowability and bulk density even at low API loadings, as well as the content uniformity for the lowest drug loading. Moreover, hydrophobic silica coating improved drug dissolution rate without appreciably reducing tablet tensile strength.

Example 19 (Bimodal Particle Size Distributed Powder System): Bulk Powder Properties Improvement by the Dry Coating of Fines from the Single Component Bimodal Particle Size Distributed API Powder—Flowability and Bulk Density Improvement Example 19 demonstrates enhancement in the bulk powder properties (bulk flow and density) of a single component system comprised of bimodal particle size distribution. 20 wt % of micronized acetaminophen (mAPAP) with a mean particle size (d50) of ~7 µm was blended with 80 wt % of coarse acetaminophen (cAPAP) with d50 of ~23 µm to mimic a single component (an API in this case) powder having a bimodal particle size distribution. Such powder system, having bimodal size distribution without any pre-treatment such as the dry coating served as the control. For another batch of identical component preparation, the 20 wt % of mAPAP was dry coated with a hydrophilic nano-sized fumed silica (A200) at about 100% theoretical surface area coverage (SAC) equivalent to ~1.50 wt % of silica. The coating of mAPAP was done using a high-intensity vibratory mixer, LabRAM, employing the same method mentioned in earlier examples. The dry coated mAPAP portion was blended with uncoated cAPAP using a low-intensity mixer, following the handling and operation method identical to the earlier examples. After mixing, the total wt % of silica in the bimodal powder system was about 0.30 wt %, which is low. Such binary mixture with and without dry coating of the minor, fine constituent, mAPAP were evaluated for their bulk properties using a powder rheometer, FT4 (Freeman Technology, UK), used in the earlier examples, following identical measurement methods and procedures. Whereas the bulk density of untreated blend was 0.302 g/mL, the dry coating of mAPAP, hence fines within the bimodal system, was significantly improved to 0.501 g/mL, representing a remarkable increase of about 66%. Even better, the flowability (FFC) was remarkably increased from about 2.0 to 5.2, advancing the flow regime from very cohesive by two regimes to reach the easy flowing regime. Such enhancements in bulk density and FFC are unexpected because if the entire powder mixture were to be dry coated, the incremental improvement in bulk density would be marginal and in FFC it would remain within the easy flowing regime.

Overall, the dry coating of fines within the bimodal powder system improved the bulk properties of the bimodal component and potentially eliminated the requirement for the wet or dry granulation pre-treatment or even dry coating for the entire population. Although the presented demonstration showed the test case of a bimodal system, as shown in the earlier examples with multi-component, multi-modal powder sizes system of the same component, the dry coating of fines as a minor component is expected to appreciably improve the bulk properties of the entire multi-model powder system, illustrating surprising synergy after mixing. The purpose of this example having such powder system is to illustrate that when the API powder has presence of excessive amounts of fines that comprise 5-10 wt % of total, it may be advantageous to consider dry coating of the fines if pragmatically separable, to potentially achieve better flowability of the full-spectrum material instead of dry coating the entire population.

Example 20: Bulk Powder Properties Improvement by the Dry Coating of a Smaller Portion of 5 wt % or 10 wt % of a Single Fine API Powder Sample—Flowability and Bulk Density Improvement This example considers a relatively fine API, Ibu25, obtained from BASF, having a median particle size, D50, of 25 microns. It is a cohesive powder having FFC of 2.23 and bulk density (BD) of 0.32 g/cm$^3$. Four experimental examples were considered to assess if dry coating of only a minority component could lead to synergistic flowability enhancements while using a limited amount of total silica. In case 20-A, dry coated Ibu25 was prepared using the LabRAM device under standard procedure, 75G, 60 Hz, 5 minutes, by combining 48.9 gram of Ibu50 with 1.1 gram of silica R972P. From this dry coated sample, 2.5 grams of material was taken and mixed with 47.5 grams of uncoated, untreated Ibu25 in a V-blender, blended at 25 rpm for 12 minutes. The resulting mix had total silica amount of 0.11 wt %. Yet, the actual FFC was 5.25, which is significantly higher than uncoated Ibu25. It also attained a bulk density (BD) value of 0.475 g/cm$^3$ which is also an increase of almost 50% as compared to the uncoated, as received Ibu25. Similarly, for case 20-B, dry coated Ibu25 was prepared using the LabRAM device under standard procedure, 75G, 60 Hz, 5 minutes, by combining 49.45 gram of Ibu50 with 0.55 gram of silica R972P. From this dry coated sample, 5 grams of material was taken and mixed with 45.0 grams of uncoated, untreated Ibu25 in a V-blender, blended at 25 rpm for 12 minutes. The resulting mix had the same total silica amount of 0.11 wt % as was the case for 20-A. The major difference between the two situations was that in the first case, 5% of sample was taken and in the second case, 10%. Yet, the actual FFC was 5.00, which is significantly higher than uncoated Ibu25. It also attained a bulk density (BD) value of 0.442 g/cm$^3$ which is also an increase of almost 40% as compared to the uncoated, as received Ibu25. Similarly, cases 20-C and 20-D were prepared where the final V-blended sample silica amount was half that of cases 20-A and 20-B. Specifically, case 20-C, dry coated Ibu25 was prepared using the LabRAM device under standard procedure, 75G, 60 Hz, 5 minutes, by combining 49.45 gram of Ibu50 with 0.55 gram of silica R972P. From this dry coated sample, 2.5 grams of material was taken and mixed with 47.5 grams of uncoated, untreated Ibu25 in a V-blender, blended at 25 rpm for 12 minutes. The resulting mix had total silica amount of 0.055 wt %. Yet, the actual FFC was 4.12, which is still significantly higher than uncoated Ibu25 since it would be classified as easy flow instead of cohesive. It also attained a bulk density (BD) value of 0.449 g/cm$^3$ which is also an increase of over 40% as compared to the uncoated, as received Ibu25. For case 20-D, dry coated Ibu25 was prepared using the LabRAM device under standard procedure, 75G, 60 Hz, 5 minutes, by combining 49.725 gram of Ibu50 with 0.275 gram of silica R972P. From this dry coated sample, 5 grams of material was taken and mixed with 45 grams of uncoated, untreated Ibu25 in a V-blender, blended at 25 rpm for 12 minutes. The resulting mix had total silica amount of very low, 0.055 wt %. Yet, the actual FFC was 4.62, which is significantly higher than uncoated Ibu25. It also attained a bulk density (BD) value of 0.453 g/cm$^3$ which is also an increase of over 40% as compared to the uncoated, as received Ibu25.

Example 21: Bulk Powder Properties Improvement by the Dry Coating of a Minority Portion of Fine API, 5 wt % or Less—Actual FFC Versus Calculated or Predicted Here, selected previous examples where the dry coated API amount is 5 wt % or less are analyzed and tabulated to demonstrate a significantly higher flowability than what one would expect based on the flowability, represented by their FFC, of individual components. The following table data is based on taking the actual FFC values of the dry coated minority component and all other components except for a very minority items of 1 wt % or less except if that component was dry coated. The method for calculating the averaged or predicted FFC is outlined first.

Definition of Averaged or Predicted FFC Based on the Component FFC Values:

The weighted average FFC in a blend using the fractional surface area as weights is described here. Since FFC is a non-linear measure, the procedure outlined below could be conveniently modified but it is generally adequate after capping any FFC>10 to be equal to 10. For simplicity, the particle diameter for species i is taken to be its D50 size. The method comprises estimating the weight of a single particle for each component in the blend based on their densities and particle sizes, calculating the total number of particles of each component based on the mixed quantities, and determining the total surface area of particles for each component. A simplification based on algebraic manipulation can be also done.

The fractional surface area of each component is then determined as the ratio of each component's total surface area to the entire blend's total surface area. These fractional surface areas serve as weights in the weighted averaging of FFC for each component in the blend, thereby offering a more accurate and representative FFC of blends which is dominated by the presence of fine component, whose representation may be more accurate by their more surface area weight fractions compared to coarser components.

Overall, the weighted average FFC in a blend using fractional surface area as weights may be estimated as follows, where any component FFC>10 is capped and made equal to 10:
  Step 1. Estimating the weight ($W_i$) of a single particle for each component in the blend using the formula for the volume of a sphere and the density ($\rho_i$) of each component. For 'i' components, the weights would be calculated as follows: $W_i = 4/3 * \rho_i * (D_i/2)^3 * \rho_i$
  Step 2. Calculating the total number of particles ($N_i$) of each component in the blend, based on the mass quantities in which the components are mixed, $Q_i$: $N_i = Q_i/W_i$; where $\Sigma W_i = W$, total weight
  Step 3. Determining the total surface area ($A_i$) of particles for each component using the formula for the surface area of a sphere: $A_i = N_i * 4 * pi * (D_i/2)^2$
  Step 4. One could simplify the above and directly obtain $A_i = (6*Q_i)/(D_i*\rho_i)$ hence this would be the first step, followed by next two steps
  Step 5. Calculate the fractional surface area ($F_i$) of each component as the ratio of each component's total surface area to the blend's total surface area. For each component 'i', this would be calculated as: $F_i = A_i/\Sigma(A_i)$ for all 'i'
  Step 6. Finally, using the fractional surface areas as weights in the weighted averaging of FFC for each component in the blend: $FFC\_avg = \Sigma(F_i * FFC_i)$ for all 'i'.

The first set of four examples are presented in the table below and are derived from selected cases presented in FIG. 28, where the API was either 5 wt % or 1 wt % and dry coated as shown in column 1 below. In all cases, and that too, remarkably for 1 wt % cases, the calculated, or predicted FFC values ranged from 2.2 to 2.4, which are cohesive but almost very cohesive. However, the actual FFC due to the claimed novelty of our invention, ranged much higher, from 5.4 to as high as 7.1.

|  | 5 wt % loading calculated weighted FFC | Actual 5 wt % loading FFC | 1 wt % loading Calculated weighted FFC | Actual 1 wt % loading FFC |
| --- | --- | --- | --- | --- |
| R972P fixed wt. % | 3.9 | 6.5 | 2.4 | 7.1 |
| A200 fixed wt. % | 2.6 | 5.7 | 2.2 | 7.5 |
| R972P fixed % SAC | 2.7 | 5.7 | 2.2 | 6.0 |
| A200 fixed % SAC | 2.5 | 5.6 | 2.1 | 5.4 |

In the next example, two cases from Example 20 are presented below where in each case, 5 wt % of the API was dry coated and the rest was uncoated, then all mixed at low-intensity V-blender. As seen in this table, although the silica amount did not exceed a very low value of 0.11 wt %, the actual FFC values and hence flow enhancements as compared to calculated ones are remarkably high, demonstrating that only 5 wt % of the API need to be dry coated in a high-intensity device such as LabRAM.

|  | Calculated or Predicted FFC | Actual FFC | Silica wt % |
| --- | --- | --- | --- |
| 5% LabRam + 95% V-Blender | 2.39 | 5.25 | 0.11% |
| 5% LabRam + 95% V-Blender | 2.40 | 4.12 | 0.055% |

As seen from the above table the actual FFC far exceeds the calculated FFC for the blend when using the average FFC by using the individual FFC for each component. This result was unexpected as the amount of silica used was extremely low and the expected FFC should have been very low as well. However, the actual FFC was almost double than expected in this case. Reasons for this unexpected result may vary, yet the present investigators contemplate that the dry coated minority component may act as an additional flow aid and coat the other components in the blend to synergistically provide better flowability and a higher FFC value for the blend than actually calculated by the original FFC values of each component and amount of silica.

While exemplary embodiments have been described herein, it is expressly noted that these embodiments should not be construed as limiting, but rather that additions and modifications to what is expressly described herein also are included within the scope of the invention. Moreover, it is to be understood that the features of the various embodiments described herein are not mutually exclusive and can exist in various combinations and permutations, even if such combinations or permutations are not made express herein, without departing from the spirit and scope of the invention.

The invention claimed is:

1. A pharmaceutical composition, comprising:
  a plurality of fine cohesive powder components forming a pharmaceutical blend and each component having a particle size between 10-30 microns and a flow function coefficient (FFC) under 4 FFC prior to any surface modification or treatment, wherein at least one of the components is an active pharmaceutical ingredient (API);
  the pharmaceutical blend further including:
    a dry coated minority component dry coated with a nano-sized flow aid powder at about 0.1 microns (100 nanometers) or less in particle size; wherein the minority component is the only component dry coated or having any surface modification or treatment, the minority component further defined as one of the plurality of fine powder components having an amount of 0.1 wt % to about less than 5 wt %, based on the total weight of the pharmaceutical blend of all components weight, regardless of the minority component's individual component weight;
  wherein the pharmaceutical blend is formed when only the dry coated minority component is mixed with a remainder of the fine cohesive powder components to form a flow aid concentration in the blend in a range of about 0.116 to 0.007 wt % and the blend surface area coverage (SAC) of about 0.1% to about 9% SAC;
  wherein an actual FFC of the pharmaceutical blend is greater than 4 FFC and an expected and calculated FFC for the pharmaceutical blend and wherein the calculated FFC after dry coating is determined by using a weighted FFC average of the pharmaceutical blend having the plurality of fine cohesive powder components after dry coating the minority component and blending the components, and wherein the actual FFC is determined by testing the pharmaceutical blend after dry coating the minority component and blending the components; and wherein improvement to the actual FFC of the pharmaceutical blend is not from the nano-sized flow aid powder but from the dry coated minority component when mixed in the pharmaceutical blend.

2. The pharmaceutical composition of claim 1, wherein the API has a loading of 1, 3, or 5 wt % of the total blend, and wherein the API is three to five API components.

3. The pharmaceutical composition of claim 1, wherein the API is less than 5 wt % of the total blend that defines a low loading.

4. The pharmaceutical composition of claim 1, wherein the flow aid powder is a silica that has a concentration of about 0.007 wt % to about 0.116 wt %, and the minority component has a lowest FFC value of the blend before the minority component is dry coated as compared to other components in the blend.

5. The pharmaceutical composition of claim 1, wherein the components include an excipient that is a non-coated excipient having no flow aid powder or no silica dry coated thereon.

6. The pharmaceutical composition of claim 1, wherein the API is a fine milled ibuprofen having a particle size of about 10 μm; and wherein the ibuprofen dry coated with the flow aid powder or a silica as compared to a non-dry coated ibuprofen has reduced agglomeration, decreased cohesion, unconfined yield strength, and improved flowability attributed to a nano-scale surface morphology imparted by the flow aid powder or the silica.

7. The pharmaceutical composition of claim 6, wherein the flow aid powder or the silica has a specific surface area ranging from 90 m$^2$/g to 300 m$^2$/g.

8. The pharmaceutical composition of claim 1, wherein the API has a bulk density ranging from about 0.05 g/mL to 0.5 g/mL, and a flow function coefficient or FFC ranging from about 1.0 to 3.5.

9. The pharmaceutical composition of claim 1, wherein the components include an excipient and the excipient has a bulk density from about 0.3 g/mL to about 0.7 g/mL.

10. The pharmaceutical composition of claim 1, wherein the actual FFC of the blend ranges from 4.5 to 30, and the calculated FFC of the blend ranges from 1.0 to 4.

11. The pharmaceutical composition of claim 1, wherein the bulk density of the blend ranges from about 0.2 g/mL to about 0.99 g/mL.

12. The pharmaceutical composition of claim 1, wherein the API has a fine particle defined in a range of 10-15 μm, and the components include a silica and the flow aid powder that dry coats the API at an amount less than 1% wt %, and wherein the flow aid powder is a magnesium stearate or MgSt.

13. A method of preparing a pharmaceutical composition, comprising:

taking a plurality of fine cohesive powder components to form a pharmaceutical blend and each component having a particle size between 10-30 microns and a flow function coefficient or FFC under 4 FFC prior to any surface modification or treatment, wherein at least one of the components is an active pharmaceutical ingredient or API;

only separating from the fine cohesive powder components a minority component defined as 0.1 wt % to about less than wt 5%, based on the total weight of the pharmaceutical blend of all components weight, regardless of the minority component's individual component weight;

dry coating only the minority component with a nano-sized flow aid powder at about 0.1 microns or 100 nanometers, or less in particle size to form only a dry coated minority component;

mixing the only dry coated minority component with a remainder of the fine cohesive powder components to form the pharmaceutical blend;

forming a flow aid concentration in the blend about 0.116 wt. % to 0.007 wt % when the dry coated minority component is mixed with the remainder of the fine cohesive powder components and having a surface area coverage (SAC) of about 0.1% to about 9% SAC;

obtaining an actual FFC of the pharmaceutical blend that is greater than 4FFC and an expected and calculated FFC of the pharmaceutical blend, wherein an actual FFC of the blend is greater than 4 FFC and an expected and calculated FFC for the pharmaceutical blend and wherein the calculated FFC after dry coating is determined by using a weighted FFC average of the blend having the plurality of fine cohesive powder components after dry coating the minority component and blending the components, and wherein the actual FFC is determined by testing the blend after dry coating the minority component and blending the components; and wherein improvement to the actual FFC of the blend is not from the nano-sized flow aid powder but from the dry coated minority component when mixed in the blend.

14. The method of claim 13, wherein the API contains three API components.

15. The method of claim 13, wherein the dry coating the minority component API or an excipient or both the minority component API and the excipient is in an amount less than 1 wt % of the blend.

16. The method of claim 13, wherein the dry coating further includes using a functionalized hydrophobic silica in an amount of 0.01 wt % for the API having a fine particle defined in a range of 10 μm-15 μm.

17. The method of claim 16, wherein the silica is in a range of about 1 wt % to about 2.31 wt % of either a hydrophobic fumed silica or a hydrophilic fumed silica with a specific surface area of 90-225 m$^2$/g.

18. The method of claim 13, where the API is a five component API, and the dry coating further includes using a silica to provide a drug dissolution rate of the blend higher than that compared to an untreated blend.

19. The method of claim 18, wherein the flow aid powder is selected from a group consisting of magnesium stearate (MgSt), Leucine, stearic acid, Sodium Lauryl Sulfate (SLS), Sodium Dodecyl Sulfate (SDS), and any combination thereof.

20. The pharmaceutical composition of claim 1, wherein the flow aid powder has a particle size of about 20 nanometers.

21. The pharmaceutical composition of claim 1, wherein at least one of the API is either dry coated or uncoated.

22. The pharmaceutical composition of claim 1, wherein the API is between 30-50 wt % of the total blend that defines a high loading.

23. The pharmaceutical composition of claim 1, wherein the entire blend is cohesive before dry coating.

24. The pharmaceutical composition of claim 1, wherein the API is cohesive before dry coating.

25. The pharmaceutical composition of claim 1, wherein the one or more fine cohesive powder components after dry coating form a tablet having a tensile strength similar to an as received excipient blend coating.

* * * * *